(12) United States Patent
Mogna

(10) Patent No.: US 12,343,363 B2
(45) Date of Patent: Jul. 1, 2025

(54) **LACTIC ACID BACTERIAL COMPOSITION FOR THE TREATMENT OF BACTERIAL VAGINAL INFECTIONS BY *GARDNERELLA VAGINALIS* AND, IF PRESENT, OF CONCURRENT FUNGAL INFECTIONS**

(71) Applicant: PROBIOTICAL S.P.A., Novara (IT)

(72) Inventor: Giovanni Mogna, Novara (IT)

(73) Assignee: PROBIOTICAL S.P.A., Novara (IT)

( * ) Notice: Subject to any disclaimer, the term of this patent is extended or adjusted under 35 U.S.C. 154(b) by 0 days.

(21) Appl. No.: 17/071,947

(22) Filed: Oct. 15, 2020

(65) Prior Publication Data

US 2021/0023150 A1    Jan. 28, 2021

Related U.S. Application Data

(63) Continuation of application No. 16/087,609, filed as application No. PCT/IB2017/051710 on Mar. 24, 2017, now abandoned.

(30) Foreign Application Priority Data

Mar. 24, 2016   (IT) .................. 102016000031269

(51) Int. Cl.
| | | |
|---|---|---|
| *A61K 35/747* | (2015.01) | |
| *A23L 33/135* | (2016.01) | |
| *A61K 9/00* | (2006.01) | |
| *A61P 15/02* | (2006.01) | |
| *A61P 31/04* | (2006.01) | |
| *A61P 31/10* | (2006.01) | |
| *A61P 31/22* | (2006.01) | |

(52) U.S. Cl.
CPC .......... *A61K 35/747* (2013.01); *A23L 33/135* (2016.08); *A61K 9/0034* (2013.01); *A61K 9/0053* (2013.01); *A61P 15/02* (2018.01); *A61P 31/04* (2018.01); *A61P 31/10* (2018.01); *A61P 31/22* (2018.01)

(58) Field of Classification Search
CPC .. A61K 9/0053; A61K 9/0034; A61K 35/747; A61P 31/10; A61P 31/04; A61P 15/02; A61P 31/22; A23L 33/135
See application file for complete search history.

(56) References Cited

U.S. PATENT DOCUMENTS

| | | | |
|---|---|---|---|
| 3,819,383 | A | 6/1974 | Squire et al. |
| 3,819,838 | A | 6/1974 | Smith et al. |
| 4,187,321 | A | 2/1980 | Mutai et al. |
| 4,332,790 | A | 6/1982 | Sozzi et al. |
| 4,670,272 | A | 6/1987 | Chen et al. |
| 4,853,211 | A | 8/1989 | Kurobe et al. |
| 5,071,976 | A | 12/1991 | Stirling et al. |
| 5,176,911 | A * | 1/1993 | Tosi ........................ A61P 13/02 |
| | | | 435/252.9 |
| 5,343,672 | A | 9/1994 | Kearney et al. |
| 5,413,960 | A | 5/1995 | Dobrogosz et al. |
| 5,466,463 | A | 11/1995 | Ford et al. |
| 5,474,932 | A | 12/1995 | Bengmark et al. |
| 6,221,404 | B1 | 4/2001 | Nguyen et al. |
| 6,262,019 | B1 | 7/2001 | Keller et al. |
| 6,277,370 | B1 | 8/2001 | Cavaliere et al. |
| 6,479,051 | B1 | 11/2002 | Bruce et al. |
| 6,706,347 | B1 | 3/2004 | Kuerzinger et al. |
| 8,257,693 | B2 | 9/2012 | Ranganathan et al. |
| 9,005,682 | B2 | 4/2015 | Sprenger et al. |
| 9,125,768 | B2 | 9/2015 | Husmark et al. |
| 9,492,377 | B2 | 11/2016 | Mogna et al. |
| 9,883,692 | B2 | 2/2018 | Hougee et al. |
| 9,925,224 | B2 | 3/2018 | Mogna et al. |
| 10,028,982 | B2 | 7/2018 | Mogna |
| 10,286,017 | B2 | 5/2019 | Mogna et al. |

(Continued)

FOREIGN PATENT DOCUMENTS

| | | |
|---|---|---|
| AU | 2015100952 A4 | 8/2015 |
| BR | 112013026690 A2 | 12/2016 |

(Continued)

OTHER PUBLICATIONS

Vicariotto F, Del Piano M, Mogna L, Mogna G. Effectiveness of the association of 2 probiotic strains formulated in a slow release vaginal product, in women affected by vulvovaginal candidiasis: a pilot study. J Clin Gastroenterol. Oct. 2012; 46 Suppl:S73-80 (Year: 2012).*

Borges, Sandra, Joana Silva, and Paula Teixeira. "The role of lactobacilli and probiotics in maintaining vaginal health." Archives of gynecology and obstetrics 289.3 (2014): 479-489. (Year: 2014).*

Kaur B, Balgir PP, Mittu B, Kumar B, Garg N. Biomedical applications of fermenticin HV6b isolated from Lactobacillus fermentum HV6b MTCC10770. Biomed Res Int. 2013;2013:168438. doi: 10.1155/2013/168438. Epub Jul. 29, 2013. PMID: 23984320; PMCID: PMC3745898. (Year: 2013).*

Strus M, Chmielarczyk A, Kochan P, Adamski P, Chełmicki Z, Chełmicki A, Pałucha A, Heczko PB. Studies on the effects of probiotic Lactobacillus mixture given orally on vaginal and rectal colonization and on parameters of vaginal health in women with intermediate vaginal flora. (Year: 2012).*

(Continued)

*Primary Examiner* — Robert J Yamasaki
*Assistant Examiner* — Trevor Kane
(74) *Attorney, Agent, or Firm* — Steinfl + Bruno LLP

(57) ABSTRACT

The present invention relates to a pharmaceutical composition or a composition for a medical device or a composition for a food supplement (briefly, the composition (s) of the present invention) based on lactic acid bacteria belonging to the species *Lactobacillus fermentum* for vaginal and oral use for the simultaneous treatment of vaginal infections, disorders or diseases of fungal and bacterial origin. Specifically, the present invention relates to a said composition comprising pharmaceutical- and/or food-grade excipients and a mixture, which comprises or, alternatively, consists of at least a strain of bacteria belonging to the species *Lactobacillus fermentum* for vaginal and oral use for the simultaneous treatment of vaginal infections, disorders or diseases selected from candidiasis, vaginitis, vulvovaginitis or bacterial vaginosis.

12 Claims, 17 Drawing Sheets

(56) References Cited

U.S. PATENT DOCUMENTS

| | | |
|---|---|---|
| 10,384,847 B2 | 8/2019 | Mogna |
| 10,982,184 B2 | 4/2021 | Mogna et al. |
| 11,110,135 B2 | 9/2021 | Mogna et al. |
| 11,110,136 B2 | 9/2021 | Mogna |
| 11,446,340 B2 | 9/2022 | Mogna et al. |
| 2002/0022019 A1 | 2/2002 | Laulund |
| 2002/0044968 A1 | 4/2002 | Van Lengerich |
| 2003/0118571 A1 | 6/2003 | Reid et al. |
| 2004/0185032 A1 | 9/2004 | Burrell |
| 2004/0208863 A1 | 10/2004 | Versalovic et al. |
| 2005/0017013 A1 | 1/2005 | Peisach et al. |
| 2005/0031814 A1 | 2/2005 | Dawes et al. |
| 2005/0095232 A1 | 5/2005 | Volkmann et al. |
| 2005/0220776 A1 | 10/2005 | Brondstad et al. |
| 2006/0039973 A1 | 2/2006 | Aldritt et al. |
| 2006/0121571 A1 | 6/2006 | Klaenhammer et al. |
| 2006/0233774 A1 | 10/2006 | Lim et al. |
| 2007/0122397 A1 | 5/2007 | Sanguansri et al. |
| 2007/0148149 A1 | 6/2007 | Boettner et al. |
| 2007/0207132 A1 | 9/2007 | Speelmans et al. |
| 2007/0269515 A1 | 11/2007 | Henriksen et al. |
| 2008/0175899 A1 | 7/2008 | Ross et al. |
| 2008/0187628 A1 | 8/2008 | Champion et al. |
| 2008/0193485 A1 | 8/2008 | Gorbach et al. |
| 2008/0268006 A1 | 10/2008 | Molin et al. |
| 2008/0299099 A1 | 12/2008 | Heczko et al. |
| 2009/0041736 A1 | 2/2009 | Sprenger et al. |
| 2009/0061164 A1 | 3/2009 | Pasbrig et al. |
| 2009/0170185 A1 | 7/2009 | Hayakawa et al. |
| 2009/0175843 A1 | 7/2009 | Gans et al. |
| 2009/0180999 A1 | 7/2009 | Minatelli et al. |
| 2009/0226548 A1 | 9/2009 | Minatelli et al. |
| 2009/0252709 A1 | 10/2009 | Nose et al. |
| 2009/0294319 A1 | 12/2009 | Naegeli et al. |
| 2010/0003369 A1 | 1/2010 | Ter et al. |
| 2010/0092240 A1 | 4/2010 | Glasser |
| 2010/0092440 A1 | 4/2010 | Strozzi et al. |
| 2010/0168056 A1 | 7/2010 | Troup et al. |
| 2010/0278781 A1 | 11/2010 | Hougee et al. |
| 2011/0020400 A1 | 1/2011 | Macsharry et al. |
| 2011/0177198 A1 | 7/2011 | Songisepp et al. |
| 2011/0178488 A1 | 7/2011 | Balazs et al. |
| 2011/0236360 A1 | 9/2011 | Ochi et al. |
| 2011/0274722 A1 | 11/2011 | Gorbach et al. |
| 2012/0058095 A1 | 3/2012 | Strozzi et al. |
| 2012/0195868 A1 | 8/2012 | Lathan et al. |
| 2012/0207929 A1 | 8/2012 | Yoo et al. |
| 2013/0149342 A1 | 6/2013 | Mogna et al. |
| 2014/0065115 A1* | 3/2014 | Mogna .................. A61K 9/205 424/93.45 |
| 2014/0065116 A1 | 3/2014 | Mogna et al. |
| 2014/0072543 A1 | 3/2014 | Mogna |
| 2014/0093479 A1 | 4/2014 | Mogna et al. |
| 2014/0105874 A1 | 4/2014 | Mogna et al. |
| 2014/0127164 A1 | 5/2014 | Mogna et al. |
| 2014/0186409 A1 | 7/2014 | Lang et al. |
| 2014/0231300 A1 | 8/2014 | Mogna |
| 2014/0328932 A1 | 11/2014 | Mogna et al. |
| 2015/0017128 A1 | 1/2015 | Mogna et al. |
| 2015/0174179 A1 | 6/2015 | Sprenger et al. |
| 2015/0283185 A1 | 10/2015 | Mogna et al. |
| 2016/0106787 A1 | 4/2016 | Mogna et al. |
| 2016/0184372 A1 | 6/2016 | Mogna et al. |
| 2017/0014335 A1 | 1/2017 | Mogna et al. |
| 2017/0049828 A1 | 2/2017 | Kim et al. |
| 2018/0104287 A1 | 4/2018 | Versalovic et al. |
| 2018/0236014 A1 | 8/2018 | Mogna |
| 2019/0015463 A1 | 1/2019 | Mogna |
| 2019/0192586 A1 | 6/2019 | Mogna |
| 2019/0216864 A1 | 7/2019 | Mogna |
| 2019/0321418 A1 | 10/2019 | Mogna |
| 2019/0336547 A1 | 11/2019 | Mogna |
| 2020/0138880 A1 | 5/2020 | Mogna |
| 2020/0164004 A1 | 5/2020 | Mogna |
| 2020/0171106 A1 | 6/2020 | Mogna |
| 2020/0197447 A1 | 6/2020 | Mogna |
| 2020/0199692 A1 | 6/2020 | Mogna |
| 2020/0325440 A1 | 10/2020 | Mogna et al. |
| 2021/0308197 A1 | 10/2021 | Mogna |

FOREIGN PATENT DOCUMENTS

| | | |
|---|---|---|
| CA | 2221426 A1 | 5/1998 |
| CA | 2739345 A1 | 4/2010 |
| CN | 1233474 A | 11/1999 |
| CN | 1345589 A | 4/2002 |
| CN | 1853508 A | 11/2006 |
| CN | 101048168 A | 10/2007 |
| CN | 101432007 A | 5/2009 |
| CN | 101801220 A | 8/2010 |
| CN | 105163747 A | 12/2015 |
| CN | 105377277 A | 3/2016 |
| EA | 200200287 A1 | 6/2002 |
| EA | 010981 B1 | 12/2008 |
| EA | 011952 B1 | 6/2009 |
| EP | 0002692 A1 | 7/1979 |
| EP | 0845350 A1 | 6/1998 |
| EP | 0956858 A1 | 11/1999 |
| EP | 1600060 A1 | 11/2005 |
| EP | 1600061 A1 | 11/2005 |
| EP | 1840205 A1 | 10/2007 |
| EP | 2000530 A1 | 12/2008 |
| EP | 2158916 A1 | 3/2010 |
| EP | 2210505 A1 | 7/2010 |
| EP | 2269465 A1 | 1/2011 |
| EP | 2338976 A1 | 6/2011 |
| EP | 2360237 A1 | 8/2011 |
| EP | 2364712 A1 | 9/2011 |
| EP | 2455095 A1 | 5/2012 |
| EP | 2626076 A1 | 8/2013 |
| EP | 2707477 B1 | 7/2018 |
| EP | 2667849 B1 | 7/2019 |
| GB | 2396811 A | 7/2004 |
| JP | H11504049 A | 4/1999 |
| JP | 2001258549 A | 9/2001 |
| JP | 2002507123 A | 3/2002 |
| JP | 2002508762 A | 3/2002 |
| JP | 2003522731 A | 7/2003 |
| JP | 2006180836 A | 7/2006 |
| JP | 2006519014 A | 8/2006 |
| JP | 2008529535 A | 8/2008 |
| JP | 2009511506 A | 3/2009 |
| JP | 2009520470 A | 5/2009 |
| JP | 2010511033 A | 4/2010 |
| JP | 2010187670 A | 9/2010 |
| JP | 2012527884 A | 11/2012 |
| JP | 2013009681 A | 1/2013 |
| JP | 2016518441 A | 6/2016 |
| KR | 20110057550 A | 6/2011 |
| KR | 20130038395 A | 4/2013 |
| KZ | 11784 A | 8/2002 |
| KZ | 17967 B | 6/2011 |
| RU | 2150268 C1 | 6/2000 |
| RU | 2203946 C1 | 5/2003 |
| RU | 2215656 C2 | 11/2003 |
| RU | 2303058 C2 | 7/2007 |
| RU | 2316586 C2 | 2/2008 |
| RU | 2338511 C2 | 11/2008 |
| RU | 2354392 C1 | 5/2009 |
| RU | 2007147945 A | 7/2009 |
| RU | 2373274 C1 | 11/2009 |
| RU | 2008118418 A | 11/2009 |
| RU | 2388479 C1 | 5/2010 |
| RU | 2445073 C2 | 3/2012 |
| RU | 2465320 C2 | 10/2012 |
| WO | 94/12142 A1 | 6/1994 |
| WO | 97/29762 A1 | 8/1997 |
| WO | 97/29763 A1 | 8/1997 |
| WO | 99/49877 A2 | 10/1999 |
| WO | 00/35465 A2 | 6/2000 |
| WO | 00/35465 A3 | 6/2000 |
| WO | 00/72855 A2 | 12/2000 |
| WO | 03/010298 A1 | 2/2003 |
| WO | 03/090546 A1 | 11/2003 |

(56) References Cited

FOREIGN PATENT DOCUMENTS

| | | | |
|---|---|---|---|
| WO | 2004/003235 | A2 | 1/2004 |
| WO | 2004/087893 | A1 | 10/2004 |
| WO | 2004/089278 | A2 | 10/2004 |
| WO | 2004/101770 | A1 | 11/2004 |
| WO | 2006/013588 | A1 | 2/2006 |
| WO | 2006/073329 | A1 | 7/2006 |
| WO | 2006/082824 | A1 | 8/2006 |
| WO | 2006/091103 | A2 | 8/2006 |
| WO | 2006/102536 | A2 | 9/2006 |
| WO | 2007/020884 | A1 | 2/2007 |
| WO | 2007/029773 | A1 | 3/2007 |
| WO | 2007/050656 | A2 | 5/2007 |
| WO | 2007/100765 | A2 | 9/2007 |
| WO | 2007/125558 | A1 | 11/2007 |
| WO | 2008/038075 | A2 | 4/2008 |
| WO | 2008/065492 | A2 | 6/2008 |
| WO | 2008/107746 | A2 | 9/2008 |
| WO | 2008/153377 | A1 | 12/2008 |
| WO | 2009/138218 | A1 | 11/2009 |
| WO | 2010/023248 | A1 | 3/2010 |
| WO | 2010/033768 | A1 | 3/2010 |
| WO | 2010/038714 | A1 | 4/2010 |
| WO | 2010/099824 | A1 | 9/2010 |
| WO | 2010/103374 | A2 | 9/2010 |
| WO | 2010/128084 | A1 | 11/2010 |
| WO | 2010/133761 | A1 | 11/2010 |
| WO | 2010/136891 | A1 | 12/2010 |
| WO | 2011/002168 | A2 | 1/2011 |
| WO | 2011/012932 | A1 | 2/2011 |
| WO | 2011/017040 | A1 | 2/2011 |
| WO | 2011/044934 | A1 | 4/2011 |
| WO | 2011/110918 | A1 | 9/2011 |
| WO | 2012/001440 | A1 | 1/2012 |
| WO | 2012/101500 | A1 | 8/2012 |
| WO | 2012/123770 | A1 | 9/2012 |
| WO | 2012/126481 | A1 | 9/2012 |
| WO | 2012/143787 | A1 | 10/2012 |
| WO | 2012/153179 | A1 | 11/2012 |
| WO | 2013/034974 | A1 | 3/2013 |
| WO | 2013/034975 | A1 | 3/2013 |
| WO | 2013/050831 | A1 | 4/2013 |
| WO | 2013/050833 | A1 | 4/2013 |
| WO | 2013/093941 | A2 | 6/2013 |
| WO | 2014/023995 | A1 | 2/2014 |
| WO | 2014/184639 | A1 | 11/2014 |
| WO | 2014/184643 | A1 | 11/2014 |
| WO | 2015/170159 | A1 | 11/2015 |
| WO | 2017/025936 | A2 | 2/2017 |
| WO | 2017/085655 | A1 | 5/2017 |
| WO | 2017/163216 | A1 | 9/2017 |
| WO | 2017/208172 | A1 | 12/2017 |
| WO | 2018/025204 | A1 | 2/2018 |
| WO | 2018/215940 | A1 | 11/2018 |
| WO | 2018/234994 | A1 | 12/2018 |
| WO | 2018/234995 | A1 | 12/2018 |

OTHER PUBLICATIONS

Kaur, B., Balgir, P. P., Mittu, B., Chauhan, A., Kumar, B., & Garg, N. (2012). Isolation and In vitro characterization of anti-Gardnerella vaginalis bacteriocin producing Lactobacillus fermentum HV6b isolated from human vaginal ecosystem. International Journal of Fundamental and Applied Sciences (Year: 2012).*

Deidda et al., "In Vitro Activity of *Lactobacillus fermentum* LF5 Against Different *Candida* Species and *Gardnerella vaginalis*: A New Perspective to Approach Mixed Vaginal Infections?," *J. Clin. Gastroenterol.* 50(Supp. 2):S168-S170, 2016.

Hoesl et al., "The Probiotic Approach: An Alternative Treatment Option in Urology," *European Urology* 47:288-296, 2005.

International Search Report, for International Patent Application No. PCT/IB2017/051710, dated Aug. 16, 2017.

Murina et al., "Can *Lactobacillus fermentum* LF10 and *Lactobacillus acidophilus* LA02 in a Slow-release Vaginal Product be Useful for Prevention of Recurrent Vulvovaginal Candidiasis? *A Clinical Study*," *J. Clin. Gastroenterol.* 48:S102-S105, 2014.

"8th Probiotics, Prebiotics, & New Foods for microbiota and human health," Università Urbaniana, Rome—Sep. 13-15, 2015. (152 pages).

European Commission—Health & Consumer Protection Directorate-General, "Opinion of the Scientific Committee on Animal Nutrition on the Criteria for Assessing the Safety of Micro-Organisms Resistant to Antibiotics of Human Clinical and Veterinary Importance," 2002, pp. 1-20.

European Patent Office Communication pursuant to Article 94(3) EPC in relation to Application No. 12780278.3. Mail Date: Jun. 12, 2015, 4 pages.

Final Office Action for U.S. Appl. No. 13/982,255, filed Nov. 12, 2013 on behalf of Giovanni Mogna. Mail Date: Sep. 17, 2015, 15 pages.

Final Office Action for U.S. Appl. No. 14/005,821, filed Nov. 6, 2013 on behalf of Giovanni Mogna. Mail Date: Dec. 30, 2014. 30 pages.

Final Office Action for U.S. Appl. No. 14/113,211, filed Nov. 26, 2013 on behalf of Giovanni Mogna. Mail Date: Nov. 22, 2016, 12 pages.

Final Office Action for U.S. Appl. No. 14/116,996, filed Dec. 18, 2013 on behalf of Giovanni Mogna. Mail Date: Mar. 7, 2016. 22 pages.

Final Office Action for U.S. Appl. No. 14/116,999, filed Dec. 20, 2013 on behalf of Giovanni Mogna. Mail Date: Dec. 9, 2016. 28 pages.

Final Office Action for U.S. Appl. No. 14/117,003, filed Dec. 27, 2013 on behalf of Giovanni Mogna. Mail Date: Jun. 2, 2016. 11 pages.

Final Office Action for U.S. Appl. No. 14/344,021, filed May 9, 2014 on behalf of Giovanni Mogna. Mail Date: Jan. 31, 2017. 19 pages.

Final Office Action for U.S. Appl. No. 14/344,047, filed Jul. 28, 2014 on behalf of Giovanni Mogna. Mail Date: Aug. 4, 2017. 29 pages.

Guonong et al., China; Light Industry Press, 1st Edition in 2009, pp. 363, Publication Date: Aug. 31, 2009, 2 pages (Chinese original+ English excerpt).

International Preliminary Report on Patentability for International Application No. PCT/IB2011/000561 filed Mar. 17, 2011 on behalf of Probiotical S.P.A. Mail Date: Sep. 17, 2013. 6 pages.

International Preliminary Report on Patentability for International Application No. PCT/IB2012/000095 filed Jan. 24, 2012 on behalf of Probiotical S.P.A. Mail Date: Jul. 30, 2013. 8 pages.

International Preliminary Report on Patentability for International Application No. PCT/IB2012/000895 filed May 9, 2012 on behalf of Probiotical S.P.A. Mail Date: Nov. 12, 2013. 7 pages.

International Preliminary Report on Patentability for International Application No. PCT/IB2012/000897 filed May 9, 2012 on behalf of Probiotical S.P.A. Mail Date: Nov. 12, 2013. 6 pages.

International Preliminary Report on Patentability for International Application No. PCT/IB2012/000907 filed May 9, 2012 on behalf of Probiotical S.P.A. Mail Date: Nov. 12, 2013. 6 pages.

International Preliminary Report on Patentability for International Application No. PCT/IB2012/001745 filed Sep. 10, 2012 on behalf of Probiotical North America Inc. Mail Date: Mar. 12, 2014. 8 pages.

International Preliminary Report on Patentability for International Application No. PCT/IB2014/000739 filed May 14, 2014 on behalf of Probiotical S.P.A. Mail Date: Nov. 26, 2015. 14 pages.

International Search Report and Written Opinion for International Application No. PCT/IB2012/000907 filed May 9, 2012 on behalf of Probiotical S.P.A. Mail Date: Sep. 27, 2012. 11 pages.

International Search Report for Application No. PCT/IB2012/000897 filed May 9, 2012 on behalf of Probiotical S.P.A. Mail Date: Aug. 24, 2012. 4 pages.

International Search Report for Application No. PCT/IB2012/001848, Mail Date: Dec. 3, 2012, 3 pages.

International Search Report for International Application No. PCT/IB2011/000561 filed Mar. 17, 2011 on behalf of Probiotical S.P.A. Mail Date: Dec. 16, 2011. 4 pages.

(56) References Cited

OTHER PUBLICATIONS

International Search Report for International Application No. PCT/IB2012/000095 filed Jan. 24, 2012 on behalf of Probiotical S.P.A. Mail Date: Mar. 29, 2012. 4 pages.
International Search Report for International Application No. PCT/IB2012/000779 filed Apr. 18, 2012 on behalf of Giovanni Mogna. Mail Date: Jul. 19, 2012. 5 pages.
International Search Report for International Application No. PCT/IB2012/000895 filed May 9, 2012 on behalf of Probiotical S.P.A. Mail Date: Sep. 21, 2012. 5 pages.
International Search Report for International Application No. PCT/IB2012/001741 filed Sep. 10, 2012 on behalf of Giovanni Mogna. Mail Date: Dec. 3, 2012. 4 pages.
International Search Report for International Application No. PCT/IB2012/001745 filed Sep. 10, 2012 on behalf of Probiotical S.P.A. Mail Date: Dec. 17, 2012. 6 pages.
International Search Report for International Application No. PCT/IB2014/000731 filed May 14, 2014 on behalf of Probiotical S.P.A. Mail Date: Jul. 25, 2014. 7 pages.
International Search Report for International Application No. PCT/IB2014/000739 filed May 14, 2014 on behalf of Probiotical S.P.A. Mail Date: Jul. 31, 2014. 8 pages.
Non-Final Office Action for U.S. Appl. No. 13/982,255, filed Nov. 12, 2013 on behalf of Giovanni Mogna. Mail Date: Mar. 10, 2015. 19 pages.
Non-Final Office Action for U.S. Appl. No. 14/005,821, filed Nov. 6, 2013 on behalf of Giovanni Mogna. Mail Date: Jun. 5, 2014. 36 pages.
Non-Final Office Action for U.S. Appl. No. 14/113,211, filed Nov. 26, 2013 on behalf of Giovanni Mogna. Mail Date: Jan. 22, 2016. 13 pages.
Non-Final Office Action for U.S. Appl. No. 14/113,211, filed Nov. 26, 2013 on behalf of Giovanni Mogna. Mail Date: Apr. 22, 2015. 13 pages.
Non-Final Office Action for U.S. Appl. No. 14/116,996, filed Dec. 18, 2013 on behalf of Giovanni Mogna. Mail Date: May 21, 2015. 29 pages.
Non-Final Office Action for U.S. Appl. No. 14/116,996, filed Dec. 18, 2013 on behalf of Giovanni Mogna. Mail Date: Mar. 27, 2017. 20 pages.
Non-Final Office Action for U.S. Appl. No. 14/116,999, filed Dec. 20, 2013 on behalf of Giovanni Mogna. Mail Date: Jun. 16, 2015. 28 pages.
Non-Final Office Action for U.S. Appl. No. 14/116,999, filed Dec. 20, 2013 on behalf of Giovanni Mogna. Mail Date: Mar. 14, 2016. 25 pages.
Non-Final Office Action for U.S. Appl. No. 14/117,003, filed Dec. 27, 2013 on behalf of Giovanni Mogna. Mail Date: Oct. 14, 2015. 18 pages.
Non-Final Office Action for U.S. Appl. No. 14/344,021, filed May 9, 2014 on behalf of Giovanni Mogna. Mail Date: Apr. 18, 2016. 29 pages.
Non-Final Office Action for U.S. Appl. No. 14/344,047, filed Jul. 28, 2014 on behalf of Giovanni Mogna. Mail Date: Oct. 13, 2016. 27 pages.
Non-Final Office Action for U.S. Appl. No. 14/346,941, filed Mar. 24, 2014 on behalf of Probiotical North America Inc. Mail Date: Apr. 19, 2017. 14 pages.
Non-Final Office Action for U.S. Appl. No. 14/891,306, filed Nov. 13, 2015 on behalf of Probiotical S.P.A. Mail Date: Nov. 22, 2016. 37 pages.
Non-Final Office Action for U.S. Appl. No. 14/891,321, filed Nov. 13, 2015 on behalf of Probiotical S.P.A. Mail Date: Sep. 6, 2017. 14 pages.
Non-Final Office Action for U.S. Appl. No. 15/265,706, filed Sep. 14, 2016 on behalf of Probiotical S.P.A. Mail Date: Jul. 11, 2017. 14 pages.
Notice of Allowance for U.S. Appl. No. 13/982,255, filed Nov. 12, 2013 on behalf of Giovanni Mogna. Mail Date: Jan. 22, 2016. 10 pages.
Notice of Allowance for U.S. Appl. No. 13/982,255, filed Nov. 12, 2013 on behalf of Giovanni Mogna. Mail Date: Jun. 15, 2016. 11 pages.
Notice of Allowance for U.S. Appl. No. 13/982,255, filed Nov. 12, 2013 on behalf of Giovanni Mogna. Mail Date: Jul. 27, 2016. 9 pages.
Notice of Allowance for U.S. Appl. No. 14/117,003, filed Dec. 27, 2013 on behalf of Giovanni Mogna. Mail Date: Nov. 9, 2016. 7 pages.
Notice of Allowance for U.S. Appl. No. 14/117,003, filed Dec. 27, 2013 on behalf of Giovanni Mogna. Mail Date: Jul. 6, 2017. 10 pages.
Office Action for KZ Application No. 20131615.1 filed on Jan. 24, 2012 by Tagbergenova Alma Taishevna et al., Issue Date: Jul. 15, 2014, 5 pages, (Russian Original+ English Translation).
Office Action for Russian Patent Application No. 2013137656/15(056766) filed on Jan. 24, 2012 on behalf of Probiotical S.P.A. mailed on Mar. 18, 2016. 10 pages (Russian original + English translation).
Office Action for Russian Patent Application No. 2014107771/10(012274) filed on behalf of Probiotical S.P.A. Mail Date: Jun. 2, 2016, 8 pages (Russian original+ English translation).
Office Action Inquiry for Russian Patent Application No. 2013144267 filed on Mar. 17, 2011 on behalf of Probiotical S.P.A. Mail Date: Mar. 12, 2015, 5 pages (English Translation).
Official Action for Russian Patent Application No. 2013151611 filed Apr. 18, 2012 on behalf of Giovanni Mogna, Dated: Mar. 30, 2016. 12 pages (Russian original + English translation).
Opposition filed to Application No. SP201312844, Spanish original with English Translation, Date of Notification: Nov. 17, 2015, 14 pages.
Qingbin et al., Science Press, 1st Edition, Jun. 2012, 7 pages (Chinese Original + English Excerpt).
Restriction Requirement for U.S. Appl. No. 13/982,255, filed Nov. 12, 2013 on behalf of Giovanni Mogna. Mail Date: Oct. 17, 2014. 6 pages.
Restriction Requirement for U.S. Appl. No. 14/005,821, filed Nov. 6, 2013 on behalf of Giovanni Mogna. Mail Date: Jan. 7, 2014. 7 pages.
Restriction Requirement for U.S. Appl. No. 14/113,211, filed Nov. 26, 2013 on behalf of Giovanni Mogna. Mail Date: Sep. 5, 2014. 9 pages.
Restriction Requirement for U.S. Appl. No. 14/116,996, filed Dec. 18, 2013 on behalf of Giovanni Mogna. Mail Date: Feb. 4, 2015. 11 pages.
Restriction Requirement for U.S. Appl. No. 14/116,999, filed Dec. 20, 2013 on behalf of Giovanni Mogna. Mail Date: Mar. 11, 2015. 12 pages.
Restriction Requirement for U.S. Appl. No. 14/117,003, filed Dec. 27, 2013 on behalf of Giovanni Mogna. Mail Date: Feb. 20, 2015. 9 pages.
Restriction Requirement for U.S. Appl. No. 14/344,021, filed May 9, 2014 on behalf of Giovanni Mogna. Mail Date: Aug. 14, 2015. 7 pages.
Restriction Requirement for U.S. Appl. No. 14/344,047, filed Jul. 28, 2014 on behalf of Giovanni Mogna. Mail Date: Feb. 19, 2016. 8 pages.
Restriction Requirement for U.S. Appl. No. 14/346,941, filed Mar. 24, 2014 on behalf of Probiotical North America Inc. Mail Date: Nov. 16, 2016. 8 pages.
Restriction Requirement for U.S. Appl. No. 14/891,306, filed Nov. 13, 2015 on behalf of Probiotical S.P.A. Mail Date: Apr. 13, 2016. 7 pages.
Restriction Requirement for U.S. Appl. No. 14/891,321, filed Nov. 13, 2015 on behalf of Probiotical S.P.A. Mail Date: Jun. 16, 2017. 6 pages.
The EFSA Journal, "Opinion of the Scientific Panel on Additives and Products or Substances used in Animal Feed on the updating of the criteria used in the assessment of bacteria for resistance to antibiotics of human and veterinary importance," 2005, 223, 12 pages.

(56) References Cited

OTHER PUBLICATIONS

Third Office Action for Chinese Patent Application No. 201280022854.9, Issue Date: May 17, 2016. 12 pages. (Chinese original + English translation).
Wikipedia "Colony-Forming Unit", Downloaded from the internet Apr. 13, 2017. http://en.wikipedia.org/wiki/Colony-forming unit, 1 page.
Wikipedia "Pharmaceutical Drug" Updated Apr. 15, 2016. Downloaded from the internet Apr. 21, 2016. 11 pages.
Wikipedia, "Strain (biology)" https://en.wikipedia.org/wiki/Strain_(biology) Retrieved on Nov. 3, 2015., 2 pages.
Written Opinion for Application No. PCT/IB2011/000561 filed Mar. 17, 2011 on behalf of Probiotical S.P.A. Mail Date: Dec. 16, 2011. 5 pages.
Written Opinion for Application No. PCT/IB2012/000095 filed Jan. 24, 2012 on behalf of Probiotical S.P.A. Mail Date: Mar. 29, 2012. 8 pages.
Written Opinion for Application No. PCT/IB2012/000779 filed Apr. 18, 2012 on behalf of Giovanni Mogna. Mail Date: Jul. 19, 2012. 5 pages.
Written Opinion for Application No. PCT/IB2012/000895 filed May 9, 2012 on behalf of Probiotical S.P.A. Mail Date: Sep. 21, 2012. 6 pages.
Written Opinion for Application No. PCT/IB2012/000897 filed May 9, 2012 on behalf of Probiotical S.P.A. Mail Date: Aug. 24, 2012. 5 pages.
Written Opinion for Application No. PCT/IB2012/000907 filed May 9, 2012 on behalf of Probiotical S.P.A. Mail Date: Sep. 27, 2012. 5 pages.
Written Opinion for Application No. PCT/IB2012/001741 filed Sep. 10, 2012 on behalf of Giovanni Mogna. Mail Date: Dec. 3, 2012. 9 pages.
Written Opinion for Application No. PCT/IB2012/001745 filed Sep. 10, 2012 on behalf of Probiotical S.P.A. Mail Date: Dec. 17, 2012. 7 pages.
Written Opinion for Application No. PCT/IB2012/001848 filed on Sep. 21, 2012 on behalf of Probiotical S.P.A. Mail Date: Mar. 23, 2014. 3 pages.
Written Opinion for Application No. PCT/IB2014/000731 filed May 14, 2014 on behalf of Probiotical S.P.A. Mail Date: Jul. 25, 2014. 10 pages.
Written Opinion for Application No. PCT/IB2014/000739 filed May 14, 2014 on behalf of Probiotical S.P.A. Mail Date: Jul. 31, 2014. 11 pages.
Restriction Requirement for U.S. Appl. No. 16/615,355, filed Nov. 20, 2019 on behalf of Probiotical S.P.A. Mail Date: May 28, 2021 7 pages.
Ritchie J.M., "Animal Models of Enterohemorrhagic *Escherichia coli* Infection," Microbiology Spectrum, Aug. 15, 2014, vol. 2(4), 13 pages, EHEC-0022-2013.
Rönnqvist D., et al., "Lactobacillus Fermentum Ess-1 with Unique Growth Inhibition of Vulvo-Vaginal Candidiasis Pathogens," Journal of Medical Microbiology, Nov. 2007. vol. 56(Pt 11), 5 pages.
Rowe, R.C. et al., "Handbook of Pharmaceutical Excipients", Chemical Industry Press, 4th Edition, pp. 692-693, (Jan. 31, 2005), 9 pages. (English + Chinese translation).
Russian Patent Office Official Action for Russian Patent Application No. 2015148752/15 filed on behalf of Probiotical S.P.A. Mail Date: Apr. 24, 2018. 11 pages (Russian original + English translation).
Russian Search Report for Russian Application No. 2015148750/15 filed on May 14, 2014 on behalf of Probiotical S.P.A. Mail Date: Mar. 5, 2018. 5 pages. (Russian original + English translation).
Russian Search Report for Russian Application No. 2015148752/15 filed on May 14, 2014 on behalf of Probiotical S.P.A. Mail Date: Apr. 20, 2018. 4 pages. (Russian original + English translation).
Sachet, Webpage from merriam-webster.com, Oct. 7, 2011, accessed via WayBackMachine.com, 1 page.
Saggioro A., "Probiotics in the Treatment of Irritable Bowel Syndrome," Journal of Clinical Gastroenterology, Jul. 2004, vol. 38(6 Suppl), 4 pages.
Santini C., et al., "Characterization of Probiotic Strains: an Application as Feed Additives in Poultry Against Campylobacter Jejuni," International Journal of Food Microbiology, Jul. 2010, vol. 141 (Suppl 1). 11 pages.
Scardovi V., et al., "Multiple Electrophoretic Forms of Transaldolase and 6- Phosphogluconic Dehydrogenase and Their Relationships to the Taxonomy and Ecology of the Bifidobacteria," International Journal of Systematic Bacteriology, vol. 29 (4), Oct. 1979, 312-327. 16 pages.
Schillinger U., et al., "Antibacterial Activity of Lactobacillus sake Isolated from Meat", Applied and Environmental Microbiology, Aug. 1989, vol. 55, No. 8, pp. 1901-1906.
Segers, M.E et al., "Towards a better understanding of Lactobacillus rhamnosus GG-host interactions", Microbial Cell factories, 2014, 13 (Suppl 1): 57. 16 pages.
Sgouras D.N., et al., "Lactobacillus Johnsonii La1 Attenuates Helicobacter Pylori-associated Gastritis and Reduces Levels of Proinflammatory Chemokines in C57bl/6 Mice," Clinical and Diagnostic Laboratory Immunology, Edited by U. Gallo, L. Santamaria., Dec. 2005, vol. 12 (12), 10 pages.
Shigeru Kamiya, "Igaku No Ayumi," Journal of Clinical and Experimental Medicine, 2003, vol. 207 (10), 7 pages.
Shim Y.H., et al., "Antimicrobial Activity of Lactobacillus Strains Against Uropathogens," Pediatrics International, Oct. 2016, vol. 58 (10), 5 pages.
Shin et al., "Pharmacology of Proton Pump Inhibitors," *Curr Gastroenterol Rep*. Dec. 2008; 10(6): 528-534). 11 Pages.
Shu Q., et al., "Immune Protection Mediated by the Probiotic Lactobacillus Rhamnosus HN001 (DR20) Against *Escherichia Coli* O157:H7 Infection in Mice," FEMS Immunology and Medical Microbiology, Sep. 2002, vol. 34 (1), 6 pages.
Simone, et al. "The Probiotic Bifidobacterium breve B632 Inhibited the Growth of Enterobacteriaceae within Colicky Infant Microbiota Cultures", Hindawi Publishing Corporation, BioMed Research International, vol. 2014, article ID 301053 (Aug. 2014). 7 pages.
Strus et al., "Studies on the effects of probiotic Lactobacillus mixture given orally on vaginal and rectal colonization and on parameters of vaginal health in women with intermediate vaginal flora," *European Journal of Obstetrics & Gynecology and Reproductive Biology* 163:210-215, 2012.
Su, X. et al. 2014. Immune responses in Parkinson's disease: interplay between central and peripheral immune systems. *Hindawi Publishing Corporation. BioMed Research International*, Article ID 275178, pp. 1-9; specif. pp. 1, 2.
Terris M.K., et al., "Dietary Supplementation with Cranberry Concentrate Tablets May Increase the Risk of Nephrolithiasis," Urology, Jan. 2001, vol. 57 (1), 4 pages.
Torriani S., et al., "Differentiation of Lactobacillus Plantarum, L. Pentosus, and L. Paraplantarum by recA Gene Sequence Analysis and Multiplex PCR Assay with recA gene-Derived Primers," Applied and Environmental Microbiology, Aug. 2001, vol. 67(8), 3450-3454. 6 pages.
Tsai C.C., et al., "Three Lactobacillus Strains From Healthy Infant Stool Inhibit Enterotoxigenic *Escherichia Coli* Grown in Vitro," Anaerobe, Apr. 2008, vol. 14 (2), 7 pages.
Turroni S., et al., "Oxalate Consumption by Lactobacilli: Evaluation of Oxalyl-CoA Decarboxylase and Formyl-CoA Transferase Activity in Lactobacillus Acidophilus," Journal of Applied Microbiology, Nov. 2007, vol. 103 (5), 10 pages.
Tynkkynen et al., "Comparison of Ribotyping, Randomly Amplified Polymorphic DNA Analysis, and Pulsed-Field Gel Electrophoresis in Typing of Lactobacillus rhamnosus and L. casei Strains," *Applied and Environmental Microbiology* 65(9):3908-3914, 1999.
Ulivieri S, Olivieri G, Filosomi G. "Brain abscess following dental procedures." Case report. Minerva Stomatol. May 2007; 56:303-305. Abstract Only. 1 page.
Valdez et al., "Interference of Lactobacillus plantarum with Pseudomonas aeruginosa in vitro and in infected burns: the potential use of probiotics in wound treatment," Clin Microbiol Infect 11 :472-479 (2005).
Vasiljevic T., et al., "Probiotics-From Metchnikoff to bioactives," International Dairy Journal, Jul. 2008, vol. 18 (7), 15 pages.

(56) References Cited

OTHER PUBLICATIONS

Ventura M. et al., "Identification and Tracing of *Bifidobacterium* Species by Use of Enterobacterial Repetitive Intergenic Consensus Sequences," Applied and Environmental Microbiology, vol. 69 (7), Jul. 2003, 6 pages.

Vicariotto et al., "Effectiveness of the Association of 2 Probiotic Strains Formulated in a Slow Release Vaginal Product, in Women Affected by Vulvovaginal Candidiasis—A Pilot Study," *J Clin. Gastroenterol.* 46(1): S73-S80, 2012.

Vicariotto et al., "Effectiveness of the Two Microorganisms Lactobacillus fermentum LF15 and Lactobacillus plantarum LP01, Formulated in Slow-release Vaginal Tablets, in Women Affected by Bacterial Vaginosis—A Pilot Study," *J Clin. Gastroenterol.* 48(Supp. 1):S106-S112, 2014.

Vicariotto F, "Effectiveness of an Association of a Cranberry Dry Extract, D-Mannose, and the two Microorganisms Lactobacillus Plantarum LP01 and Lactobacillus Paracasel LPC09 in Women Affected by Cystitis: A Pilot Study," Clinical Gastroenterology, Nov.-Dec. 2014, vol. 48 Suppl 1, S96-S101. 6 pages.

Vicariotto F et al., "65: Effectiveness of an Association of a Cranberry Dried Extract, D-Mannose and the Three Microorganisms L. Plantarum LP01, L. Paracasei, LPC09 and S.Thermophilus ST10 in Women Affected by Cystitis: A Pilot Study," 7th Probiotics & Prebiotics New Foods, Sep. 2013, 52 pages.

Vichova, T. et al., "Oxidative Stress: Predictive marker for coronary artery disease", Exp. Clinical Cardiology: Review, (2013), vol. 18, No. 2, pp. e88-e91.

Vuotto et al., "Probiotics to counteract biofilm-associated infections: promising and conflicting data," International Journal of Oral Science 6: 189-194 (2014).

Wagner KW, Schon R, Schumacher M, et al. "Case report: brain and liver abscesses caused by oral infection with *Streptococcus intermedius*." Oral Surg Oral Med Oral Pathol Oral Radial Endod. Oct. 2006; 102:e21-e23. Abstract Only. 1 page.

Wall et al., "Genomic diversity of cultivable Lactobacillus populations residing in the neonatal and adult gastrointestinal tract," *FEMS Microbial Ecol* 59: 127-137, 2007.

Walter J., et al., "Detection and Identification of Gastrointestinal *Lactobacillus* Species by Using Denaturing Gradient Gel Electrophoresis and Species-Specific PCR Primers," Applied and Environmental Microbiology, Jan. 2000, vol. 66 (1), 297-303. 8 pages.

Wang K.Y., et al., "Effects of Ingesting Lactobacillus-and Bifidobacterium-Containing Yogurt In Subjects With Colonized Helicobacter Pylori," American Journal of Clinical Nutrition, Sep. 2004, vol. 80 (3), 5 pages.

Wang Q., et al., "Urinary Tract Infections," Shanghai Liandong Press, Jul. 31, 2001, p. 4 (original + English translation). 5 pages.

Wikipedia definition of p-value (printed on Jul. 3, 2018) 12 pages. https://en.wikipedia.org/wiki/P-value.

Wikipedia entry for "yeast", dated Mar. 1, 2011 (13 pages).

Wikipedia page for "Bacteriocin", downloaded from The Wayback Machine dated Jan. 22, 2016 (7 pages).

Wikipedia page of "Oxidative stress" Downloaded from The Wayback Machine, dated Apr. 12, 2017. 9 pages.

Wikipedia, the free encyclopedia, "Infant formula". 21 pages. Downloaded from The Wayback Machine, with a date of Apr. 1, 2011.

Wiktionary "Bifidogenic" Last modified Jul. 19, 2014, Retrieved from the internet on Apr. 13, 2017, from http://en.wiktionary.org/wiki/bifidogenic, 1 page.

Wiktionary "Cluster—definition" retrieved from the internet on Apr. 27, 2017 from http://web.archive.org/web/20100214060846/https://en.wiktionary.org/wiki/cluster, 4 pages.

Wu et al., "Leaky intestine and impaired microbiome in an amyotrophic lateral sclerosis mouse model," *Physiol. Rep.* 3(4):e12356, 2015. (10 pages).

Yan et al. Inflammatory response in Parkinson's disease (Review). Molecular Medicine Reports. (2014); 10: 2223-2233.

Yeon et al., "Fermented milk of Lactobacillus helveticus IDCC3801 reduces beta-amyloid and attenuates memory deficit," *Journal of Functional Foods* 2: 143-152, 2010.

Ying D.Y., et al., "Microencapsulated Lactobacillus Rhamnosus GG Powders: Relationship of Powder Physical Properties to Probiotic Survival During Storage," Journal of Food Science, Nov. 2010, vol. 75 (9), 8 pages.

Yoon Y., et al., "Occurrence of Glutathione Sulphydryl (GSH) and Antioxidant Activities in Probiotic *Lactobacillus* Spp," Asian-Australasian Journal of Animal Sciences, 2004, vol. 17 (11), 5 pages.

Zanoni S., et al., "Growth Kinetics on Oligo- and Polysaccharides and Promising Features of Three Antioxidative Potential Probiotic Strains," Journal of Applied Microbiology, Nov. 2008, vol. 105 (5), 11 pages.

Zarate et al., "Protective Effect of Vaginal Lactobacillus Paracasei CRL 1289 Against Urogenital Infection Produced by *Staphylococcus aureus* in a Mouse Animal Model," *Infectious Diseases in Obstetrics and Gynecology*, vol. 2007, (Mar. 2007). 6 pages.

Zhang et al., "Target intestinal microbiota to alleviate disease progression in amyotrophic lateral sclerosis," *Clin. Ther.* 39(2):322-336, 2017. (23 pages).

Zhang L., et al., "Evaluation of Lactobacillus Rhamnosus GG Using an *Escherichia coli* K88 Model of Piglet Diarrhoea: Effects on Diarrhoea Incidence, Faecal Microflora and Immune Responses," Veterinary Microbiology, Feb. 2010, vol. 141 (1-2), 7 pages.

Beikler T, Flemming T. "Oral biofilm-associated diseases: trends and implications for quality of life, systemic health and expenditures." Periodontology 2000. 2011; 55:87-103.

D'Auria, "Antifungal activity of *Lavandula angustifolia* essential oil against *Candida albicans* yeast and mycelial form." Medical Mycology, (Aug. 2005). 43, pp. 391-396.

Final Office Action for U.S. Appl. No. 16/624,249, filed Dec. 18, 2019 on behalf of Marben S.R.L. Mail Date: Nov. 20, 2023. 19 pages.

Mazzini L et al., "Theme 10 Therapeutic Strategies: TST-01 Potential role of gutmicrobiota in ALS pathogenesis", *Amyotrophic Lateral Sclerosis and Frontotemporal Degeneration—28th International Symposium on ALS/MND*, vol. 18, No. 2, Nov. 2017, pp. 245-260.

Moon, "Antibacterial activity of essential oils, hydrosols and plant extracts from Australian grown *Lavandula* spp." The International Journal of Aromatherapy, (2006), 16, pp. 9-14.

Notice of Allowance for U.S. Appl. No. 17/230,665, filed Apr. 1, 2021, on behalf of Probiotical S.p.A. Mail Date: Nov. 15, 2023. 20 Pages.

2007 Annual Report, International Scientific Association for Probiotics and Prebiotics, Jan. 1-Dec. 31, 2007, 5 pages.

7th Probiotics & Prebiotics New Food, Universita Urbaniana, Rome, Poster 66: "Effectiveness of the Two Microorganisms L. Fermentum LF15 and L. Plantarum LP01, Formulated in Slow Release Vaginal Tablets, in Women Affected by Bacterial Vaginosis (BV): A Pilot Study," Sep. 2013, 52 pages.

7th Probiotics, Prebiotics & New Foods Proceedings and Abstracts, Retrieved from Internet, [Retrieved on Sep. 2013] URL: Sep. 2013, 206 pages.

Advisory Action U.S. Appl. No. 14/344,047, filed Jul. 28, 2014 on behalf of Giovanni Mogna. Mail Date: Nov. 28, 2017. 13 pages.

Alam M., et al., "Development and Evaluation of Acid-buffering Bioadhesive Vaginal Tablet for Mixed Vaginal Infections," AAPS PharmSciTech, Dec. 2007, vol. 8 (4), 8 pages.

Aloisio I., et al., "Characterization of *Bifidobacterium* spp. Strains for the Treatment of Enteric Disorders in Newborns," Applied Microbiology and Biotechnology, Dec. 2012, vol. 96 (6), 19 pages.

Al-Wahsh, I. et al., "Acute Probiotic Ingestion Reduces Gastrointestinal Oxalate Absorption in Healthy Subjects," Urological Research, 2012, vol. 40 (3), 191-196. 6 pages.

Amaretti A., et al., "Antioxidant Properties of Potentially Probiotic Bacteria: In Vitro and in Vivo Activities," Applied Microbiology and Biotechnology, Jan. 2013, vol. 97 (2), 809-817. 11 pages.

Amoruso, A., et al. A Systematic Evaluation of the Immunomodulatory and Functional Properties of Probiotic Bifidobacterium Breve

(56) References Cited

OTHER PUBLICATIONS

BR03 (DSM 16604) Lactobacillus Plantarum LP01 (LMG P-21021), Journal of Probiotics and Health, vol. 7, Issue 3, No. 214, (Dec. 27, 2019). 9 pages.
Antao E.M., et al., "The Chicken as a Natural Model for Extraintestinal Infections caused by Avian Pathogenic *Escherichia coli* (APEC)," Microbial Pathogenesis, Nov.-Dec. 2008, vol. 45 (5-6), 361-369. 9 pages.
Anukam K.C., et al., "Lactobacillus Plantarum and Lactobacillus Fermentum with Probiotic Potentials Isolated from the Vagina of Healthy Nigerian Women," Research Journal of Microbiology, 2007, vol. 2 (1), 81-87. 8 pages.
Aragon, George et al., Probiotic Therapy for Irritable Bowel; Gastroenterology & Hepatology; United States of America; vol. 6, Issue 1; Jan. 1, 2010; 39-44.
ATCC, Candida albicans (Robin) Berkhout (ATC® 10231TM). Downloaded: May 7, 2017. 3 pages. Website: www.lgcstandards-atcc.org/products/all/10231.aspx?geo_country=de.
ATCC, Candida albicans (Robin) Berkhout (ATCC® 90028TM). Downloaded: May 7, 2017. 2 pages. Website: www.lgcstandards-atcc.org/Products/All/90028.aspx?geo_country=de.
ATCC, Candida glabrata (Anderson) Meyer et Yarrow) (ATCC® 90030TM). Downloaded: May 7, 2017. 2 pages. Website: www.lgcstandards-atcc.org/Products/Collections/Preceptrol_Cultures/90030.aspx?geo_country=de.
ATCC, Candida glabrata (Anderson) Myer et Yarrow (ATCC® 2001TM). Downloaded: May 7, 2017. 2 pages. Website: www.lgcstandards-atcc.org/Products/All/2001.aspx?geo_country=de.
ATCC, Candida parapsilosis (Ashford) Langeron et Talice (TCC® 22019TM). Downloaded: May 7, 2017. 2 pages. Website: www.lgcstandards-atcc.org/products/all/22019.aspx?geo_country=de.
ATCC, Candida tropicalis (Catellani) Berhout (ATCC® 750TM). Downloaded: May 7, 2017. 2 pages. Website: www.lgcstandards-atcc.org/Products/All/750.aspx?geo_country=de.
ATCC, Gardnerella vaginalis (Gardner and Dukes) Greenwood and Pickett (ATCC® 14018TM). Downloaded: May 7, 2017. 2 pages. Website: www.Igcstandards-atcc.org/products/all/14018.aspx?geo_country=de.
ATCC, Issatchenkia orientalis Kudrjanzev (ATCC® 6258TM). Downloaded: May 7, 2017. 2 pages. Website: www.lgcstandards-atcc.org/products/all/6258.aspx?geo_country=de.
Aureli et al., "Metodi microbiologici tradizionali e metodi molecolari per l'analisi delgi integratori alimentari a base di o con probiotici per uso umano," *Rapporti ISTISAN* 8(36): 1-63, 2008 (69 pages) (with English Abstract).
"Bacteriocins" Brenner's Encyclopedia of Genetics (Second Edition), 2013, pp. 277-279. Abstract Only. (3 pages).
Baluka et al., "PCR-Based Detection of Genes Responsible for Oxalate Detoxification In Probiotic Microorganisms," Annual Meeting of the Illinois State Academy of Sciences, 2008 Retrieved from the Internet: [https://www.eiu.edu/biology/posters/2008-11.pdf], 1 page.
Barber A.E., et al., "Strengths and Limitations of Model Systems for the Study of Urinary Tract Infections and Related Pathologies," Microbiology and Molecular Biology Reviews, Jun. 2016, vol. 80 (2), 351-367. 18 pages.
Bartzokas et al., "Relation between mouth and haematogenous infection in total joint replacements," BMJ 309:506-508, 1994. 7 pages.
Basic Microbiology, Eighth edition. Wesley Volk and Jay Brown, eds. Addison-Wesley (1997), pp. 221, 344-345. 5 pages.
Bespalov V.G., et al., "Biologically active food supplements," Kafedra, 2000, pp. 38-47. English Abstract. 12 pages.
Best E.L., et al., "Models for the Study of Clostridium Difficile Infection," Gut Microbes, Mar.-Apr. 2012, vol. 3 (2), pp. 145-167. 23 pages.
Biavati et al., "Electrophoretic Patterns of Proteins in the Genus Bifidobacterium and Proposal of Four New Species," *International Journal of Systematic Bacteriology* 32(3):358-373, Jul. 1982 (16 pages).

Bifisterol Class IIA Medical Device for Oral Use Pamphlet/Packaging from www.probiotical.com . 2 pages. 2015.
Bifisterol Probiotic Product Pamphlet from www.probiotical.com . 2 pages 2015.
Bjarnsholt, "The role of bacterial biofilms in chronic infections," APMIS 121(Suppl. 136):1-51, 2013 (58 pages).
Bloedt, K. et al., "Evaluation of new selective culture media and a rapid fluorescence in situ hybridization assay for identification of Clostridium difficile from stool samples", J Med Microbiol, Jul. 2009, 58 (Pt 7): 874-877.
Boillee S. et al., "ALS: a disease of motor neurons and their nonneuronal neighbors" Neuron, Oct. 2006, 52: 39-59.
Boillee S. et al., "Onsent and progression in inherited ALS determined by motor neurons and microglia" *Science*, Jun. 2, 2006, 312: 1389-1392 (5 pages).
Bondarenko V. M. Molecular-cellular mechanisms of therapeutic action of probiotics. Biologicals. Prevention, diagnosis, treatment. Scientific center of expertise of medical application of the Ministry of health of the Russian Federation (Moscow) 2010 No. 1 (37) p. 31-34; 6 pages.
Bordoni A., et al., "Cholesterol-lowering Probiotics: in Vitro Selection and in Vivo Testing Of bifidobacteria," Applied Microbiology and Biotechnology, Sep. 2013, vol. 97 (18), pp. 8273-8281. 12 pages.
Bornet, F. R. J., et al. "Nutritional aspects of short-chain fructooligosaccharides: natural occurrence, chemistry, physiology and health implications." Digestive and liver disease vol. 34, Supplement 2, Sep. 2002: S111-S120, 10 pages.
Botes, M., et al. "Evaluation of Enterococcus mundtii ST4SA and Lactobacillus plantarum 423 as probiotics by using a gastrointestinal model with infant milk formulations as substrate", International Journal of Food Microbiology (Dec. 2008), 128(2), 362-370. Abstract Only.
Bozzi Cionci, N., et al., "Therapeutic Microbiology: The Role of Bifidobacterium breve as Food Supplement for the Prevention/Treatment of Paediatric Diseases," *Nutrients*, 10, 1723, Published: Nov. 10, 2018. 27 Pages.
Brazilian Office Action for Brazilian Application No. BR112013028496-0 filed May 9, 2012, on behalf of Probiotical S.P.A. Dated: Oct. 6, 2020. Portuguese Original + partial English translation. 9 Pages.
Brazilian Office Action for Brazilian Application No. BR112013028496-0 issued Oct. 17, 2019 on behalf of Probiotical S.P.A., 5 pages. Brazilian + English translation.
Brazilian Office Action for Brazilian Application No. BR112013028705-5 filed on May 9, 2012 on behalf of Probiotical S.P.A., Mail Date: Dec. 14, 2020. 6 pages. Brazilian + partial English translation.
Brazilian Office Action for Brazilian Application No. BR112013028705-5 issued Aug. 14, 2019 on behalf of Probiotical S.P.A., 6 pages. Brazilian + English translation.
Brazilian Patent Office Official Action for Brazilian Patent Application No. BR112015027536-2 filed on behalf of Probiotical S.P.A. , mailed Oct. 2, 2019 , 6 pages. (Brazilian + English translation).
Breach Action Filed by the General Secretary of the Andean Community Against the Republic of Peru, Process 89-AI-2000 (Gaceta Oficial, del Acuerdo de Cartagena, Sumario, Tribunal de Justicia de la Comunidad Andina), Ano XVIII, Numero 722, Lima, Oct. 12, 2001, 44 pages (Spanish with English Abstract).
Briczinski E., et al., "Strain-specific Genotyping of *Bifidobacterium animalis* Subsp Lactis by Using Single-nucleotide Polymorphisms, Insertions and Deletions," Applied and Environmental Microbiology, Dec. 2009, vol. 75 (23), pp. 7501-7508. 8 pages.
Broadbent J.R., et al., "Biochemistry, Genetics, and Applications of Exopolysaccharide Production in *Streptococcus thermophiles*: A Review," Journal of Dairy Science, Feb. 2003, vol. 86 (2), 17 pages.
Busch N.A., et al., "A Model of Infected Burn Wounds Using *Escherichia coli* O18:K1:H7 for the Study of Gram-Negative Bacteremia and Sepsis," Infection and Immunity, Jun. 2000, vol. 68 (6), 3 pages.
Byun et al., "Quantitative Analysis of Diverse *Lactobacillus* Species Present in Advanced Dental Caries," Journal of Clinical Microbiology 42(7):3128-3136, Jul. 2004 (10 pages).

(56) References Cited

OTHER PUBLICATIONS

Canadian Office Action for CA Application No. 2,912,013 filed on May 14, 2014 on behalf of Probiotical S.P.A. Mail Date: Aug. 24, 2020. 4 pages.
Candela M., et al., "High Taxonomic Level Fingerprint of the Human Intestinal Microbiota by Ligase Detection Reaction—Universal Array Approach," BMC Microbiology, Apr. 2010, vol. 10 (116), 17 pages.
Candela M., et al., "Interaction of Probiotic Lactobacillus and Bifidobacterium Strains With Human Intestinal Epithelial Cells: Adhesion Properties, Competition Against Enteropathogens and Modulation of IL-8 Production," International Journal of Food Microbiology, Jul. 2008, vol. 125 (3), 7 pages.
Castro-Leyva V., et al., "Preserved Ex Vivo Inflammatory Status in Decidual Cells from Women with Preterm Labor and Subclinical Intrauterine Infection," PLoS One, Aug. 2012, vol. 7 (8), 6 pages.
Cedarbaum, J.M. et al., "The ALSFRS-R: a revised ALS functional rating scale that incorporates assessments of respiratory function", Journal of the Neurological Sciences, Oct. 1999, vol. 169, pp. 13-21 Abstract Only 3 pages.
Ceri H, Olson ME, Morck OW, et al. The MBEC assay system: Multiple equivalent biofilms for antibiotic and biocide susceptibility testing. Meth Enzymol. 2001; 337:377-384. Summary Only. 2 pages.
CFR—Code of Federal Regulations Title 21, Part 107 "Infant Formula". 2 pages. Downloaded from The Wayback Machine, dated Feb. 22, 2011. 2 Pages.
Champagne C.P., et al., "The Determination of Viable Counts in Probiotic Cultures Microencapsulated by Spray-Coating," Food Microbiology, Dec. 2010, vol. 27 (8), 8 pages.
Chapple IL. "The impact of oral disease upon systemic health-symposium overview." J Dent. 2009; 37: S568-S571. First Page Only.
Charteris et al., "Development and application of an in vitro methodology to determine the transit tolerance of potentially probiotic *Lactobacillus* and *Bifidobacterium* species in the upper human gastrointestinal tract," *Journal of Applied Microbiology* 84: Issue 5, 759-768, Jun. 1998. Abstract Only. 4 pages.
Charteris et al., "Gradient Diffusion Antibiotic Susceptibility Testing of Potentially Probiotic Lactobacilli," *Journal of Food Protection* 64(12):2007-2014, 2001.
Cheikhyoussef A., et al., "Antimicrobial Activity and Partial Characterization of Bacteriocin-like inhibitory Substances (BLIS) Produced by Bifidobacterium Infantis BCRC 14602," Food Control, Jun. 2009, vol. 20 (6), pp. 553-559. 7 pages.
Chen H.L., et al., "Probiotic Lactobacillus casei Expressing Human Lactoferrin Elevates Antibacterial Activity in the Gastrointestinal Tract," Biometals, Jun. 2010, vol. 23 (3), 12 pages.
Chinese Patent Office First Office Action for Chinese Patent Application No. 201480027970.9. Mail Date: Jul. 3, 2018. 12 pages (Chinese Original + English translation).
Chinese Search Report for Chinese Application No. 201480027970.9 filed May 14, 2014 on behalf of Probiotical S.P.A. Mail Date: Jun. 21, 2018. 7 pages. (Chinese Original + English Translation).
Christensen et al., "Adherence of Coagulase-Negative Staphylococci to Plastic Tissue Culture Plates: a Quantitative Model for the Adherence of Staphylococci to Medical Devices," *Journal of Clinical Microbiology* 22( 6): 996-1006, Dec. 1985 (11 pages).
Collado M.C., et al., "Probiotic Strains And Their Combination Inhibit In Vitro Adhesion Of Pathogens To Pig Intestinal Mucosa," Current Microbiology, Springer-Verlag, NE, Jul. 2007, vol. 55 (3), Abstract Only. 1 page.
Collins, M.D et al., "The phylogeny of the genus Clostridium: proposal of five new genera and eleven new species combinations", Int J Syst Bacteriol., Oct. 1994, vol. 44, No. 4: 812-26.
Corrected Notice of Allowability for U.S. Appl. No. 14/116,996, filed Dec. 18, 2013, on behalf of Giovanni Mogna. Mail Date: Mar. 1, 2021. 3 pages.
Corrected Notice of Allowability for U.S. Appl. No. 14/116,996, filed Dec. 18, 2013 on behalf of Giovanni Mogna. Mail Date: Mar. 19, 2021. 4 Pages.
Corrected Notice of Allowability for U.S. Appl. No. 14/891,306, filed Nov. 13, 2015 on behalf of Probiotical S.P.A. Mail Date: Mar. 23, 2021 5 pages.
Corrected Notice of Allowability for U.S. Appl. No. 14/891,306, filed Nov. 13, 2015 on behalf of Probiotical S.P.A. Mail Date: Aug. 20, 2020. 5 pages.
Corrected Notice of Allowability for U.S. Appl. No. 16/368,655, filed Mar. 28, 2019 on behalf of Probiotical S.p.A. Mail date: May 11, 2022. 14 Pages.
Craig RG, Yip JK, So MK, et al. "Relationship of destructive periodontal disease to the acute-phase response." J Periodontal. 2003;74(7):1007-1016. Abstract Only. 3 pages.
Cremonini F., et al., "Effect of Different Probiotic Preparation son Anti-Helicobacter pylori Therapy-Related Side Effects: A Parallel Group, Triple Blind, Placebo-Controlled Study," American Journal of Gastroenterology, 2002, vol. 97 (11), 7 pages.
Dai, Dao-Fu, et al. "Mitochondrial oxidative stress in aging and healthspan", Longevity and Healthspan, (2014), 3: 6, 22 pages.
Danielsen et al., "Susceptibility of *Lactobacillus* spp. to antimicrobial agents," *International Journal of Food Microbiology* 82:1-11, Jan. 2003. Abstract Only. 1 page.
Darouiche R.O., et al., "Bacterial Interference for Prevention of Urinary Tract Infection: a Prospective, Randomized, Placebo-controlled, Double-blind Pilot Trial," Clinical Infectious Diseases, vol. 41 (10), 1531-1534, (Nov. 2005). 4 pages.
Database WPI Week 2011109, Thomson Scientific, London GB, for WO 2011/002168, AN: 2011-A52648, Jan. 6, 2011. 2 pages.
Database WPI Week 2011167, Thomson Scientific, London GB, for KR 2011 0057550, AN: 2011-H38885, Jun. 1, 2011. 2 pages.
Davies D. "Understanding biofilm resistance to antibacterial agents." Nat Rev Drug Discov. 2003;2: 114-122. Abstract Only.
De Keersmaecker S.C., et al., "Strong Antimicrobial Activity of Lactobacillus Rhamnosus GG Against *Salmonella typhimurium* is due to Accumulation of Lactic Acid," Federation of European Microbiological Societies Microbiology Letters, Jun. 2006, vol. 259(1), 8 pages.
Decision of Rejection for Chinese Application No. 201280031191. 7, issued on May 12, 2020, with English translation. 14 pages.
Decision of Rejection for CN201280022854 filed on behalf of Probiotical S.P.A. on Nov. 11, 2013. Mail date: Sep. 8, 2017. (Chinese Original + English translation). 18 pages.
Decision to Grant a Patent for Invention issued for Russian application No. 2013148474 filed on May 9, 2012. Mail Date: May 19, 2017, 11 pages (English Translation and Russian Original).
Decision to Grant for Russian Patent Application No. 2014107771/ 10 filed Sep. 10, 2012 on behalf of Probiotical S.P.A. Mail Date: May 23, 2017. 11 pages (Russian original+ Partial English translation).
Decision to Grant mailed on May 31, 2017 for Russian Patent Application No. 2013148476/15 filed on May 9, 2012 on behalf of Probiotical S.P.A, 15 pages. (Russian Original + 2 pages of English Translation).
Decision to Grant mailed on Sep. 2, 2016 for Russian Patent Application No. 2014110640/05 filed on Sep. 21, 2012 on behalf of Probiotical S.P.A., 9 pages.
Deidda et al., "In Vitro Activity of Lactobacillus fermentum LF5 Against Different *Candida* Species and Gardnerella vaginalis: A New Perspective to Approach Mixed Vaginal Infections?," *J Clin. Gastroenterol.* 50(Supp.2):S168-S170, Nov./Dec. 2016 (12 pages).
Del Piano et al., "In Vitro Sensitivity of Probiotics to Human Pancreatic Juice," *J Clin Gastroenterol* 42:S170-S173, Sep. 2008. Abstract Only. 8 pages.
Del Piano et al., presented in the 7th Probiotics, Prebiotics & New Foods Meeting held in Rome on Sep. 8-10, 2013, published in Journal of Clinical Gastroenterology, 48/Suppl 1: S56-61, 2014 (Year: 2013).
Del Piano M., et al., "Correlation Between Chronic Treatment with Proton Pump Inhibitors (PPIs) and Bacterial Overgrowth in the

(56) References Cited

OTHER PUBLICATIONS

Stomach: Any Possible Beneficial Role for Selected Lactobacilli?," Journal of clinical gastroenterology, Nov. 2014, vol. 48 Suppl 1, 7 pages.

Del Piano M., et al., "Evaluation of the Intestinal Colonization by Microencapsulated Probiotic Bacteria in Comparison With Same Uncoated Strains," Journal of clinical gastroenterology, Sep. 2010, vol. 44 Suppl 1, 5 pages.

Del Piano M., et al., "Is Microencapsulation the Future of Probiotic Preparations? The Increased Efficacy of Gastro-protected Probiotics," Gut Microbes, Mar. 2011, vol. 2 (2), pp. 4 pages.

Denol, retrieved on Mar. 29, 2016, from the Internet: URL: www.rlsnet.ru/tn_index_id_6426.html, 2009, 5 pages including English translation.

Desai et al., "Discrimination of Dairy Industry Isolates of the Lactobacillus casei Group," *J Dairy Sci.* 89(9):3345-3351, 2006 (7 pages).

"The Language of Prevention" from National Public Health Partnership, 2006. Melbourne: NPHP. 9 pages.

"Study on Optimization of Exopolysaccharide and Characteristics of *Streptococcus thermophilus* ST1," 2011. 73 pages (7-8). (English Abstract).

Douillard F.P., et al., "Comparative Genomic and Functional Analysis of 100 Lactobacillus Rhamnosus Strains and their Comparison with Strain GG," PLOS Genetics, Aug. 2013, vol. 9 (8), 15 pages.

Dr. Jose Ma Sune Negre, "New Galenic Formulations to Forms of Administration" (English translation of "Nuevas Aportaciones Galenicas a las Formas de Administracion". En: Curos de formacion continuada para farmaceuticos de hospital. Fundacion Promocion Medica. Barcelona, 2002, 3, pp. 27-65), 3.2., Spanish with English Abstract, 27 pages.

Drago L. et al., "Effects of Lactobacillus salivarius LS01 (DSM 22775) treatment on adult Atopic dermatitis: A randomized placebo-controlled study", *International Journal of Immunopathology and Pharmacology*, vol. 24, No. 4, 2011, pp. 1037-1048 (12 pages).

Eaton K.A., et al., "Probiotic Lactobacillus Reuteri Ameliorates Disease Due to Enterohemorrhagic *Escherichia coli* in Germfree Mice," Infection and Immunity, Jan. 2011, vol. 79 (1), 9 pages.

Egervarn et al., "Antibiotic Susceptibility Profiles of Lactobacillus reuteri and Lactobacillus fermentum," *Journal of Food Protection* 70(2):412-418, 2007.

European Food Safety Authority, "Guidance on the assessment of bacterial susceptibility to antimicrobials of human and veterinary importance," *EFSA Journal* 10(6):2740, 2012 (10 pages).

European Food Safety Authority, "Opinion of the Scientific Panel on Additives and Products or Substances used in Animal Feed on the updating of the criteria used in the assessment of bacteria for resistance to antibiotics of human or veterinary importance," *The EFSA Journal* 223: 1-12, May 25, 2005.

European Food Safety Authority, Technical guidance, "Update of the criteria used in the assessment of bacterial resistance to antibiotics of human or veterinary importance," *The EFSA Journal* 7 32: 1-15, Jun. 18, 2008.

Examination Report, for European Application No. 17724279.9, dated Oct. 8, 2019. (5 pages).

Examination Report for Indian Application No. 8722/CHENP/2013 filed on behalf of Probiotical S.P.A. Mail Date: Jul. 5, 2018. 8 Pages. (Hindi + English Translation).

Examination Report mailed on Apr. 28, 2014 for New Zealand IP No. 614002 filed on Aug. 6, 2013 in the name of Probiotical S.P.A., 2 pages.

FAO/WHO, Guidelines for the Evaluation of Probiotics in Food, Apr. 30, 2002, 11 pages.

Federici F., et al., "Characterization and Heterologous Expression of the Oxalyl Coenzyme A Decarboxylase Gene from Bifidobacterium lactis," Applied and Environmental Microbiology, Sep. 2004, vol. 70 (9), 8 pages.

Fernandez M.F., et al., "Probiotic Properties of Human Lactobacilli Strains to be used in the Gastrointestinal Tract," Journal of Applied Microbiology, 2003, vol. 94 (3), 7 pages.

Final Office Action for U.S. Appl. No. 14/113,211, filed Nov. 26, 2013, on behalf of Giovanni Mogna. Mail Date: Jan. 18, 2022. 26 Pages.

Final Office Action for U.S. Appl. No. 14/113,211, filed Nov. 26, 2013, on behalf of Hoffmann-Eitle Srl. Mail Date: Sep. 28, 2018. 23 pgs.

Final Office Action for U.S. Appl. No. 14/113,211, filed Nov. 26, 2013 on behalf of Giovanni Mogna. Mail Date: Mar. 4, 2020. 25 pages.

Final Office Action for U.S. Appl. No. 14/116,996, filed Dec. 18, 2013 on behalf of Giovanni Mogna. Mail date: Dec. 14, 2017. 18 pages.

Final Office Action for U.S. Appl. No. 14/346,941, filed Mar. 24, 2014 on behalf of Probiotical North America Inc. Mail date: Jan. 22, 2018. 14 pages.

Final Office Action for U.S. Appl. No. 14/891,306, filed Nov. 13, 2015 on behalf of Probiotical S.P.A. Mail date: Jan. 18, 2018. 41 pages.

Final Office Action for U.S. Appl. No. 14/891,321, filed Nov. 13, 2015 on behalf of Probiotical S.P.A. Mail Date: Apr. 25, 2018. 8 pages.

Final Office Action for U.S. Appl. No. 15/265,706, filed Sep. 14, 2016 on behalf of Probiotical S.P.A. Mail date: Feb. 2, 2018. 34 pages.

Final Office Action for U.S. Appl. No. 16/322,843, filed Feb. 1, 2019 on behalf of Probiotical S.P.A. Mail Date: Oct. 13, 2021. 19 pages.

Final Office Action for U.S. Appl. No. 16/368,655, filed Mar. 28, 2019 on behalf of Probiotical S.P.A Mail Date: Jul. 14, 2020. 14 pages.

Final Office Action for U.S. Appl. No. 16/624,249, filed Dec. 18, 2019 on behalf of Marben S.R.L. Mail Date: Sep. 7, 2022. 52 pages.

Final Office Action for U.S. Appl. No. 14/116,996, filed Dec. 18, 2013 on behalf of Probiotical S.P.A. Mail Date: Jan. 25, 2019. 29 pages.

First Examination Report mailed on Feb. 12, 2016 for Chilean application No. 2013002148 filed on Jul. 26, 2013, 21 pages.

First Examination Report mailed on Mar. 9, 2016 for Chilean application No. 2013002148 filed on Jul. 26, 2013, 21 pages.

Fourth Office Action for Chinese Patent Application No. 201280015994.3 filed on behalf of Probiotical S.P.A. Issue Date: May 22, 2018. 20 pages. (English Translation + Chinese Original).

Franks, A.H. et al. "Variations of bacterial populations in human feces measured by fluorescent in situ hybridization with group-specific 16S rRNA-targeted oligonucleotide probes" Appl Environ Microbiol, Sep. 1998, vol. 64, N(9), 3336-45.

Galante et al., "Quorum Sensing and Biofilms in the Pathogen, *Streptococcus pneumoniae*," *Current Pharmaceutical Design* 21:25-30, 2015. Abstract Only. 1 page.

Gallo V. et al., "Prediagnostic body fat and risk of death from amyotrophic lateral sclerosis: the EPIC cohort" *Neurology*. 2013, 80(9): 829-38.

Germond J.E., et al., "Evolution of the Bacterial Species Lactobacillus delbrueckii: a Partial Genomic Study with Reflections on Prokaryotic Concept," Molecular Biology and Evolution, Jan. 2003, vol. 20 (1), 12 pages.

Giglione, E., et al. "The Association of Bifidobacterium breve BR03 and B632 is Effective to Prevent Colics in Bottle-fed Infants", Journal of Clinical Gastroenterology, vol. 50 (2), S164-S167, (Nov. 2016). 4 pages.

Gillor, O. et al. "The dual role of bacteriocins as anti- and probiotics", Appl Microbiol Biotechnol. Dec. 2008; 81(4): 591-606. (25 pages).

Gotteland M., et al., "Systematic Review: Are Probiotics Useful in Controlling Gastric Colonization by Helicobacter Pylori?," Alimentary Pharmacology & Therapeutics, Apr. 2006, vol. 23 (8), 10 pages.

Grill J.P., et al., "Bile Salt Toxicity to Some Bifidobacteria Strains: Role of Conjugated Bile Salt Hydrolase and pH," Canadian Journal of Microbiology, Oct. 2000, vol. 46 (10), 878-884. 7 pages.

Grimoud Julien, et al., "In Vitro Screening of Probiotic Lactic Acid Bacteria and Prebiotic Glucooligosaccharides to Select Effective Synbiotics," Anaerobe, Oct. 2010, vol. 16 (5), pp. 493-500. 8 pages.

(56) References Cited

OTHER PUBLICATIONS

Guardamagna O., et al., "Bifidobacteria Supplementation: Effects on Plasma Lipid Profiles in Dyslipidemic Children," Nutrition, Jul.-Aug. 2014, vol. 30 (7-8), 6 pages.
Gueimonde M., "Adhesion and Competitive Inhibition and Displacement of Human Enteropathogens by Selected Lactobacilli," Food Research International, May 2006, vol. 39 (4), 5 pages.
Guo X., "Basics and Application of Probiotics," Science and Technology Press, 1st Version, Oct. 2002, 4 pages (Chinese Original and English Translation).
Gurbuz A.K., et al., "Effect of N-Acetyl Cysteine on Helicobacter Pylori," Southern Medical Journal, Nov. 2005, vol. 98 (11), 4 pages.
Hamilton-Miller J.M., et al., "The Role of Probiotics in the Treatment and Prevention of Helicobacter Pylori Infection," International Journal of Antimicrobial Agents, Oct. 2003, vol. 22 (4), 7 pages.
Harmsen, H.J.M. "A 16S rRNA-targeted probe for detection of lactobacilli and enterococci in faecal samples by fluorescent in situ hybridization" Microb Ecol Health Dis., 1999, 11: 3-12.
Hayashi, Y. et al., "Reverse of Age-Dependent Memory Impairment and Mitochondrial DNA Damage in Microglia by an Overexpression of Human Mitochondrial Transcription Factor A in Mice", The Journal of Neuroscience, Aug. 20, 2008, 28 (34): 8624-8634.
Hearing Notice for Indian Application No. 8722/CHENP/2013 filed on behalf of Probiotical S.P.A. Date of Dispatch: Oct. 17, 2019. 3 Pages (Hindi+ English Translation).
Hemert S.V., et al., "Influence of the Multispecies Probiotic Ecologic® Barrier on Parameters of Intestinal Barrier Function," Food and Nutrition Sciences, Sep. 2014, vol. 5 (18), 8 pages.
Hoesl C.E., et al., "The Probiotic Approach: An Alternative Treatment Option in Urology," European Urology, Mar. 2005, vol. 47 (3), 9 pages.
Hung et al., "Emerging Concepts of Biofilms in Infectious Diseases," *Missouri Medicine* 106(4):292-296, Jul./Aug. 2009 (6 pages).
Hutt P., et al., "Antagonistic Activity of Probiotic Lactobacilli and Bifidobacteria Against Entero- and Uropathogens," Journal of Applied Microbiology, Jun. 2006, vol. 100 (6), 9 pages.
Huynh H.Q., et al., "N-acetylcysteine, A Novel Treatment for Helicobacter Pylori Infection," Digestive Diseases and Sciences, Nov.-Dec. 2004, vol. 49 (11-12), 9 pages.
Infante Pina D., et al., "Prevalence and Dietetic Management of Mild Gastrointestinal Disorders in Milk-fed Infants," World Journal of Gastroenterology, Jan. 2008, vol. 14 (2), 7 pages.
International Preliminary Report on Patentability for Application No. PCT/IB2012/001741 filed Sep. 10, 2012 on behalf of Giovanni Mogna. Mail Date: Mar. 12, 2014. 10 pages.
International Preliminary Report on Patentability for Application No. PCT/IB2012/001848 filed Sep. 21, 2012 on behalf of Probiotical S.P.A. Mail Date: Mar. 25, 2014. 4 pages. (English Only).
International Preliminary Report on Patentability for Application No. PCT/IB2014/000731 filed May 14, 2014 on behalf of Probiotical S.P.A. Mail Date: Nov. 17, 2015. 11 pages (English Only).
International Preliminary Report on Patentability for Application No. PCT/IB2017/051710 filed Mar. 24, 2017 on behalf of Probiotical S.P.A. Mail Date: Sep. 25, 2018. 7 pages.
International Preliminary Report on Patentability for Application No. PCT/IB2017/054734 filed Aug. 2, 2017 on behalf of Probiotical S.P.A. Mail Date: Feb. 5, 2019. 7 pages.
International Preliminary Report on Patentability for International Application No. PCT/IB2012/000779 filed Apr. 18, 2012 on behalf of Giovanni Mogna. Mail Date: Oct. 22, 2013. 6 pages. (English Only).
International Preliminary Report on Patentability for International Application No. PCT/IB2012/001741 filed Sep. 10, 2012 on behalf of Giovanni Mogna. Mail Date: Mar. 12, 2014.10 pages.
International Preliminary Report on Patentability for International Application No. PCT/IB2018/054508 filed on Jun. 19, 2018 on behalf of Probiotical S.P.A. Mail Date: Dec. 24, 2019 7 pages.
International Preliminary Report on Patentability for International Application No. PCT/IB2018/054509 filed on Jun. 19, 2018 on behalf of Probiotical S.P.A. Mail Date: Dec. 24, 2019 10 pages.
International Preliminary Report on Patentability for International Patent Application No. PCT/IB2018/053632, dated Nov. 26, 2019. 7 pages.
International Search Report and Written Opinion for International Application No. PCT/IB2018/054508 filed on Jun. 19, 2018 on behalf of Probiotical S.P.A. Mail Date: Aug. 23, 2018 10 pages.
International Search Report and Written Opinion, for International Application No. PCT/IB2018/053632, mailed Jul. 30, 2018, 10 pages.
International Search Report and Written Opinion for International Application No. PCT/IB2018/054509 filed on Jun. 19, 2018 on behalf of Probiotical S.P.A. Mail Date: Oct. 9, 2018 14 pages.
International Search Report and Written Opinion for International Patent Application No. PCT/IB2017/051710, dated Aug. 16, 2017. 12 pages.
International Search Report and Written Opinion for International Patent Application No. PCT/IB2017/054734, dated Nov. 13, 2017. 11 pages.
Italian Search Report and Written Opinion for MI20110792. Mail Date: Nov. 11, 2011. 9 pages.
Jackson, S.A et al., "Improving End-User Trust in the Quality of Commercial Probiotic Products", Frontiers in Microbiology, Apr. 2019, vol. 10, Article 739, 15 pages. www.frontiersin.org.
Japanese Office Action for Japanese Application No. 2014-529082 filed Mar. 7, 2014 on behalf of Probiotical S.P.A. Mail date: Jul. 19, 2016. 13 pages (Japanese Original + English Translation).
Japanese Patent Office Decision To Grant for Japanese Patent Application No. 2016- 513453 filed on behalf of Probiotical S.P.A , certification date Sep. 3, 2019, Mail Date: Sep. 10, 2019. 7 pages (Japanese + English translation).
Japanese Patent Office Official Action for Japanese Patent Application No. 2013550962. Mail Date: Dec. 1, 2015. 10 pages (Japanese original+ English translation).
Japanese Patent Office Official Action for Japanese Patent Application No. 2013558517. Mail Date: Mar. 3, 2015. 4 pages (Japanese original+ English translation).
Japanese Patent Office Official Action for Japanese Patent Application No. 2014509849. Mail Date: Apr. 26, 2016. 9 pages (Japanese original + English translation).
Japanese Patent Office Official Action for Japanese Patent Application No. 2014529081. Mail Date: May 31, 2016. 8 pages (Japanese original+ English translation).
Japanese Patent Office Official Action Summary for Japanese Patent Application No. 2014509850 filed on behalf of Probiotical S.P.A. Mail Date: Feb. 16, 2016. 5 pages (Japanese original + English translation).
Japanese Patent Office Official Action Summary for Japanese Patent Application No. 2016513453 filed on behalf of Probiotical S.P.A. Mail Date: Jan. 9, 2018. 9 pages (Japanese original + English translation).
Johnson-Henry K.C., et al., "Lactobacillus Rhamnosus Strain GG Prevents Enterohemorrhagic *Escherichia coli* 0157:H7-Induced Changes in Epithelial Barrier Function," Infection and Immunity, Apr. 2008, vol. 76 (4), 9 pages.
Jones et al., "Probiotic Lactobacillus reuteri biofilms produce antimicrobial and anti-inflammatory factors," *BMC Microbiology* 9:35, Feb. 2009 (9 pages).
Kaewnopparat, S., et al. "In vitro probiotic properties of Lactobacillus fermentum SK5 isolated from vagina of a healthy woman", Anaerobe (Aug. 2013), 22, 6-13. 8 pages.
Kanamori Y., et al., "Parenteral and Enteral Nutrition," 2010, vol. 25 (4), 1 pages.
Kanazawa I. "How do neurons die in neurodegenerative diseases?" *Trends Mol Med.*, Aug. 2001, 7 (8): 339-344. Abstract Only. 5 pages.
Karamanolis G., et al., "A Glass of Water Immediately Increases Gastric pH in Healthy Subjects," Digestive Diseases and Sciences, Dec. 2008, vol. 53 (12), 5 pages.
Kaur, B. et al. "Isolation and In vitro characterization of anti-Gardnerella vaginalis bacteriocin producing Lactobacillus fermentum HV6b isolated from human vaginal ecosystem", Int. J. Fundamental Applied Sci. vol. 1, No. 3 (2012):41-50) (10 pages).

(56) References Cited

OTHER PUBLICATIONS

Khavkin A.I., et al., "Modern Principles of Ulcer Disease," retrieved on Mar. 29, 2016, from the internet: URL: www.lvrach.ru/2005/02/4532114/, 6 pages (Russian original+ English translation of relevant parts).

Khryanin et al., "Bacterial Vaginosis: New Prospects in Treatment," *Medical Council* 9:26-32, 2015. (w/ English Machine Translation).

Kim, G.H et al., "The Role of Oxidative Stress in Neurodegenerative Diseases", Exp Nuerobiol., Dec. 2015, 24 (4): 325-340.

Kim H.S., et al., "In vitro Antioxidative Properties of Lactobacilli," Asian-Australasian Journal of Animal Sciences, 2006, vol. 19 (2), 5 pages.

Kim J.W, et al., "Antimicrobial Effect of Bifidobacterium Breve and Bifidobacterium Infantis against *Salmonella typhimurium* KCTC 1925 and *E.coli* 0157:H7 ATCC 43895," Korean Society of Food Science and Technology, Jan. 2002, vol. 11 (1), 4 pages.

Kizerwetter-Swida M., et al., "Selection of Potentially Probiotic Lactobacillus Strains Towards Their Inhibitory Activity Against Poultry Enteropathogenic Bacteria," Polish Journal of Microbiology, 2005, vol. 54 (4), 8 pages.

Klaver F.A.M., et al., "The Assumed Assimilation of Cholesterol by Lactobacilli and Bifidobacterium Bifidum Is Due to Their Bile Salt-Deconjugating Activity," Applied and Environmental Microbiology, Apr. 1993, vol. 59 (4), 1120-1124. 5 pages.

Klemenak, M., et al., "Administration of Bifidobacterium breve Decreases the Production of TNF-a in Children with Celiac Disease," Dig Dis Sci. 60(11):3386-92, 2015. 7 pages.

Korean Office Action for KR Application No. 1020157035288 filed on May 14, 2014 on behalf of Probiotical S.P.A. Mail Date: Aug. 11, 2020 8 pages (English + Original).

Kritsilis et al. Ageing, Cellular Senescence and Neurodegenerative Disease. Int. J. Mol. Sci. (2018);19 (10) :2937. 37 pages.

Krosnynk I.I., et al., "Pharmaceutical Technology: Technology of Dosage Forms: A Textbook for University Students," Academia Editorial Center, 2006, 3 pages (Russian Original+ English Translation of Relevant Parts).

Lai, et al., "Lansoprazole For The Prevention of Recurrences of Ulcer Complications From Long-Term Low-Dose Aspirin Use", N Engl J Med. 346 (26) 2002: 2033-2038.

Langendijk, P.S. et al. "Quantitative fluorescence in situ hybridization of *Bifidobacterium* spp. with genus-specific 16S rRNA-targeted probes and its application in fecal samples", App Environ Micrbiol, Aug. 1995, 61 (8): 3069-75.

Lee, Y.K et al. "Handbook of Probiotics and Prebiotics", 2nd edition (2008)—A John Wiley & Sons, Inc., Publication, p. 399. 3 pages.

Lee, Y.K., et al., "Handbook of Probiotics and Prebiotics", Second Edition (2009), John Wiley & Sons, Inc. pp. 4, 5 and 24. 5 pages of English copy.

Li et al., "Systemic Diseases Caused by Oral Infection," *Clin. Microbial. Rev.* 13(4):547-558, Oct. 2000 (12 pages).

Lieske J.C., et al., "Use of a Probiotic to Decrease Enteric Hyperoxaluria," Kidney International, Sep. 2005, vol. 68 (3), 6 pages.

Likotrafiti E., et al., "Molecular Identification and Anti-pathogenic Activities of Putative Probiotic Bacteria Isolated from Faeces of Healthy Elderly Individuals," Microbial Ecology in Health and Disease, 2004, vol. 16 (2-3), 8 pages.

Lin M.Y., et al., "Antioxidative Effect of Intestinal Bacteria Bifidobacterium Longum ATCC 15708 and Lactobacillus Acidophilus ATCC 4356," Digestive Diseases and Sciences, Aug. 2000, vol. 45 (8), 6 pages.

Lin M.Y., et al., "Inhibition of Lipid Peroxidation by Lactobacillus Acidophilus and Bifidobacterium Longum," Journal of Agricultural and Food Chemistry, Sep. 1999, vol. 47 (9), 4 pages.

Liu J.R., et al., "Antioxidative Activities of Kefir," Asian-Australasian Journal of Animal Sciences, 2005, vol. 18 (4), 8 pages.

Losada, M.A., et al., "Towards A Healthier Diet for The Colon: The Influence of Fructooligosaccharides And Lactobacilli On Intestinal Health," Nutrition Research, vol. 22, pp. 71-84. 2002. 14 Pages.

Lu H., et al., "New Development in the Mechanistic Understanding of Peptic Ulcer Diseases," Drug Discovery Today: Disease Mechanisms, Dec. 2006, vol. 3 (4), 7 pages.

Lutgendorff F., et al., "Probiotics Enhance Pancreatic Glutathione Biosynthesis and Reduce Oxidative Stress in Experimental Acute Pancreatitis," American Journal of Physiology. Gastrointestinal and Liver Physiology, Nov. 2008, vol. 295 (5), 11 pages.

Macfarlane S., et al., "Review Article: Prebiotics In The Gastrointestinal Tract," Alimentary Pharmacology & Therapeutics, Sep. 2006, vol. 24 (5), pp. 701-714. 14 pages.

Magistrelli L. et al., "Probiotics May Have Beneficial Effects in Parkinson's Disease: In Vitro Evidence" Frontiers in Immunology, vol. 10 No. 969, May 2019, pp. 1-9.

Malecka M., "Antioxidant Properties of the Unsaponifiable Matter Isolated From Tomato Seeds, Oat Grains and Wheat Germ Oil," Food Chemistry, Nov. 2002, vol. 79 (3), 4 pages.

Marchese A., et al., "Effect of Fosfomycin Alone and in Combination with N-Acetylcysteine on *E. coli* Biofilms," International Journal of Antimicrobial Agents, Oct. 2003, vol. 22 Suppl 2, 6 pages.

Masashi Okamura, "Youkei no Tomo," 2008, vol. 558, 1 pages.

Mathews H.M., et al., "Sodium Bicarbonate as a Single Dose Antacid in Obstetric Anaesthesia," *Anaesthesia*, vol. 44 (7), (Jul. 1989). 2 pages.

Matsubara et al., "Probiotic lactobacilli inhibit early stages of Candida albicans biofilm development by reducing their growth, cell adhesion, and filamentation," Appl Microbial Biotechnol 100:6415-6426 (2016). 18 pages.

Mcfarland, et al. "Strain-Specificity and Disease-Specificity of Probiotic Efficacy: A Systematic Review and Meta-Analysis", Frontiers in Medicine, vol. 5, Article 124, (May 2018), 14 pages.

Mcfarland L.V., "Meta-analysis of Probiotics for the Prevention of Antibiotic Associated Diarrhea and the Treatment of Clostridium Difficile Disease," The American Journal of Gastroenterology, Apr. 2006, vol. 101 (4), pp. 812-822. 11 pages.

Mei X., et al., "Manual of New Drug and Special Drug," Technology Press, 2nd Version, Jan. 2001, 3 pages.

Menotti et al. Epidemiology of Heart Disease of Uncertain Etiology: A Population Study and Review of the Problem. Medicina. (2019); 55:687. 16 pages.

Merriam Webster Definition of "Dose". 1 Page. Accessible online from https://www.merriam-webster.com/dictionary/dose.

Milani C., et al., "Comparative Genomics of *Bifidobacterium animalis* Subsp. *lactis* Reveals a Strict Monophyletic Bifidobacterial Taxon.," Applied and Environmental Microbiology, Jul. 2013, vol. 79 (14), 12 pages.

Modesto M., et al., "Resistance to Freezing and Freeze-drying Storage Processes of Potential Probiotic Bifidobacteria," Annals of Microbiology, Jan. 2004, vol. 54 (1), 6 pages.

Moen S.T., et al., "Testing the Efficacy and Toxicity of Adenylyl Cyclase Inhibitors Against Enteric Pathogens Using in Vitro and in Vivo Models of Infection," Infection and Immunity. Apr. 2010, vol. 78 (4), 10 pages.

Mogna, et al. "Capability of the Two Microorganisms Bifidobacterium breve B632 and Bifidobacterium breve BR03 to Colonize the Intestinal Microbiota of Children", Journal of Clinical Gastroenterology, vol. 48 (1), S37-S39, (Nov. 2014). 3 pages.

Mogna L., et al., "Assessment of the in Vitro Inhibitory Activity of Specific Probiotic Bacteria Against Different *Escherichia coli* Strains," Journal of Clinical Gastroenterology, Oct. 2012, vol. 46 (Supp 1), 4 pages.

Mogna, L., et al., "Screening of Different Probiotic Strains for Their In Vitro Ability to Metabolise Oxalates: Any Prospective Use in Humans?" Journal of Clinical Gastroenterology, 2014, vol. 48, S91-S95). 5 pages.

Mogna L., et al., "In Vitro Inhibition of Klebsiella Pneumoniae by *Lactobacillus delbrueckli* Subsp. *delbrueckil* LDD01 (DSM 22106): An Innovative Strategy to Possibly Counteract Such Infections in Humans?," Journal of Clinical Gastroenterology, Nov.-Dec. 2016, vol. 50 (Supp 2), 4 pages.

(56) References Cited

OTHER PUBLICATIONS

Mohammedsaeed et al., "Lactobacillus rhamnosus GG Inhibits the Toxic Effects of *Staphylococcus aureus* on Epidermal Keratinocytes," Applied and Environmental Microbiology 80(18):5773-5781 (Sep. 2014) (9 pages).

Mueller AA, Saldamli B, Stubringer S, et al. "Oral bacterial cultures in nontraumatic brain abscesses: results of a first-line study." Oral Surg Oral Med Oral Pathol Oral Radial Endod. 2009; 107:469-476. Abstract Only. 1 page.

Murina et al., "Can Lactobacillus fermentum LF10 and Lactobacillus acidophilus LA02 in a Slow-release Vaginal Product be Useful for Prevention of Recurrent Vulvovaginal Candidiasis? A Clinical Study," *J Clin. Gastroenterol.* 48:S102-S105, Nov. 2014.

Mylonas et al., "Cerebral abscess of odontogenic origin," *Journal of Cranio-Maxillofacial Surgery* 35:63-67, 2007.

Nett, J E et al. "Development and validation of an in vivo Candida albicans biofilm denture model." *Infection and Immunity.* Sep. 2010. 78(9 ): 3650-3659. (Year: 2010).

Non-Final Office Action for U.S. Appl. No. 14/113,211, filed Nov. 26, 2013 on behalf of Giovanni Mogna. Mail Date: Apr. 23, 2021. 26 Pages.

Non-Final Office Action for U.S. Appl. No. 14/113,211, filed Nov. 26, 2013 on behalf of Giovanni Mogna. Mail Date: Dec. 7, 2017. 36 pages.

Non-Final Office Action for U.S. Appl. No. 14/113,211, filed Nov. 26, 2013 on behalf of Hoffmann-Eitle Srl. Mail Date: May 29, 2019. 29 pages.

Non-Final Office Action for U.S. Appl. No. 14/116,999, filed Dec. 20, 2013 on behalf of Giovanni Mogna. Mail Date: Jan. 5, 2018, 26 pages.

Non-Final Office Action for U.S. Appl. No. 14/344,021, filed May 9, 2014 on behalf of Giovanni Mogna. Mail Date: Jul. 24, 2017. 18 pages.

Non-Final Office Action for U.S. Appl. No. 15/265,706, filed Sep. 14, 2016 on behalf of Probiotical S.P.A .. Mail Date: Apr. 17, 2019. 27 pages.

Non-Final Office Action for U.S. Appl. No. 15/902,977, filed Feb. 22, 2018 on behalf of Probiotical S.P.A. Mail Date: Oct. 31, 2019. 20 pages.

Non-Final Office Action for U.S. Appl. No. 16/087,609, filed Sep. 21, 2018 on behalf of Probiotical S.P.A. Mail Date: Feb. 27, 2020 9 pages.

Non-Final Office Action for U.S. Appl. No. 16/322,843, filed Feb. 1, 2019 on behalf of Probiotical S.P.A. Mail Date: May 26, 2021 26 pages.

Non-Final Office Action for U.S. Appl. No. 16/368,655 filed on behalf of Probiotical S.p.A. Mail date: Mar. 2, 2020. 22 pages.

Non-Final Office Action for U.S. Appl. No. 16/368,655, filed Mar. 28, 2019, on behalf of Probiotical S.p.A. Mail Date: Apr. 22, 2021. 19 Pages.

Non-Final Office Action for U.S. Appl. No. 16/615,355, filed Nov. 20, 2019 on behalf of Probiotical S.P.A. Mail Date: Nov. 23, 2021 13 pages.

Non-Final Office Action for U.S. Appl. No. 16/624,136, filed Dec. 18, 2019 on behalf of Probiotical S.P.A. Mail Date: Apr. 29, 2021 14 pages.

Non-Final Office Action for U.S. Appl. No. 16/624,136, filed Dec. 18, 2019 on behalf of Probiotical S.P.A. Mail Date: Mar. 1, 2022 37 pages.

Non-Final Office Action for U.S. Appl. No. 16/624,249, filed Dec. 18, 2019 on behalf of Marben S.R.L. Mail Date: May 1, 2023. 16 pages.

Non-Final Office Action for U.S. Appl. No. 16/624,249, filed Dec. 18, 2019 on behalf of Probiotical S.P.A. Mail Date: Apr. 15, 2021 14 pages.

Non-Final Office Action for U.S. Appl. No. 17/230,665, filed Apr. 1, 2021, on behalf of Probiotical S.p.A. Mail Date: Mar. 17, 2023. 35 Pages.

Non-Final Office Action for U.S. Appl. No. 14/891,306, filed Nov. 13, 2015 on behalf of Probiotical S.P.A Mail Date: May 2, 2019 25 pages.

Non-Final Office Action issued for U.S. Appl. No. 16/861,136, filed Apr. 28, 2020, on behalf of Probiotical S.P.A. Mail Date: Apr. 13, 2022. 19 Pages.

Notice of Allowance for U.S. Appl. No. 14/116,996, filed Dec. 18, 2013 on behalf of Giovanni Mogna. Mail Date: Dec. 3, 2020. 11Pages.

Notice of Allowance for U.S. Appl. No. 14/116,996, filed Dec. 18, 2013 on behalf of Giovanni Mogna. Mail Date: Aug. 14, 2020. 10 Pages.

Notice of Allowance for U.S. Appl. No. 14/116,996, filed Dec. 18, 2013 on behalf of Giovanni Mogna. Mail Date: May 6, 2020. 11 Pages .

Notice of Allowance for U.S. Appl. No. 14/116,999, filed Dec. 20, 2013, on behalf of Probiotical S.P.A. Mail Date: Dec. 26, 2018. 14 pages.

Notice of Allowance for U.S. Appl. No. 14/116,999, filed Dec. 20, 2013, on behalf of Probiotical S.p.A. Mail Date: Sep. 4, 2018. 11 pgs.

Notice of Allowance for U.S. Appl. No. 14/117,003, filed Dec. 27, 2013 on behalf of Giovanni Mogna. Mail Date: Nov. 22, 2016. 8 pages.

Notice of Allowance for U.S. Appl. No. 14/117,003. Mail Date: Nov. 24, 2017, 5 pages.

Notice of Allowance for U.S. Appl. No. 14/344,021, filed May 9, 2014 on behalf of Giovanni Mogna. Mail Date: Mar. 27, 2018. 9 pages.

Notice of Allowance for U.S. Appl. No. 14/344,021, filed May 9, 2014 on behalf of Giovanni Mogna. Mail Date: Dec. 15, 2017. 7 pages.

Notice of Allowance for U.S. Appl. No. 14/346,941, filed Mar. 24, 2014 on behalf of Probiotical North America Inc .. Mail Date: Apr. 8, 2019. 29 pages.

Notice of Allowance for U.S. Appl. No. 14/891,306, filed Nov. 13, 2015 on behalf of Probiotical S.P.A. Mail date: Aug. 5, 2020. 9 Pages.

Notice of Allowance for U.S. Appl. No. 14/891,306, filed Nov. 13, 2015 on behalf of Probiotical S.P.A. Mail Date: Jan. 15, 2021. 11 Pages.

Notice of Allowance for U.S. Appl. No. 14/891,306, filed Nov. 13, 2015, on behalf of Probiotical S.P.A. Mail Date: May 19, 2021. 10 Pages.

Notice of Allowance for U.S. Appl. No. 14/891,306, filed Nov. 13, 2015 on behalf of Probiotical S.P.A. Mail Date: May 22, 2020 11 pages.

Notice of Allowance for U.S. Appl. No. 14/891,306, filed Nov. 13, 2015 on behalf of Probiotical S.P.A. Mail date: Jan. 13, 2020. 15 pages.

Notice of Allowance for U.S. Appl. No. 15/902,977, filed Feb. 22, 2018 on behalf of Probiotical S.P.A. Mail Date: May 6, 2021. 6 Pages.

Notice of Allowance for U.S. Appl. No. 15/902,977, filed Feb. 22, 2018 on behalf of Probiotical S.P.A. Mail Date: Jan. 25, 2021. 6 pages.

Notice of Allowance for U.S. Appl. No. 15/902,977, filed Feb. 22, 2019 on behalf of Giovanni Mogna Mail Date: Oct. 13, 2020 17 pages.

Notice of Allowance for U.S. Appl. No. 16/368,655, filed Mar. 28, 2019 on behalf of Probiotical S.P.A. Mail Date: Jan. 31, 2022 11 pages.

Notice of Allowance for U.S. Appl. No. 14/346,941, filed Mar. 24, 2014 on behalf of Probiotical North America Inc. Mail Date: Aug. 6, 2018. 8 pages.

Notice of Allowance (Technical Examination Report) of Sep. 14, 2020, published in Property Journal Sep. 29, 2020 for Brazilian Application No. BR112013028709-8 filed on May 9, 2012 on behalf of Probiotical S.P.A. 5 Pages (Portuguese +partial Eng trans.).

Notice of Allowance for U.S. Appl. No. 14/116,996, filed Dec. 18, 2013 on behalf of Giovanni Mogna. Mail date: Feb. 26, 2020. 10 Pages.

(56) References Cited

OTHER PUBLICATIONS

Notice of Allowance for U.S. Appl. No. 14/116,996, filed Dec. 18, 2013 on behalf of Giovanni Mogna. Mail date: Sep. 24, 2019. 16 pages.
Notice of Allowance for U.S. Appl. No. 15/902,977, filed Feb. 22, 2018 on behalf of Probiotical S.P.A. Mail Date: Apr. 23, 2020. 5 Pages.
Notification of First Office Action for Chinese patent application No. 201910816928.X on behalf of Probiotical S.P.A., mailed on Mar. 3, 2022. Chinese with Eng transl. 14 pages.
Notification of Reexamination for Chinese Application No. CN 201280031191.7 filed on Apr. 18, 2012, on behalf of Mogna Giovanni. Mail Date: Sep. 24, 2021. 18 Pages. CN Original + English Translation.
Notification of Reexamination for Chinese Patent Application No. CN201280022854 in the name of Probiotical S.P.A, Mail Date: Sep. 29, 2018. (Chinese Original + English Translation). 14 pages.
Notification of Reexamination for Japanese Patent Application No. JP2014509850 in the name of Probiotical S.P.A, Mail Date: Feb. 16, 2016. (Japanese Original + English Translation). 5 pages.
Notification of the Second Office Action for Chinese Patent Application No. 201280034204.6 filed on behalf of Probiotical S.P.A. Issue Date: Oct. 21, 2016, 17 pages (Chinese Original + English translation).
Office Action for Japanese Patent Application No. 2016-513453 filed on behalf of Probiotical S.P.A . . . Mail date: Jan. 9, 2018. 10 pages (Japanese Original + English Translation).
Office Action for Japanese Patent Application No. JP2016513455, Mail Date: Jan. 16, 2018, 7 pages (English Translation+ Japanese Original).
Action for Russian Patent Application No. 2015148750/15 filed May 14, 2014 on behalf of Probiotical S.P.A. Mail date: Mar. 5, 2018. 19 pages (Russian English Translation).
Office Action mailed on Feb. 13, 2017 for Chinese Patent Application No. 201280022854.9 filed on May 9, 2012 in the name of Probiotical S.P.A., 12 pages (English+ Chinese).
Office Action mailed on Feb. 15, 2015 for Chinese Patent Application No. 201180070870.0, 15 pages (Chinese original+ English translation),.
Office Action mailed on Mar. 25, 2016 for Chinese Patent Application No. 201280015994.3, 23 pages (Chinese original+ English translation).
Office Action mailed on Nov. 4, 2014 for Chinese Patent Application No. 201280022854.9 filed on May 9, 2012 in the name of Probiotical S.P.A. (English + Chinese), 15 pages.
Okombo J., et al., "Probiotic-Induced Reduction of Gastrointestinal Oxalate Absorption in Healthy Subjects," Urological Research, Jun. 2010, vol. 38 (3), pp. 169-178. 10 pages.
Olson et al., "Biofilm bacteria: formation and comparative susceptibility to antibiotics," *The Canadian Journal of Veterinary Research* 66:86-92, 2002.
Opposition to Ecuadorian Patent Application SP201313082 on behalf of ALAFAR, 2015, 14 pages (Spanish original + English translation).
Ouoba L.I., et al., "Resistance of Potential Probiotic Lactic Acid Bacteria and Bifidobacteria of African and European Origin to Antimicrobials: Determination and Transferability of the Resistance Genes to Other Bacteria," International Journal of Food Microbiology, Jan. 2008, vol. 121 (2), 8 pages.
Ouwehand A.C., et al., "Probiotics: An Overview of Beneficial Effects," Antonie Van Leeuwenhoek, Aug. 2002, vol. 82 (1-4), 279-289. 11 pages.
Parahitiyawa et al., "Microbiology of Odontogenic Bacteremia: beyond Endocarditis," *Clinical Microbiology Reviews* 22(1):46-64, Jan. 2009.

Pascual L., et al., "Vaginal Colonization and Activity of the Probiotic Bacterium Lactobacillus Fermentum L23 in a Murine Model of Vaginal Tract Infection," Journal of Medical Microbiology, 2010, vol. 59 (Pt 3), pp. 360-364. 5 pages.
Patent Certificate for IN Application No. 1949/MUMNP/2013 filed on May 9, 2012 on behalf of Probiotical S.P.A. Grant Date: Feb. 9, 2021 28 pages.
Peng F., et al., "Health Education for Kidney Diseases," Hubel Science & Technology Press, Dec. 31, 2007, p. 102.(Chinese Original + English Translation) 5 pages.
Peran L., et al., "A Comparative Study of the Preventative Effects Exerted by Three Probiotics, Bifidobacterium Lactis, Lactobacillus Casei and Lactobacillus Acidophilus, in the TNBS Model of Rat Colitis," Journal of Applied Microbiology, Oct. 2007, vol. 103 (4), 9 pages.
Perez-Pardo P. et al., "The gut-brain axis in Parkinson's disease: Possibilities for food-based therapies", *European Journal of Pharmacology*, vol. 817, May 2017, pp. 86-95.
Persson et al., "Cardiovascular disease and periodontitis: an update on the associations and risk," *J Clin Periodontol* 35(8 Suppl):362-379, 2008. Abstract Only. 5 pages.
Preliminary office Action for Brazilian Application No. BR112013028709-8 filed on May 9, 2012 on behalf of Probiotical S.P.A. Mail Date: Aug. 13, 2019. 5 Pages (Portuguese and Informal English Translation).
Probiotical, "Our Probiotic Strains," Jan. 1, 2016, URL= http://bart.pl/wpcontent/uploads/2016/11/ceppi_2016_OK.pdf, retrieved Jun. 16, 2017.
Puccio G., et al., "Clinical Evaluation of a New Starter Formula for Infants Containing Live Bifidobacterium Longum BL999 and Prebiotics," Nutrition, Jan. 2007, vol. 23 (1), 8 pages.
Quanjer, Philip H. et al., "GLI-2012 All-Age Multi-Ethnic Reference Values for Spirometry", 2012. 15 pages.
Rada V., et al., "Susceptibility of Bifidobacteria to Lysozyme as a Possible Selection Criterion for Probiotic Bifidobacterial Strains," Biotechnology Letters, Mar. 2010, vol. 32 (3), 5 pages.
Rada V., et al., "Susceptibility of Bifidobacteria to Nisin," Letters in Applied Microbiology, Feb. 1998, vol. 26 (2), 3 pages.
Rao, R.K. et al. 2013. Protection and restitution of gut barrier by probiotics: nutritional and clinical implications. *Current Nutrition & Food Science* 9(2): 99-107; pp. 1-15; specif. pp. 1, 3.
Reale, M. et al. 2009. Peripheral cytokines profile in Parkinson's disease. *Brain, behavior, and immunity* 23: 55-63; specif. pp. 58, 59.
Restriction Requirement for U.S. Appl. No. 16/322,843, filed Feb. 1, 2019 on behalf of Probiotical S.P.A. Mail Date: Dec. 10, 2020 12 pages.
Restriction Requirement for U.S. Appl. No. 16/368,655, filed Mar. 28, 2019 on behalf of Probiotical S.P.A. Mail Date: Oct. 10, 2019. 7 pages.
Restriction Requirement for U.S. Appl. No. 16/624,249, filed Dec. 18, 2019 on behalf of Probiotical S.P.A. Mail Date: Jan. 19, 2021 8 pages.
Restriction Requirement for U.S. Appl. No. 16/624,249, filed Dec. 18, 2019 on behalf of Probiotical S.P.A. Mail Date: Jan. 19, 2022 5 pages.
Certification Statement and List—37 CFR 1.98(d)(1) filed in U.S. Appl. No. 17/071,947, filed Oct. 15, 2020 on behalf of Probiotical S.P.A. 1 page.
Wikipedia, the free encyclopedia, entry for "Bacteria", through The Wayback Machine, dated Mar. 13, 2017 (31 pages).
Wikipedia, the free encyclopedia, entry for "Candida albicans", through The Wayback Machine, dated Mar. 9, 2017 (7 pages).
Wikipedia, the free encyclopedia, entry for "Gardnerella vaginalis", through The Wayback Machine, dated Jan. 3, 2017 (3 pages).
Wikipedia, the free encyclopedia, entry for "Yeast", through The Wayback Machine, dated Mar. 12, 2017 (16 pages).

\* cited by examiner

Action exerted by LF5 on C. albicans ATCC 90028 during the co-growth of the two microorganisms Inhibition halos of *C.albicans* ATCC 90028 on agar medium induced by a broth culture of the strain LF5: disc technique Inhibition halos of the growth of *C.albicans* ATCC 90028 on agar medium induced by the freeze-dried concentrated of the supernatant of LF5: disc and spot techniques Clinical study for the efficacy and tolerability of LF5 compared with placebo in patients with *Candida albicans*.

Trend of the total average number of symptoms and signs (+ESM) related to the fungal vaginal colonization, during and after treatment with LF5 or miconazole Trend of the total average intensity of symptoms and sign (+ESM) related to the fungal vaginal colonization, during and after treatment with LF5 or miconazole Antimicrobial activity of *Lactobacillus fermentum* LFS against 5 species of *Candida*:
(A) *Candida parapsilosis* (ATCC 22019);
(B) *Candida tropicalis* (ATCC 750);
(C) *Candida krusei* (ATCC 6258);
(D) *Candida glabrata* (ATCC 2001);
and (E) *Candida albicans* (ATCC 10231).
Positive control is represented by one of the *Candida* strain grown alone.

Illustrative histogram of the effect of the co-growth of lactobacilli and C.albicans in MRS Histograms representing the mortality of the different species of Candida co-grown with LF5

Histograms representing the mortality of the different species of Candida co-grown with LF5

Histograms representing the mortality of the different species of Candida co-grown with LF5

Inhibition of C.albicans ATCC 90028: Graphs of overall data

| cfu/ml | 24h | 48h | LF6/T24 | LF6/T48 | LF7/T24 | LF7/T48 | LF8/T24 | LF8/T48 | DPPMA114/T24 | DPPMA114/T48 |
|---|---|---|---|---|---|---|---|---|---|---|
| C. albicans ATCC 90028 | 100×10³ | 10×10³ | 14×10³ | 21×10³ | 14×10³ | 55×10⁴ | 131×10³ | 1×10⁴ | 232×10³ | 25×10³ | 83×10³ |
| C. albicans ATCC 10231 | 55×10³ | 5×10³ | 8×10³ | 78×10³ | 49×10³ | 3×10³ | 78×10³ | 46×10³ | 177×10³ | 357×10³ | 15×10³ |
| C. glabrata ATCC 2001 | 450×10³ | 55×10³ | 79×10³ | 14×10³ | 33×10³ | 15×10⁴ | 47×10³ | 12×10³ | 208×10³ | 13×10³ | 100×10³ |
| C. parapsilosis ATCC 22019 | 100×10³ | 3×10³ | 5,4×10³ | 12×10³ | ¹⁷ | 3×10³ | 207×10³ | 74×10³ | 52×10³ | 28×10³ | 99×10³ |
| C. krusei ATCC 6258 | 162×10³ | 20×10³ | 22×10³ | 13×10³ | 52×10³ | 2×10³ | 29×10³ | 79×10³ | 83×10³ | 8×10³ | 33×10³ |
| C. tropicalis ATCC 750 | 110×10³ | 15×10³ | 18×10³ | 19×10³ | 68×10³ | 1,4×10³ | 10×10³ | 32×10³ | 232×10³ | 67×10³ | 370×10³ |

Experiment 1 continued

FIG. 15

| | cfu/ml | 24h | 48h | Lb2/T24 | Lb2/T48 | ME-3/T24 | ME-3/T48 | LF5/T24 | LF5/T48 |
|---|---|---|---|---|---|---|---|---|---|
| C. albicans ATCC 90028 | 100x10³ | 10x10⁴ | 14x10⁵ | 167x10² | 156x10² | 21x10² | 500x10² | 157x10² | 230x10² |
| C. albicans ATCC 10231 | 55x10³ | 5x10⁴ | 8x10⁴ | 42x10⁴ | 217x10² | 77x10² | 13x10² | 440x10² | 72x10² |
| C. glabrata ATCC 2001 | 450x10³ | 55x10⁴ | 70x10⁴ | 157x10² | 3x10² | 213x10² | 180 | 100x10² | 99x10² |
| C. parapsilosis ATCC 22019 | 100x10³ | 3x10⁴ | 5.4x10⁴ | 347x10² | 60x10² | 200x10² | 1 | 21x10² | 270x10² |
| C. krusei ATCC 6258 | 160x10³ | 20x10⁴ | 21x10⁴ | 38x10² | 28x10⁴ | 11x10⁴ | 42x10⁴ | 62x10⁴ | 99x10⁴ |
| C. tropicalis ATCC 750 | 110x10³ | 15x10⁴ | 18x10⁴ | 5x10⁴ | 55x10⁴ | 270x10² | 10x10⁴ | 15x10⁴ | 30x10⁴ |

Experiment 1
FIG. 15

| | cfu/ml | 24h | 48h | LF09 24h | LF09 48h | LF10 24h | LF10 48h | LF11 24h | LF11 48h | LA02 24h | LA02 48h |
|---|---|---|---|---|---|---|---|---|---|---|---|
| C. albicans ATCC 90028 | 13x10³ | 48x10⁵ | 88x10⁵ | 4660 | 8 | 4000 | 20 | 4480 | 9 | 470000 | 59000 |
| C. albicans ATCC 10231 | 25x10³ | 306x10⁴ | 45x10⁵ | 440 | 2 | 250 | 7 | 520 | 0 | 260000 | 61000 |
| C. glabrata ATCC 2001 | 10x10³ | 12x10⁶ | 34x10⁶ | 6500 | 320 | 12600 | 137 | 61000 | 12 | 2280000 | 1170000 |
| C. parapsilosis ATCC 22019 | 30x10³ | 60x10⁴ | 35x10⁴ | 8900 | 8500 | 2700 | 1100 | 12000 | 1100 | 2600000 | 120000 |
| C. krusei ATCC 6258 | 19x10³ | 66x10⁴ | 27x10⁴ | 7200 | 3400 | 2400 | 900 | 600 | 3 | 2800000 | 1500 |

Experiment 2

FIG. 15

| 24H | C. albicans ATCC 90028 | C. albicans ATCC 10231 | C. glabrata ATCC 2001 | C. parapsilosis ATCC 22019 | C. tropicalis ATCC 750 | C. kruzei ATCC 6258 |
|---|---|---|---|---|---|---|
| LF5 | 99.9843000 | 99.9877778 | 99.9761905 | 99.9790000 | 99.9833333 | 99.9618750 |
| LF6 | 99.7900000 | 99.9980500 | 99.9953333 | 99.9997000 | 99.9881250 | 99.9952632 |
| LF7 | 99.4100000 | 99.9925000 | 99.9950000 | 99.9925000 | 99.9991250 | 99.9989474 |
| LF8 | 99.9900000 | 99.9988500 | 99.9956667 | 99.9981500 | 99.9998000 | 99.9584211 |
| ME-3 | 99.9997900 | 99.9978611 | 99.9994929 | 99.8000000 | 99.9970000 | 99.9931250 |
| DPPMA114 | 99.9791667 | 99.9958000 | 99.9983544 | 99.9972000 | 99.9995533 | 99.9963636 |
| Lb2 | 99.9986083 | 99.9505882 | 99.9998013 | 99.9653000 | 99.9966667 | 99.9872727 |
| LF09 | 99.9990292 | 99.9998860 | 99.9994583 | 99.9851667 | 99.9238095 | 99.9890909 |
| LF10 | 99.9991667 | 99.9999352 | 99.9989500 | 99.9955000 | 99.9823810 | 99.9963636 |
| LF11 | 99.9990667 | 99.9998653 | 99.9949167 | 99.9800000 | 99.9925714 | 99.9990909 |
| LA02 | 99.5833333 | 98.4455959 | 99.9708333 | 99.3333333 | 99.9923810 | 99.8181818 |

| 48H | C. albicans ATCC 90028 | C. albicans ATCC 10231 | C. glabrata ATCC 2001 | C. parapsilosis ATCC 22019 | C. tropicalis ATCC 750 | C. kruzei ATCC 6258 |
|---|---|---|---|---|---|---|
| LF5 | 99.9997500 | 99.9989714 | 99.9997848 | 99.9754545 | 99.9700000 | 99.9238462 |
| LF6 | 99.9998923 | 99.9990200 | 99.9999484 | 99.9999820 | 99.9622222 | 99.9752381 |
| LF7 | 99.9991462 | 99.9984400 | 99.9999266 | 99.9961667 | 99.9944444 | 99.9861905 |
| LF8 | 99.9982154 | 99.9964600 | 99.9996750 | 99.9990370 | 99.9987667 | 99.9614286 |
| ME-3 | 99.9940000 | 99.9998143 | 99.9999961 | 99.9999991 | 99.9900000 | 99.9676923 |
| DPPMA114 | 99.9994813 | 99.9998500 | 99.9998615 | 99.9945000 | 99.9969167 | 99.9845000 |
| Lb2 | 99.9990250 | 99.9978300 | 99.9999962 | 99.9966667 | 99.9508333 | 99.9860000 |
| LF09 | 99.9999991 | 99.9999996 | 99.9999906 | 99.9975714 | 99.9980000 | 99.9987407 |
| LF10 | 99.9999977 | 99.9999984 | 99.9999960 | 99.9996857 | 99.9999991 | 99.9996667 |
| LF11 | 99.9999990 | 100.0000000 | 99.9999996 | 99.9996857 | 99.9986957 | 99.9999989 |
| LA02 | 99.9932955 | 99.9864444 | 99.9655882 | 99.9657143 | 99.9913043 | 99.9994444 |

Experiments on the strains of bacteria *L.Fermentum* with the MICs at 24 and 48 hours

FIG. 16

LACTIC ACID BACTERIAL COMPOSITION FOR THE TREATMENT OF BACTERIAL VAGINAL INFECTIONS BY *GARDNERELLA VAGINALIS* AND, IF PRESENT, OF CONCURRENT FUNGAL INFECTIONS

The present invention relates to a pharmaceutical composition or a composition for a medical device or a composition for a food supplement (briefly, the composition(s) of the present invention) based on lactic acid bacteria belonging to the species *Lactobacillus fermentum* for vaginal and oral use for the simultaneous treatment of vaginal infections, disorders or diseases of fungal and bacterial origin. Specifically, the present invention relates to a said composition comprising pharmaceutical- and/or food-grade excipients and a mixture, which comprises or, alternatively, consists of at least a strain of bacteria belonging to the species *Lactobacillus fermentum* for vaginal and oral use for the simultaneous treatment of vaginal infections, disorders or diseases selected from candidiasis, vaginitis, vulvovaginitis or bacterial vaginosis.

The composition of the intestinal and urogenital microflora is known to represent a critical point for women's health and wellbeing. The vaginal ecosystem consists of epithelial cells lining the vagina and uterus, gland cells secreting in the lumen of the organ and a complex bacterial flora represented by different species of microorganisms.

Such microorganisms are able to fermenting the glycogen deriving from the decomposition of parabasal cells of the eutrophic vaginal mucosa, resulting in the production of lactic acid, the final effect of which is the establishment and maintenance of an acidic vaginal environment (with pH values of approximately 4-4.5 under physiological conditions).

Hydrogen ions ($H^+$) deriving from lactic acid contribute to the formation of hydrogen peroxide. Such a peroxide molecule is toxic for a large number of bacterial species lacking the enzyme catalase. In vaginal secretions, concentrations of about 0.75-5 µg/ml are readily reached, which are more than sufficient for the toxic effect to be exerted. The combined action of hydrogen peroxide, uterine peroxidase (produced by the cervix and endometrium) and chloride ($Cl^-$) and iodide ($I^-$) ions limits the bacterial growth even by directly activating polymorphonuclear cells, which exert a bactericidal action in the epithelial intercellular spaces.

Due to various exogenous and endogenous factors, such as the use of antibiotics, stress conditions, hormonal modulations related to pregnancy, menstrual cycle and/or taking high estrogen concentrations, an unbalance of the vaginal ecosystem often occurs in women. An alteration in the balance of the vaginal ecosystem leads to a prevalence of microorganisms such as *Candida albicans* and *glabrata* and/or *Gardnerella vaginalis*, which cause candidiasis, vaginitis, vulvovaginitis and bacterial vaginosis.

It is known that approximately 75% of women suffered or will suffer, at some point in their life, from at least an episode of vulvovaginal mycosis, due to a fungus (yeast) called *Candida albicans* (*Candida* vaginitis or vulvovaginitis) in 90% of cases. Moreover, it has to be noted that a relapse, namely a further infectious event, occurs in about 40-50% of women.

Furthermore, another important aspect of vaginal infections concerns bacterial vaginosis. A bacterial vaginosis is known to be a vaginal inflammation of bacterial origin and is the most common cause of vaginal disorders in childbearing and menopausal women. Bacterial vaginosis is caused by an alteration in the balance of the vaginal microflora, with abnormal development of commensal germs, which, following to an alteration of the vaginal ecosystem, turn into pathogens due to many causes. The main agent responsible for most of the episodes of bacterial vaginosis, almost 80% of cases, is *Gardnerella vaginalis*. Bacterial vaginosis can be treated with antibiotics such as for example metronidazole or clindamycin. However the bacterial, as well as the fungal vaginosis, can also relapse even after therapy. Therefore, the antibiotic treatment does not represent in any way a definitive treatment, is ineffective in avoiding one or more relapses, nor is a treatment suitable for all the categories of patients.

At present, epidemiological data show that vaginal infections affect more than one billion of women per year worldwide, with serious socio-economic consequences. Furthermore, vaginosis has been related to preterm delivery and a high incidence of necrotizing enterocolitis (NEC). A link between autism and perinatal inflammation has been suggested.

The use of antibiotics during pregnancy has been associated with the onset of asthma.

Vulvovaginal candidiasis (WC) is usually caused by *C. albicans* but it can also be due to other species of *C. albicans* or yeasts. Typical WC symptoms comprise itching, vaginal irritation, dyspareunia, external dysuria and abnormal vaginal secretions. None of these symptoms is VVC-specific.

*C. glabrata* is a pathogenic yeast with various and unique biological characteristics. It could be isolated from the skin and urine, and represents one of the most common yeasts found on mucous membranes. It is considered as an opportunistic pathogen causing surface and systemic infections, in particular in immunocompromised patients. In Europe, the percentage of overall resistance to fluconazole of *C. glabrata* strains is 16.5%.

*C. parapsilosis* is an exogenous pathogen. It can lead to sepsis, onychomycosis and dermatomycosis, is found also in mucosae, and has biochemical characteristics different from the other species.

*C. tropicalis* is the most common pathogen of the genus *Candida*. It is found in mixed cultures along with *C. albicans* and is very resistant to antifungal therapies. This pathogen can proliferate on mucous membranes and can be observed even in the absence of specific signs of a disease.

*C. krusei* is a fungus naturally resistant to fluconazole, and can be isolated from beer, milk and derivatives, and skin, saliva and feces from animals. It is related to some forms of infantile diarrhea and occasionally to systemic diseases. Such a fungus is able to colonizing the intestine, the respiratory and urinary tracts of patients with granulocytopenia.

Bacterial vaginosis (BV) is a clinical polymicrobial syndrome due to the replacement of the normal lactobacilli capable to produce hydrogen peroxide by high concentrations of anaerobic bacteria (e.g. the species *Prevotella* and *Mobiluncucus*), ureaplasma, mycoplasma and several and annoying kinds of anaerobic organisms. Among women in need of treatment, BV is the main cause of vaginal secretions and odor. However, in a study conducted in USA, most of women with BV were found to be asymptomatic. The percentage of women, which experienced at least an episode of BV ranges between 5 and 70%. BV is characterized by the *Gardnerella vaginalis* infection in 80% of reported cases.

After a gynecological diagnosis subsequent to a laboratory fungal analysis, an antibiotic and/or fungicidal therapy is generally chosen, which usually leads to good results in the short term, but is unable to prevent recurrent infections, due to the increasing resistance of pathogens. Furthermore, not all the subjects in need of treatment are able to take and tolerate an antibiotic or fungicidal therapy.

Miconazole and fluconazole represent the most used active ingredients for treating candidiasis: miconazole is mainly used topically for infections due to *C. albicans* and species other than *C. albicans*. Among triazoles, fluconazole is the molecule of choice for the treatment of candidiasis, but its efficacy is variable: in fact from 29% to 43% of patients with systemic infections obtain no satisfactory results with these molecules. In addition, these molecules have a highly variable effectiveness against different species of yeasts.

It is also known the use of microorganisms, such as for example lactic acid bacteria, able to restoring a proper composition of the vaginal microflora. Lactic acid bacteria can be used as active ingredient in a composition for vaginal use, which can be for example in a solid form as an oral tablet, lozenge, granules or powder or solid form as a vaginal tablet or in a liquid form as a vaginal douche, solution or gel.

However, thus far, there is still a need for having a fast and effective treatment against vaginal infections, disorders or diseases independent from a gynecologic diagnosis and microbiological analyses, in order to achieve rapid and beneficial results from the treatment of a bacterial vaginosis and/or *Candida* vaginitis. Basically, it would be very useful to provide a treatment, which, for its application, does not need a diagnosis, which would imply for the patient to be subjected to medical examinations and sample withdrawals, is devoid of side effects typical of the commonly used antibiotics/antifungal drugs, avoids the development of cross-resistance to antibiotics and is highly tolerable and effective.

Specifically, there is still a need for having a composition for vaginal and oral use for the simultaneous treatment of vaginal infections, disorders or diseases of fungal and bacterial origin which is (i) effective and/or (ii) easy to prepare and/or (iii) able to definitively act on the balance of the vaginal ecosystem and/or (iv) effective in avoiding one or more relapses and suitable for all the categories of patients, said composition having a broad-spectrum activity against pathogenic microorganisms among which, but not limited to, yeasts of the genus *Candida*, responsible for fungal candidiasis, vaginitis and vulvovaginitis, and the bacterium *Gardnerella vaginalis*, which accounts for 80% of cases of bacterial vaginosis.

Furthermore, there is still a need for having a composition for vaginal and oral use for the simultaneous treatment of vaginal infections, disorders or diseases of fungal (namely, due to fungi and/or yeasts) and bacterial origin, which represents a valid alternative to an antibiotic and/or fungicidal therapy and, at the same time, represents an effective treatment relative to the known administration forms against both *Candida* and *Gardnerella vaginalis* infections.

The Applicant, after an extended and demanding research and development activity, developed a composition for vaginal or oral use based on lactic acid bacteria being able to effectively solve the common problems of the known technique.

It is an object of the present invention a composition for vaginal or oral use, as set forth in the appended independent claim.

Other preferred embodiments of the present invention are set forth in the appended dependent claims.

FIG. 11 relates to an illustrative histogram of the effect of the co-growth of *lactobacilli* and *C. albicans* in MRS.

FIG. 12 relates to histograms representing the mortality of different species of *Candida* co-grown with LF5.

FIG. 13 relates to histograms representing the mortality of different species of *Candida* co-grown with LF5.

FIG. 14 relates to histograms representing the mortality of different species of *Candida* co-grown with LF5.

FIG. 1 relates to the action exerted by LF5 on *C. albicans* ATCC 90028 during the co-growth of the two microorganisms.

FIG. 2 relates to the inhibition halos of *C. albicans* ATCC 90028 on agar medium induced by a broth culture of the strain LF5: disc technique.

FIG. 3 relates to the inhibition halos of the growth of *C. albicans* ATCC 90028 on agar medium induced by the freeze-dried concentrate of the supernatant from the disc and spot techniques.

FIGS. 4, 5 and 6 relate to the mechanism of action of the strain LF5 against *C. albicans*.

FIG. 15 relates to the inhibition of *C. albicans* ATCC 90028: Graphs of overall data, at experiment 1 and experiment 2.

FIG. 16 relates to experiments on strains of bacteria *L. Fermentum* showing the MICs at 24 and 48 hours.

FIG. 7 shows the results of the clinical study for the efficacy and tolerability of LF5 compared with placebo in patients with *Candida albicans*.

FIG. 8*a* shows the trend of the overall average number of symptoms and signs (+ESM) related to the fungal vaginal colonization, during and after the treatment with LF5 or miconazole.

FIG. 8*b* shows the trend of the total average intensity of symptoms and signs (+ESM) related to the fungal vaginal colonization, during and after the treatment with LF5 or miconazole.

Figure 1:
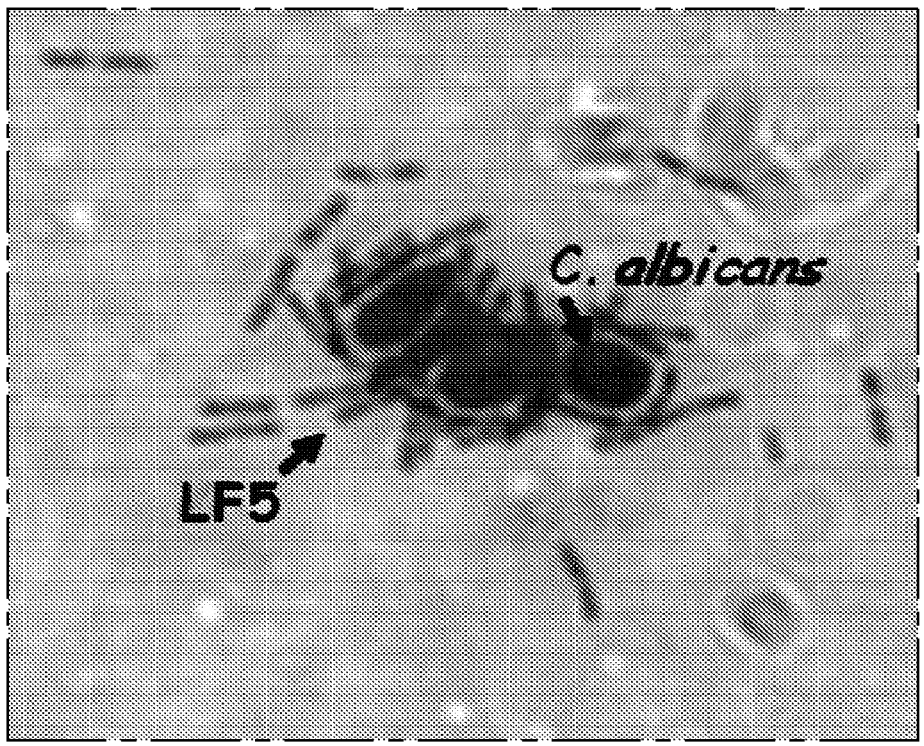

The Applicant carried out a long and intense experimental research activity, during which tested a first group of bacterial strains belonging to the species below:

- *L. plantarum*, such as for example the strain of bacteria *L. plantarum* (LP 01) LMG P-21021;
- *L. pentosus*, such as for example the strain of bacteria *L. pentosus* (LPS 01) DSM 21980;
- *L. delbrueckii* ssp. *delbrueckii*, such as for example the strain of bacteria *L. delbrueckii* ssp. *delbrueckii* (DSMZ 20074 LDD01) DSM 22106;
- *L. rhamnosus*, such as for example the strain of bacteria *L. rhamnosus* (LR 06) DSM 21981;
- *B. breve*, such as for example the strain *B. breve* (BR 03) DSM 16604.

Said bacterial strains were tested in order to assess the inhibition data on *Gardnerella vaginalis* (responsible for 80% of cases of bacterial vaginosis in women) as well as the activity and efficacy thereof against *Candida albicans*. The results of said inhibition tests were negative for the pathogen *Gardnerella vaginalis*. The tests came back negative, since none of the tested strains was able to inhibit the pathogen *Gardnerella vaginalis*.

The strain of the pathogen *Gardnerella vaginalis* being used in the tests of the present invention is the type *Gardnerella vaginalis* ATCC 14018, also referred to as *Haemophilus vaginalis*, as reported below: *Gardnerella vaginalis* ATCC® Number: 14018™, Preceptrol® Culture. Organism: *Gardnerella vaginalis* (Gardner and Dukes) Greenwood and Pickett deposited as *Haemophilus vaginalis* Gardner and Dukes. ATCC Medium: 814 GC Medium.

The Applicant then tested a second group of vaginal bacterial strains belonging to the species below:
(i) *L. crispatus*, such as for example the strain of bacteria *L. crispatus* CRL 1266 ID1626 DSM 24439;
(ii) *L. crispatus*, such as for example the strain of bacteria *L. crispatus* CRL 1251 ID1606 DSM 24438;
(iii) *L. paracasei*, such as for example the strain of bacteria *L. paracasei* LPC 08 ID1696 DSM 21718;
(iv) *L. paracasei*, such as for example the strain of bacteria *L. paracasei* CRL 1289 ID1608 DSM 24440;
(v) *L. fermentum*, such as for example the strain of bacteria *L. fermentum* LF 11 ID1639 DSM 19188.

TABLE 1

| | Amount of fresh MRS | | | | |
| --- | --- | --- | --- | --- | --- |
| | 0 | 0.5 | 1 | 2 | 4 |
| *G. vaginalis* | 0.497 | 1.251 | 1.534 | 1.811 | 1.807 |

| Neutralized supernatant | Amount of supernatant | | | |
| --- | --- | --- | --- | --- |
| of the strain: | 0.5 | 1 | 2 | 4 |
| *L. crispatus* CRL 1266 ID 1626 DSM 24439 | 0.505 | 0.511 | 0.673 | 1.035 |
| *L. crispatus* CRL 1251 ID 1605 DSM 24438 | 0.531 | 0.444 | 0.422 | 0.491 |
| *L. paracasei* LPC08 ID 1696 DSM 21718 | 0.653 | 1.130 | 1.538 | 1.724 |
| *L. paracasei* CRL 1289 ID 1608 DSM 24440 | / | / | 1.476 | 1.774 |
| *L. fermentum* LF 11 ID 1639 DSM 19188 | / | 0.339 | 0.302 | / |
| Ecocillin INOCULUM | 0.794 | 1.074 | 1.391 | 1.690 |

Table 1 reports the results of the inhibition test (Analytical method infra) of *G. vaginalis* by the strains of vaginal bacteria mentioned above from (i) to (v).

Results in Table 1 refer to the optical density, which was detected at the wavelength $OD_{600}$ after 24 hours of microaerophilic growth. The test was performed with a starting inoculum at 2% from fresh broth culture in TH Broth. It was also observed that adding the MRS medium increased the growth ability of the pathogen.

Then, the Applicant tested a third group of strains of bacteria belonging to the species *Lactobacillus fermentum*, in order to assess the inhibition data on *Gardnerella vaginalis* (responsible for 80% of cases of bacterial vaginosis in women) as well as the activity and efficacy thereof against *Candida albicans* and other yeasts of the genus *Candida*.

The Applicant only selected the strains of bacteria belonging to the species *L. fermentum*, which shown to be active and effective against both the pathogens *Candida albicans* and *Gardnerella vaginalis*.

The results of absorbance $OD_{600}$, at 24 hours and 48 hours, are reported in Table 2 and Table 3, respectively.

TABLE 2

| inhibition test (Analytical method infra) | | | |
| --- | --- | --- | --- |
| | Amount of fresh MRS | | |
| 24 hours | 0.5 | 1 | 2 |
| *Gardnerella vaginalis* | 1.379 | 1.542 | 1.567 |

| | Amount of supernatant | | |
| --- | --- | --- | --- |
| Strain | 0.5 | 1 | 2 |
| No. 1 *L. Fermentum* LF 5 ID 686 DSM 32277 | 0.745 | 0.608 | 0.703 |

TABLE 2-continued

| inhibition test (Analytical method infra) | | | |
| --- | --- | --- | --- |
| No. 2 *L. Fermentum* LF 5 ID 686 CNCM I-789 | 0.745 | 0.608 | 0.703 |
| No. 3 *L. Fermentum* LF 06 ID 1456 | 0.727 | 0.541 | 0.591 |
| No. 4 *L. Fermentum* LF 07 ID 1459 | 0.677 | 0.530 | 0.589 |
| No. 5 *L. Fermentum* LF 08 ID 1460 | 0.681 | 0.583 | 0.717 |
| No. 6 *L. Fermentum* LF 09 ID 1462 | 0.715 | 0.551 | 0.615 |
| No. 7 *L. Fermentum* LF 10 ID 1637 | 0.736 | 0.610 | 0.682 |
| No. 8 *L. Fermentum* LF 11 ID 1639 | 0.683 | 0.725 | 0.688 |
| No. 9 *L. Fermentum* DPPMA 114 ID 1757 | 0.783 | 0.735 | 0.669 |
| No. 10 *L. Fermentum* Lb2 ID 1753 | 0.827 | 0.884 | 0.761 |
| No. 11 *L. Fermentum* LF 15 ID 1852 | 0.765 | 0.628 | 0.723 |
| No. 12 *L. Fermentum* LF 16 ID 1853 | 0.716 | 0.580 | 0.652 |
| No. 13 *L. Fermentum* LF 18 ID 1897 | 0.673 | 0.715 | 0.668 |
| No. 14 *L. Fermentum* LF 25 ID 1956 | 0.775 | 0.648 | 0.733 |

TABLE 3

| inhibition test (Analytical method infra) | | | |
| --- | --- | --- | --- |
| | Amount of fresh MRS | | |
| 48 hours | 0.5 | 1 | 2 |
| *Gardnerella vaginalis* | 1.384 | 1.554 | 1.562 |

| | Amount of supernatant | | |
| --- | --- | --- | --- |
| Strain | 0.5 | 1 | 2 |
| No. 1 *L. Fermentum* LF 5 ID 686 DSM 32277 | 0.574 | 0.337 | 0.233 |
| No. 2 *L. Fermentum* LF 5 ID 686 CNCM I-789 | 0.574 | 0.337 | 0.233 |
| No. 3 *L. Fermentum* LF 06 ID 1456 | 0.617 | 0.463 | 0.435 |
| No. 4 *L. Fermentum* LF 07 ID 1459 | 0.489 | 0.474 | 0.379 |
| No. 5 *L. Fermentum* LF 08 ID 1460 | 0.510 | 0.532 | 0.372 |
| No. 6 *L. Fermentum* LF 09 ID 1462 | 0.797 | 0.759 | 0.374 |
| No. 7 *L. Fermentum* LF 10 ID 1637 | 0.618 | 0.696 | 0.447 |
| No. 8 *L. Fermentum* LF 11 ID 1639 | 0.466 | 0.488 | 0.357 |
| No. 9 *L. Fermentum* DPPMA 114 ID 1757 | 0.499 | 0.588 | 0.473 |
| No. 10 *L. Fermentum* Lb2 ID 1753 | 0.532 | 0.601 | 0.583 |
| No. 11 *L. Fermentum* LF 15 ID 1852 | 0.594 | 0.367 | 0.263 |
| No. 12 *L. Fermentum* LF 16 ID 1853 | 0.588 | 0.676 | 0.427 |
| No. 13 *L. Fermentum* LF 18 ID 1897 | 0.496 | 0.498 | 0.377 |
| No. 14 *L. Fermentum* LF 25 ID 1956 | 0.601 | 0.377 | 0.273 |

Therefore, it is an object of the present invention a pharmaceutical composition or a composition for a medical device or a composition for a food supplement or a composition for a food product (briefly, the composition(s) of the present invention) comprising pharmaceutical- and/or food-grade excipients and a mixture consisting of or, alternatively, comprising at least a strain of bacteria belonging to the species *Lactobacillus fermentum*; said composition being for vaginal or oral use for the treatment of vaginal infections, disorders or diseases selected from candidiasis, vaginitis, vulvovaginitis and/or bacterial vaginosis.

An embodiment of the present invention relates to a pharmaceutical composition or a composition for a medical device or a composition for a food supplement or a composition for a food product (briefly, the composition(s) of the present invention) comprising pharmaceutical- and/or food-grade excipients and a mixture comprising or, alternatively, consisting of at least a strain of bacteria belonging to the species *Lactobacillus fermentum* selected from the group comprising or, alternatively, consisting of the bacterial strains from 1 to 14 (listed in Table 4); said composition being for vaginal or oral use for the treatment of vaginal infections, disorders or diseases selected from candidiasis, vaginitis, vulvovaginitis and/or bacterial vaginosis.

TABLE 4

| List of tested strains | Abbreviation | ID | Deposit_*† | Date of Deposit | Depositor |
|---|---|---|---|---|---|
| No. 1 *L. fermentum* | LF 05 | 686 | DSM 32277 | 18 Mar. 2016 | Probiotical SpA |
| No. 2 *L. fermentum* | LF 05 | 686 | CNCM I-789 | 21 Jul. 1988 | Probiotical SpA |
| No. 3 *L. fermentum* | LF 06 | 1456 | DSM 18295 | 24 May 2006 | Anidral Srl |
| No. 4 *L. fermentum* | LF 07 | 1459 | DSM 18296 | 24 May 2006 | Anidral Srl |
| No. 5 *L. fermentum* | LF 08 | 1460 | DSM 18297 | 24 May 2006 | Anidral Srl |
| No. 6 *L. fermentum* | LF 09 | 1462 | DSM 18298 | 24 May 2006 | Anidral Srl |
| No. 7 *L. fermentum* | LF 10 | 1637 | DSM 19187 | 20 Mar. 2007 | Anidral Srl |
| No. 8 *L. fermentum* | LF 11 | 1639 | DSM 19188 | 20 Mar. 2007 | Anidral Srl |
| No. 9 *L. fermentum* | DPPMA 114 | 1757 | DSMZ 23757 | Jul. 8, 2010 | Giuliani SpA |
| No. 10 *L. fermentum* | Lb2 | 1753 | DSM 16143 | 17 Jan. 2004 | Probiotical SpA |
| No. 11 *L. fermentum* | LF 15 | 1852 | DSM 26955 | 1 Mar. 2013 | Probiotical SpA |
| No. 12 *L. fermentum* | LF16 | 1853 | DSM 26956 | 1 Mar. 2013 | Probiotical SpA |
| No. 13 *L. fermentum* | LF18 | 1897 | DSM 29197 | 30 Jul. 2014 | Probiotical SpA |
| No. 14 *L. fermentum* | LF 25 | 1956 | DSM 32275 | 15 Mar. 2016 | Probiotical SpA |

* *deposited and accepted under the provisions of the Budapest Treaty with the Leibniz Institute DSMZ-German Collection of Microorganisms and Cell Cultures in Braunschweig Germany with the indicated deposit number DSM or the Collection Nationale de Culures of Microorganismes (CNCM) Institut Pasteur 25 28 rue du Docteur Roux 75724 Paris Cedex 15 with the indicated deposit number CNCM An embodiment of the present invention relates to a pharmaceutical composition or a composition for a medical device or a composition for a food supplement or a composition for a food product (briefly, the composition(s) of the present invention) comprising pharmaceutical- and/or food-grade excipients and a mixture comprising or, alternatively, consisting of at least a strain of bacteria belonging to the species *Lactobacillus fermentum*; said composition being for vaginal or oral use for the treatment of a vaginal infection, disorder or disease selected from candidiasis, vaginitis, vulvovaginitis or bacterial vaginosis caused by at least a pathogen selected from the group comprising: *Candida glabrata, Candida parapsilosis, Candida krusei, Candida tropicalis, Gardnerella vaginalis, Trichomonas vaginalis, Neisseria gonorrhoeae, Escherichia coli, Herpes simplex* and *Hemophilus ducreyie*, wherein the bacteria belong to the strain *Lactobacillus fermentum* (LF05) with deposit number DSM 32277 or CNCM 1-789 (depositor Probiotical SpA).

A preferred embodiment of the present invention relates to the pharmaceutical composition or composition for a medical device or composition for a food supplement or composition for a food product (briefly, the composition(s) of the present invention), as defined above, comprising pharmaceutical- and/or food-grade excipients and a mixture which, in addition to the bacteria belonging to the strain *Lactobacillus fermentum* (LF05) with deposit number DSM 32277 or CNCM 1-789 (depositor Probiotical SpA), comprises or, alternatively, consists of at least a strain of bacteria belonging to the species *Lactobacillus fermentum* selected from the group comprising or, alternatively, consisting of the strains of bacteria No. 7, 8, 11, 12, 13 and 14 (listed in Table 4); said composition being for vaginal or oral use for the treatment of vaginal infections, disorders or diseases selected from candidiasis, vaginitis, vulvovaginitis or vaginosis. Advantageously, said at least a strain of bacteria belonging to the species *Lactobacillus fermentum* is selected from the group comprising or, alternatively, consisting of the strains of bacteria No. 8, 11, 13 and 14 (listed in Table 4).

Preferably, in the composition for use as described above, said vaginal infection is selected from candidiasis, vaginitis, vulvovaginitis or bacterial vaginosis due to at least a pathogen selected from the group comprising: *Candida glabrata, Candida parapsilosis, Candida krusei, Candida tropicalis* and *Gardnerella vaginalis*.

Advantageously, the inventors found that the bacteria of the strain *Lactobacillus fermentum* (LF05) with deposit number DSM 32277 or CNCM 1-789 (depositor Probiotical SpA) act against different species of yeasts of the genus *Candida*, as well as against bacteria, such as *Gardnerella vaginalis*, which are the main causes of bacterial vaginitis. In this respect, the bacteria of the strain *Lactobacillus fermentum* (LF05) with deposit number DSM 32277 or CNCM 1-789 can be used for the treatment of disorders due to the concurrent presence of yeasts of the genus *Candida*, among which, inter alia, *Candida albicans*, and bacteria, among which, but not limited to, *Gardnerella vaginalis*.

Advantageously the composition of the present invention is for vaginal or oral use for the treatment of vaginal infections, disorders or diseases due to the association of the pathogens *Candida albicans* and *Gardnerella vaginalis*, in that *Lactobacillus fermentum* (LF05) was found to be active against yeasts, such as *Candida albicans* and, surprisingly, also against *Candida* species other than *albicans*, and the bacterium *Gardnerella vaginalis*.

Advantageously, the composition of the present invention is for vaginal or oral use for the treatment of vaginal infections, disorders or diseases selected from candidiasis, among which fungal candidiasis, vaginitis and bacterial vaginosis.

An embodiment of the present invention relates to a pharmaceutical composition or a composition for a medical device or a composition for a food supplement or a composition for a food product comprising pharmaceuticaland/or food-grade excipients and a mixture comprising or, alternatively, consisting of at least a strain of bacteria belonging to the species *Lactobacillus fermentum*; said composition being for vaginal or oral use for the treatment of at least a vaginal infection, wherein said at least a vaginal infection comprises or consists of bacterial vaginosis, caused by the pathogenic bacterium *Gardnerella vaginalis* and wherein the bacteria belong to the strain *Lactobacillus fermentum* (LF05) with deposit number DSM 32277 or CNCM 1-789 (depositor Probiotical SpA).

Preferably, in the composition of the invention, said mixture further comprises or, alternatively, consists of at least a strain of bacteria belonging to the species *Lactobacillus fermentum* selected from the group comprising or, alternatively, consisting of the strains of bacteria from 3 to 14 below:

| List of tested strains | Abbreviation | ID   | Deposit    | Depositor       |
|------------------------|--------------|------|------------|-----------------|
| No. 3 *L. fermentum*   | LF 06        | 1456 | DSM 18295  | Anidral Srl     |
| No. 4 *L. fermentum*   | LF 07        | 1459 | DSM 18296  | Anidral Srl     |
| No. 5 *L. fermentum*   | LF 08        | 1460 | DSM 18297  | Anidral Srl     |
| No. 6 *L. fermentum*   | LF 09        | 1462 | DSM 18298  | Anidral Srl     |
| No. 7 *L. fermentum*   | LF 10        | 1637 | DSM 19187  | Anidral Srl     |
| No. 8 *L. fermentum*   | LF 11        | 1639 | DSM 19188  | Anidral Srl     |
| No. 9 *L. fermentum*   | DPPMA 114    | 1757 | DSMZ 23757 | Probiotical SpA |
| No. 10 *L. fermentum*  | Lb2          | 1753 | DSM 16143  | Probiotical SpA |
| No. 11 *L. fermentum*  | LF 15        | 1852 | DSM 26955  | Probiotical SpA |
| No. 12 *L. fermentum*  | LF16         | 1853 | DSM 26956  | Probiotical SpA |
| No. 13 *L. fermentum*  | LF18         | 1897 | DSM 29197  | Probiotical SpA |
| No. 14 *L. fermentum*  | LF 25        | 1956 | DSM 32275  | Probiotical SpA |

In a preferred embodiment, said mixture further comprises or, alternatively, consists of at least a strain of bacteria belonging to the species *Lactobacillus fermentum* selected from the group comprising or, alternatively, consisting of the strains of bacteria No. 7, 8, 11, 12, 13 and 14.

In a preferred embodiment, said mixture further comprises or, alternatively, consists of at least a strain of bacteria belonging to the species *Lactobacillus fermentum* selected from the group comprising or, alternatively, consisting of the strains of bacteria No. 8, 11, 13 and 14.

In a preferred embodiment, the composition according to the present invention is for use in the treatment of at least a vaginal infection comprising, in addition to a bacterial infection caused by the pathogenic bacterium *Gardnerella vaginalis*, a vaginal infection, vaginitis, vulvovaginitis or bacterial vaginosis due to at least a pathogen selected from the group comprising: *Candida albicans, Candida glabrata, Candida parapsilosis, Candida krusei, Candida tropicalis, Trichomonas vaginalis, Neisseria gonorrhoeae, Escherichia coli, Herpes simplex* and *Hemophilus Ducreyi*.

In a preferred embodiment, the composition according to the present invention is for use in the treatment of at least a vaginal infection comprising, in addition to a bacterial infection caused by the pathogenic bacterium *Gardnerella vaginalis*, a vaginal infection due to the pathogen *Candida albicans*.

The composition of the present invention can be in a solid form or in a liquid form. As a solid form it can be in the form of powder, granules, tablet or lozenge, whereas as a liquid form it can be in the form of solution, vaginal douche, dispersion or gel.

Preferably, said mixture contains said strains of bacteria at a concentration comprised from $1\times10^8$ to $1\times10^{12}$ CFU/g, preferably from $1\times10^9$ to $1\times10^{11}$ CFU/g.

Preferably, said composition contains said strains of bacteria at a concentration comprised from $1\times10^6$ to $1\times10^{10}$ CFU/g, preferably from $1\times10^7$ to $1\times10^9$ CFU/g.

Preferably, said mixture of bacteria is in said composition in a weight ratio comprised from 1:2 to 1:10, preferably in a weight ratio comprised from 1:3 to 1:5.

The composition of the present invention is for vaginal use and oral use and is effectively applied for the treatments of vaginal infections, disorders or diseases, in that it has a wide-spectrum activity against pathogenic microorganisms such as the microorganism *Candida albicans*, a yeast responsible for candidiasis, vaginitis, vulvovaginitis and the bacterium *Gardnerella vaginalis*, which causes bacterial vaginosis. Said composition can also be useful for vaginal applications for the treatment of vaginal infections, disorders or diseases such as gonorrhea, herpes and chancroid.

The strains of bacteria listed in Table 4 can be in said bacterial mixture either as live or dead bacteria, or in the form of sonicated, tyndallized or freeze-dried bacteria.

In a preferred embodiment, the strains of bacteria belonging to the species *L. fermentum* being present in said bacterial mixture contained in said composition of the present invention are in a coated form with one (single coating) or more (for example double coating) plant materials for lipid coating having a melting point comprised from 30° C. to 80° C., preferably from 40° C. to 60° C.

The composition of the present invention comprises at least a strain of probiotic bacteria belonging to the species *L. fermentum* able to reducing and/or eliminating the presence of pathogenic agents selected from the group comprising: *Candida albicans, Candida glabrata, Candida parapsilosis, Candida krusei, Candida tropicalis, Gardnerella vaginalis, Trichomonas vaginalis, Neisseria gonorrhoeae, Escherichia coli, Herpes simplex* and *Hemophilus ducreyi*.

As an example, in the tablets according to the invention, the strains of bacteria, preferably used in the form of freeze-dried culture having a viable count usually comprised from 10 to 200 billions of colony-forming units (CFU)/gram, are preferably in an amount from 0.5 to 20% w/w, preferably from 1 to 15% w/w, even more preferably from 3 to 10% w/w, relative to the overall weight of the tablet.

In one of the preferred embodiments, in order to enhance the efficacy of the formulations according to the present invention, specific prebiotic components are added to the powdery mixture thus obtaining a symbiotic composition. The prebiotic component is usually a not digestible saccharide material, at least partially soluble in water or aqueous solution, which stimulates the growth and/or activity of one or more strains of probiotic bacteria as described above. Among these prebiotic agents, food fibers are preferred.

Preferably, said prebiotic fiber is selected from the group comprising: fructooligosaccharides (FOS), galactooligosaccharides (GOS), trans-galactooligosaccharides (TOS), xylooligosaccharides (XOS), chitosan oligosaccharides (COS), a-galactosides (such as raffinose and stachyose), pectins, gums, partially hydrolyzed gums, inulin, psyllium, acacia, carob, oat, bamboo fiber, citrus fibers and, in general, fibers containing a soluble and an insoluble portions, with variable ratios each other.

Advantageously, said prebiotic fiber is selected from fructooligosaccharides (FOS), galactooligosaccharides (GOS) and xylooligosaccharides (XOS). These fibers are not exploited by yeasts of the genus *Candida*, thus providing a competitive advantage for the bacterial strains of the composition of the present invention.

Preferably, the prebiotic component is present in the composition in an amount up to 70% w/w, preferably comprised from 5 to 50% w/w, even more preferably from 10 to 30% w/w, relative to the overall weight of the composition.

In a preferred embodiment, the composition according to the invention can contain additional active components, for example vitamins, mineral salts, plant extracts or other compounds with synergistic or complementary effect to that of the microorganism population of the formulations according to the invention.

Preferably, said additional active components are in an amount up to 70 w/w, preferably comprised from 0.5 to 40% w/w, even more preferably from 1 to 20% w/w, relative to the overall weight of the composition.

In an embodiment (E1) the present invention relates to a pharmaceutical composition or a composition for a medical device or a composition for a food supplement or a composition for a food product comprising pharmaceutical- and/or food-grade excipients and a mixture comprising or, alternatively, consisting of at least a strain of bacteria belonging to the species *Lactobacillus fermentum*; said composition being for vaginal or oral use for the treatment of vaginal infections.

In a preferred embodiment (E2), the present invention relates to the composition for use according to embodiment E1, wherein said vaginal infections are selected from candidiasis, vaginitis, vulvovaginitis or bacterial vaginosis.

In a preferred embodiment (E3), the present invention relates to the composition for use according to embodiment E1 or E2, wherein said mixture comprising or, alternatively, consisting of at least a strain of bacteria belonging to the species *Lactobacillus fermentum* selected from the group comprising or, alternatively, consisting of the strains of bacteria from 1 to 14 below:

| List of tested strains | Abbreviation | ID Deposit | Depositor |
|---|---|---|---|
| No. 1 *L. fermentum* | LF 05 | 686 DSM 32277 | Probiotical SpA |
| No. 2 *L. fermentum* | LF 05 | 686 CNCM I-789 | Probiotical SpA |
| No. 3 *L. fermentum* | LF 06 | 1456 DSM 18295 | Anidral Srl |
| No. 4 *L. fermentum* | LF 07 | 1459 DSM 18296 | Anidral Srl |
| No. 5 *L. fermentum* | LF 08 | 1460 DSM 18297 | Anidral Srl |
| No. 6 *L. fermentum* | LF 09 | 1462 DSM 18298 | Anidral Srl |
| No. 7 *L. fermentum* | LF 10 | 1637 DSM 19187 | Anidral Srl |
| No. 8 *L. fermentum* | LF 11 | 1639 DSM 19188 | Anidral Srl |
| No. 9 *L. fermentum* | DPPMA 114 | 1757 DSMZ 23757 | Probiotical SpA |
| No. 10 *L. fermentum* | Lb2 | 1753 DSM 16143 | Probiotical SpA |
| No. 11 *L. fermentum* | LF 15 | 1852 DSM 26955 | Probiotical SpA |
| No. 12 L. fermentum | LF16 | 1853 DSM 26956 | Probiotical SpA |
| No. 13 *L. fermentum* | LF18 | 1897 DSM 29197 | Probiotical SpA |

-continued

| List of tested strains | Abbreviation | ID Deposit | Depositor |
|---|---|---|---|
| No. 14 *L. fermentum* | LF 25 | 1956 DSM 32275 | Probiotical SpA |

In a preferred embodiment (E4), the present invention relates to the composition for use according to embodiment E3, wherein said mixture comprising or, alternatively, consisting of at least a strain of bacteria belonging to the species *Lactobacillus fermentum* selected from the group comprising or, alternatively, consisting of the strains of bacteria No. 1, 2, 7, 8, 11, 12, 13 and 14.

In a preferred embodiment (E5), the present invention relates to the composition for use according to embodiment E4, wherein said mixture comprising or, alternatively, consisting of at least a strain of bacteria belonging to the species *Lactobacillus fermentum* selected from the group comprising or, alternatively, consisting of the strains of bacteria No. 1, 2, 8, 11, 13 and 14.

In a preferred embodiment (E6), the present invention relates to the composition for use according to any one of embodiments E1-E5, wherein said composition is for the treatment of vaginal infections, disorders or diseases due to the pathogens *Candida albicans* and *Gardnerella vaginalis*.

In a preferred embodiment (E7), the present invention relates to the composition for use according to any one of embodiments E1-E6, wherein said composition is in a solid form or liquid form, preferably in the form of powder, granules, tablet, lozenge, solution, vaginal douche, dispersion or gel.

In a preferred embodiment (E8), the present invention relates to the composition for use according to any one of embodiments E1-E7, wherein said mixture contains said strains of bacteria at a concentration comprised from $1\times10^8$ to $1\times10^{12}$ CFU/g, preferably from $1\times10^9$ to $1\times10^{11}$ CFU/g.

In a preferred embodiment (E9), the present invention relates to the composition for use according to any one of embodiments E1-E8, wherein said composition contains said strains of bacteria at a concentration comprised from $1\times10^6$ to $1\times10^{10}$ CFU/g, preferably from $1\times10^7$ to $1\times10^9$ CFU/g.

In a preferred embodiment (E10), the present invention relates to the composition for use according to any one of embodiments E1-E9, wherein said mixture of bacteria is present in said composition in a weight ratio comprised from 1:2 to 1:10, preferably in a weight ratio comprised from 1:3 to 1:5.

Experimental Part

Biological anti-*Candida* spp. activity specific of the strain *L. fermentum* LF5—"in vitro" study.

1. Selection of the Optimal Liquid and Agar Substrate for the growth of microorganisms: *Candida albicans* and *L. fermentum*.

Growth tests for *C. albicans* ATCC 90028 and the strains *L. fermentum* LF5 (Table 5) were conducted on several liquid and agar substrates, under different conditions and for more or less long periods of incubation. The growth was assessed based on the turbidity of the culture medium by reading the absorbance at 560 nm of the cultures themselves, see table 5.

TABLE 5

Growth of C. albicans ATCC 90028 and L. fermentum LF5 on several substrates under various incubation conditions.

| | Candida albicans ATCC 90028 | L. fermentum LF5 |
|---|---|---|
| MRS liquid medium 37° C. aerobiosis | | |
| pH 6 | +++ | +++ |
| pH 5.5 | ++(+) | +++ |
| pH 5 | ++(+) | n.p. |
| pH 4.5 | ++ | n.p. |
| pH 4 | + | n.p. |
| Sabouraud liquid medium 37° C. aerobiosis | | |
| pH 5.5 | +++ | ++(+) |
| pH 5 | +++ | ++ |
| pH 4.5 | +++ | n.p. |
| pH 4 | ++(+) | n.p. |
| Sabouraud agar medium 30° C. | | |
| aerobiosis (spread plating) | +++ | – |
| aerobiosis (inclusion) | +++ | – |
| anaerobiosis (inclusion) | n.p. | – |
| MRS agar medium 30° C. | | |
| aerobiosis (spread plating) | +++ | ++ (48 h ϕ 1 mm) |
| anaerobiosis (spread plating) | +/– | '– (24 h)/+++ (48 h Ø 2 mm) |
| MRS agar medium 37° C. | | |
| aerobiosis (spread plating) | +++ | +++ (24 h Ø 1 mm) |
| aerobiosis (spread plating) | – | +++ (24 h Ø 2 mm) |

Therefore, the following conditions, as the perfect compromise for co-growing the strains *L. fermentum* and *C. albicans* ATCC 90028, were detected:

a) liquid or agar MRS as the growth substrate;
b) 37° C. as the incubation temperature (preferential for *Lactobacillus*);
c) under aerobiosis (a condition observed for a good growth of the yeast).

2. Assessment of the Biological Activity of the Strain *L. fermentum* LF5 Co-Grown With *C. Albicans*

2.1 Assessment of the Biological Activity Against *Candida albicans*

Growth tests in which *Candida albicans* ATCC 90028 was inoculated ($10^4$ cell/ml) in liquid medium inoculated with the strain *L. fermentum* ($10^3$ cell/ml) were established. The inhibition of the yeast induced by the bacterium was assessed by directly counting it in agar medium after 24 and 48 hours of co-growth.

Figure 11:
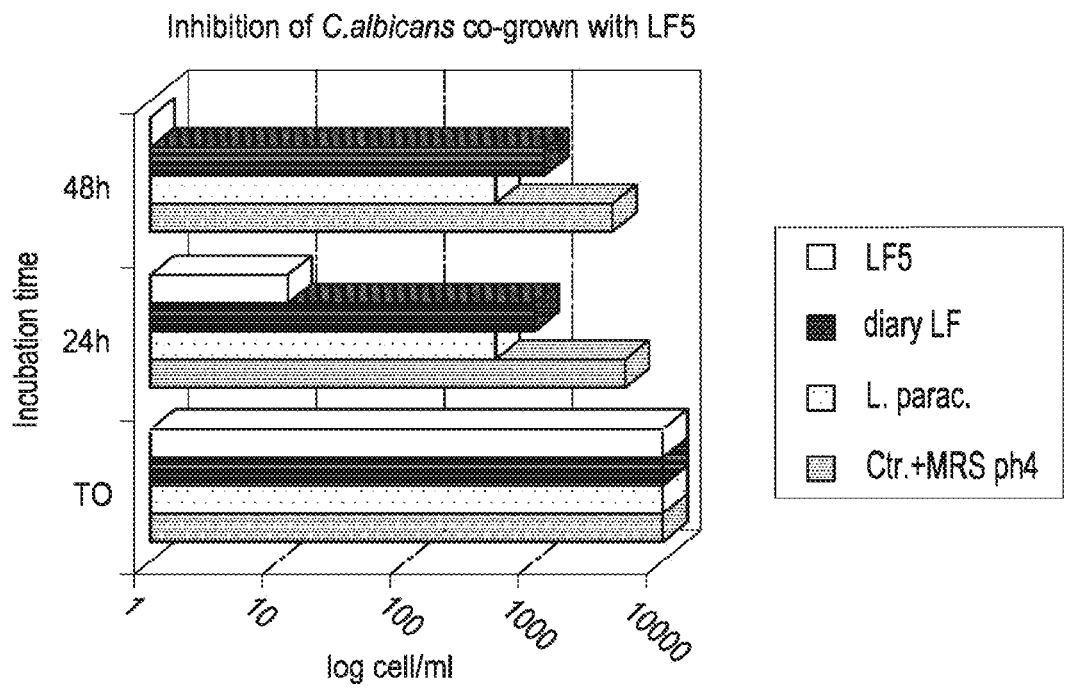

(a) In view of the average of the values from the counts, the strain LF5 (Table 4) can be affirmed to determine an inhibition of *C. albicans* ATCC 90028 equal to 99.9% after 24 hours and 99.999% after 48 hours. Therefore, when the number ratio between inoculated cells of *C. albicans* and *L. fermentum* is 10 to 1 respectively, a $MCB_{99.9}$ after 24 hours of incubation and a $MCB_{99.999}$ after 48 hours of contact are obtained.

b) The specific inhibition, induced by *L. fermentum* LF5 against *C. albicans*, is not equally found in the co-growth of the yeast with other strains of *Lactobacillus*. The number of *Candida* colonies being counted in these samples is in any case lesser than that obtained when growing the yeast alone in MRS. This phenomenon can be ascribed to the spontaneous acidification of the medium occurring during the growth of lactobacilli, as well as definitely to the competition for nutrients and the presence of various catabolic products from lactic acid bacteria. In the substantial inhibition observed for *C. albicans* by *L. fermentum* LF5 and overall quantified above, a specific activity of the strain LF5 takes place, which distinguishes it from other acidifying lactobacilli (FIG. 11).

c) It is further demonstrated that *L. fermentum* LF5 maintains the capability of inhibiting the growth of *C. albicans* in a liquid medium even after several passages in a culture thereof starting from MCB (Master Cell Bank), up to even the eighth sub-culture, it was therefore possible to start the production of the strain LF5 in a pilot plant and then realize the scaling-up at an industrial level. It was then proven the maintenance of the specific activity against the yeast even in the final freeze-dried product.

2.2 Assessment of the Biological Activity Against Other Strains Belonging to the Genus *Candida* spp.

According to the same operating modes as above, co-growth tests for the strain *L. fermentum* LF5 along with other strains of *Candida: Candida glabrata* ATCC 90030, *Candida krusei* ATCC 6258, *Candida parapsilosis* ATCC 22019 were performed.

Figure 12:
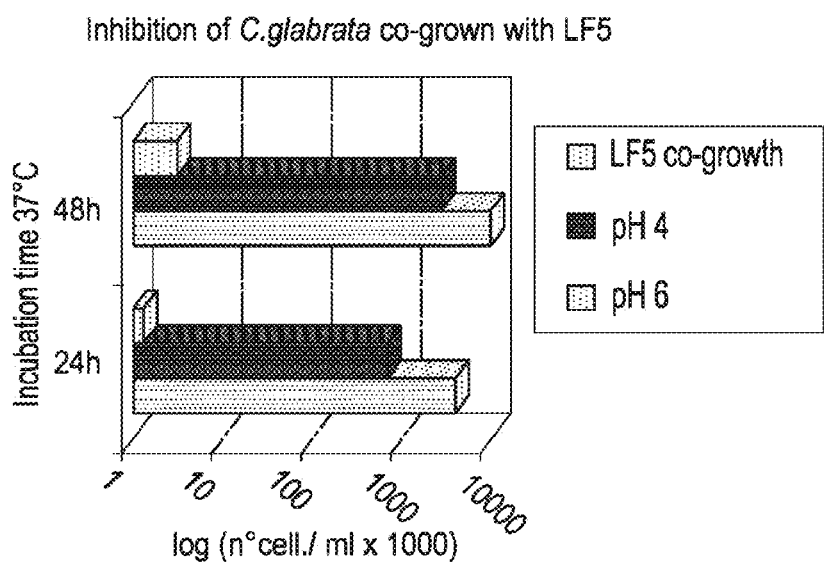
Figure 13:
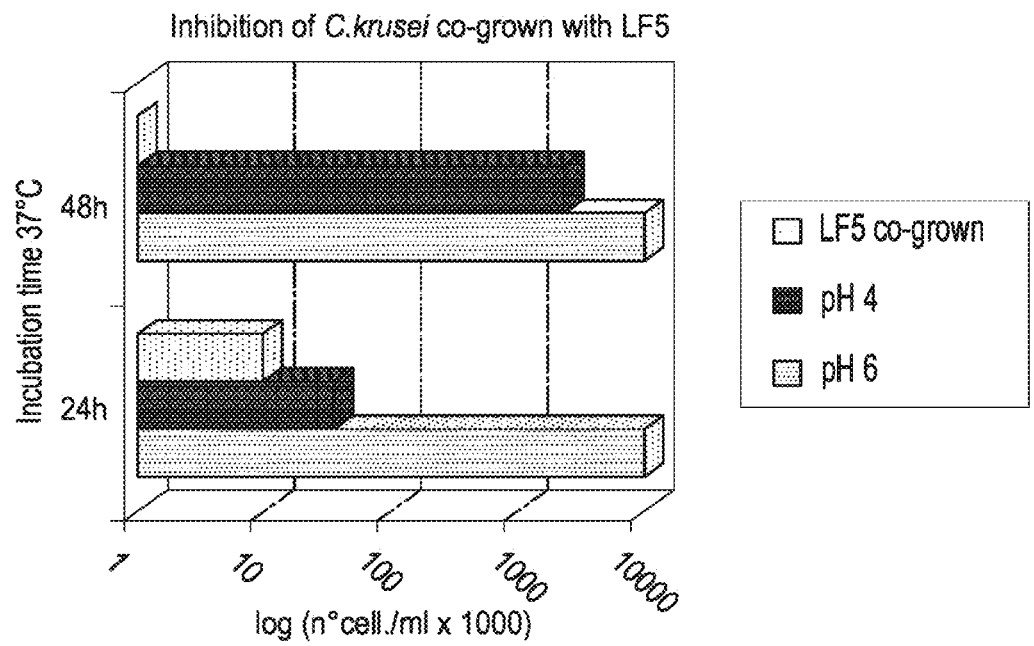
Figure 14:
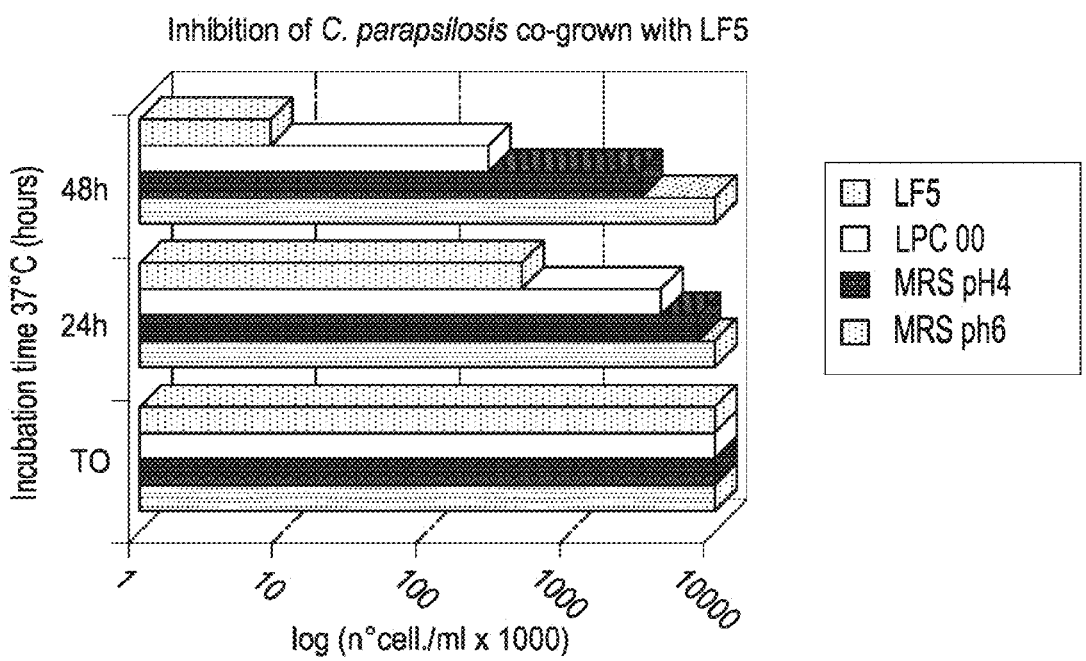
Figure 15:
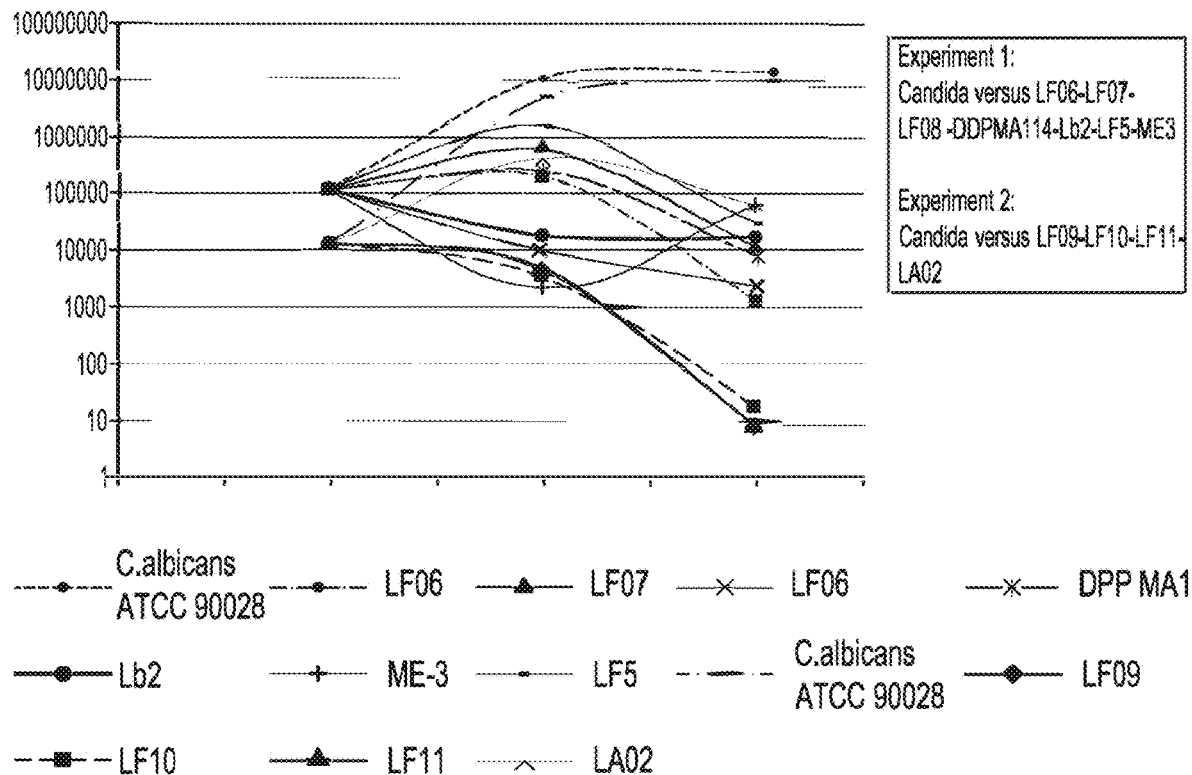

The strain *L. fermentum* LF5 is able to inducing a substantial degree of mortality (FIGS. 12-14), slightly varying according to the species, as well as the conditions under which it is assessed, of the above different strains of *Candida*. On average, an inhibition of about 99.9% during the first 24 hours of incubation is observed, with a mortality reaching 99.99-100% during the 48 hours depending on the given strain. In view of the fact that the species *Candida parapsilosis* and *glabrata* are opportunistic pathogens, which can lead to both infections at the skin surface level, and systemic disorders it can be supposed an application of the strain LF5 as active ingredient for future pharmaceutical formulations, not for systemic use only with urogenital and intestinal efficacy, but also for topical use at the skin surface level.

2.3 Hypothesis for the Possible Mechanism of Action of *L. fermentum* LF5 Against *C. albicans* ATCC 90028

By microscope observation of the co-growth in LF5 and *C. albicans* liquid medium and digital image capture, it was possible to evaluate the action of the *Lactobacillus*, which seems to perform a kind of yeast "opsonization", likely followed by lysis of the membrane through a specific, presumably protein factor bound to the membrane and possibly secreted (FIG. 1).

3. Assessment of the Biological Activity of the Supernatant of Fermentation

Growth tests for *C. albicans* ATCC 90028, inoculated into the fermented broth from LF5 (supernatant) were performed. The supernatant represents the culture medium in which *L. fermentum* LF5 ($10^6$ cell/ml), under optimum conditions for the *Lactobacillus*, was developed and then cell deprived through filtration (Table 6).

TABLE 6

C. albicans ATCC 90028 population after 24- and 48-hour growth in LF5 supernatant, with a positive control represented by the count of Candida inoculated into 10 ml MRS after 24 h (5.7 × 10$^6$ cell/ml).

| | INOCULUM 10000 cell/ml of C. albicans | | | |
|---|---|---|---|---|
| | in 10 ml supernatant | | in 5 ml supernatant + 5 ml MRS | |
| Dilutions | 24 h of growth | 48 h of growth | 24 h of growth | 48 h of growth |
| | 24 h-supernatant harvesting and filtration | | | |
| TQ | 106 | 10 | n.c. | n.c. |
| −1 | 18 | / | n.c. | n.c. |
| −2 | 1 | | About 400 | |
| −3 | / | | 50 | |
| −4 | / | | 5 | |
| | 48 h-supernatant harvesting and filtration | | | |
| TQ | / | / | n.c. | 10 |
| −1 | / | / | 223 | / |
| −2 | | / | / | | a) The "activity" leading to the inhibition of *Candida*, being observed in the co-growth experiments (item 2.1) is maintained in the supernatant, presumably through a specific "factor" released from LF5 even in the culture broth.

b) Such an inhibition activity against the yeast is directly proportional to the concentration of supernatant into which it is inoculated and thus presumably to the concentration of the "factor" released by the *Lactobacillus* in the culture broth (i.e. only supernatant and diluted 1:2 Table 6).

c) This concentration increases during the 48 hours of *L. fermentum* growth (i.e. No. of yeast colonies counted after 24 hours from inoculation, in the 24- and 48-hour supernatant).

d) Given the same concentration, the inhibition activity increases as contacting time increases (i.e. No. of colonies counted in the 24-hour supernatant after 24 and 48 hours of incubation).

e) Specifically, the inhibition induced by the broth fermented by LF5, after 24 hours of incubation and cell deprived through filtration, against *C. albicans* ATCC 90028 is 99.99% at 24 hours and 99.999% at 48 hours. Such an inhibition is due to the specific activity of LF5 as well as definitely to the acidity of the growth substrate into which the yeast (supernatant) is inoculated, and to some nutrient deficiency. In any case, additional inhibition tests for *Candida*, inoculated into the LF5 supernatant, by adjusting the pH and adding glucose and peptone in advance, shown the presence therein of a specific activity, which determines by itself a yeast inhibition of about 96% and 99% at 24 and 48 hours, respectively.

f) The inhibition efficiency of the LF5 supernatant increases when it is sub-cultured in MRS at temperatures greater than 37° C.; in particular 42° C. results to be the optimal condition for producing a higher concentration of the specific anti-*Candida* "factor". Conversely, the growth of LF5 at controlled pH of 5 or 5.5 seems to not affect such a concentration/productivity.

Figure 2:
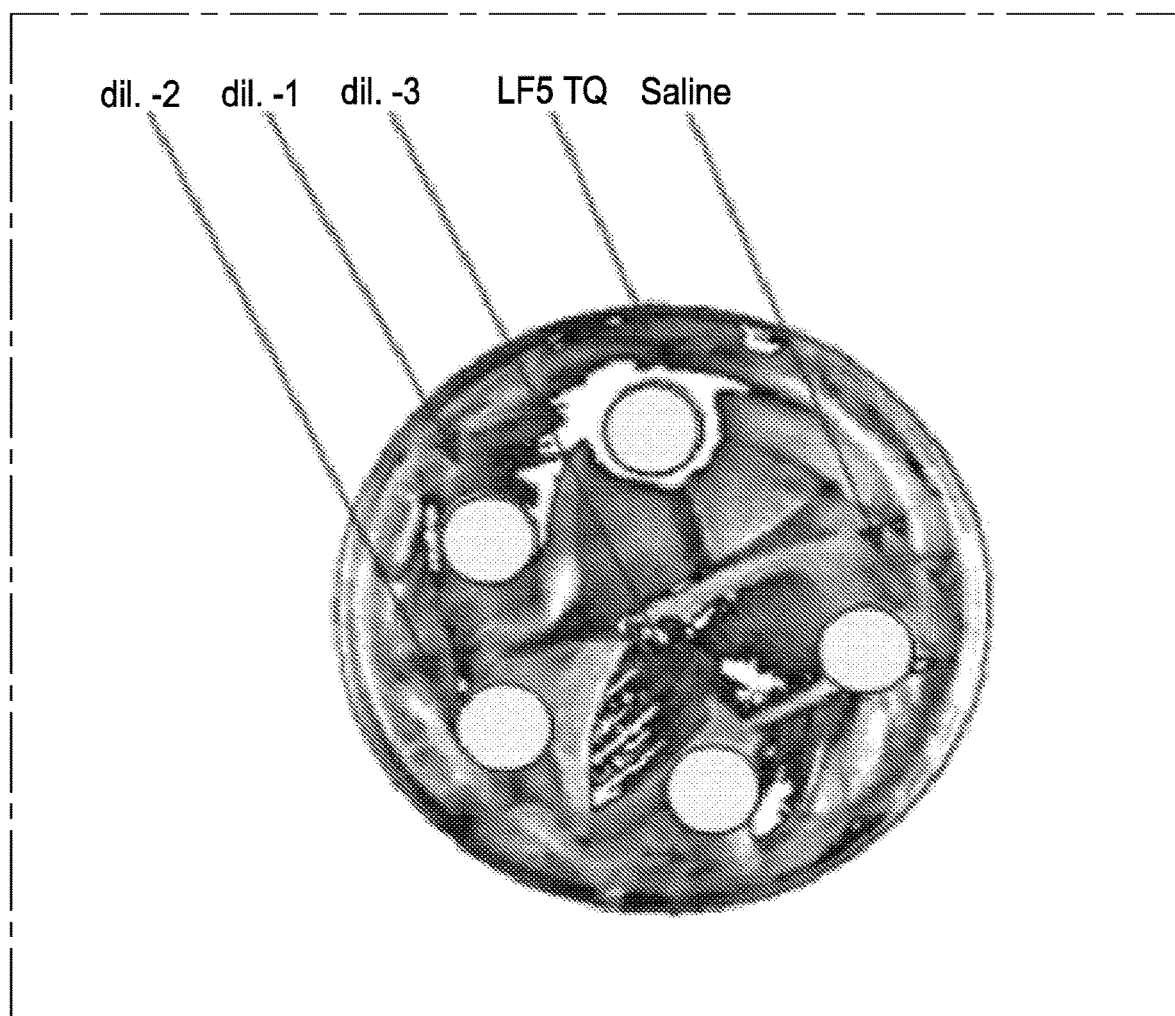
Figure 3:
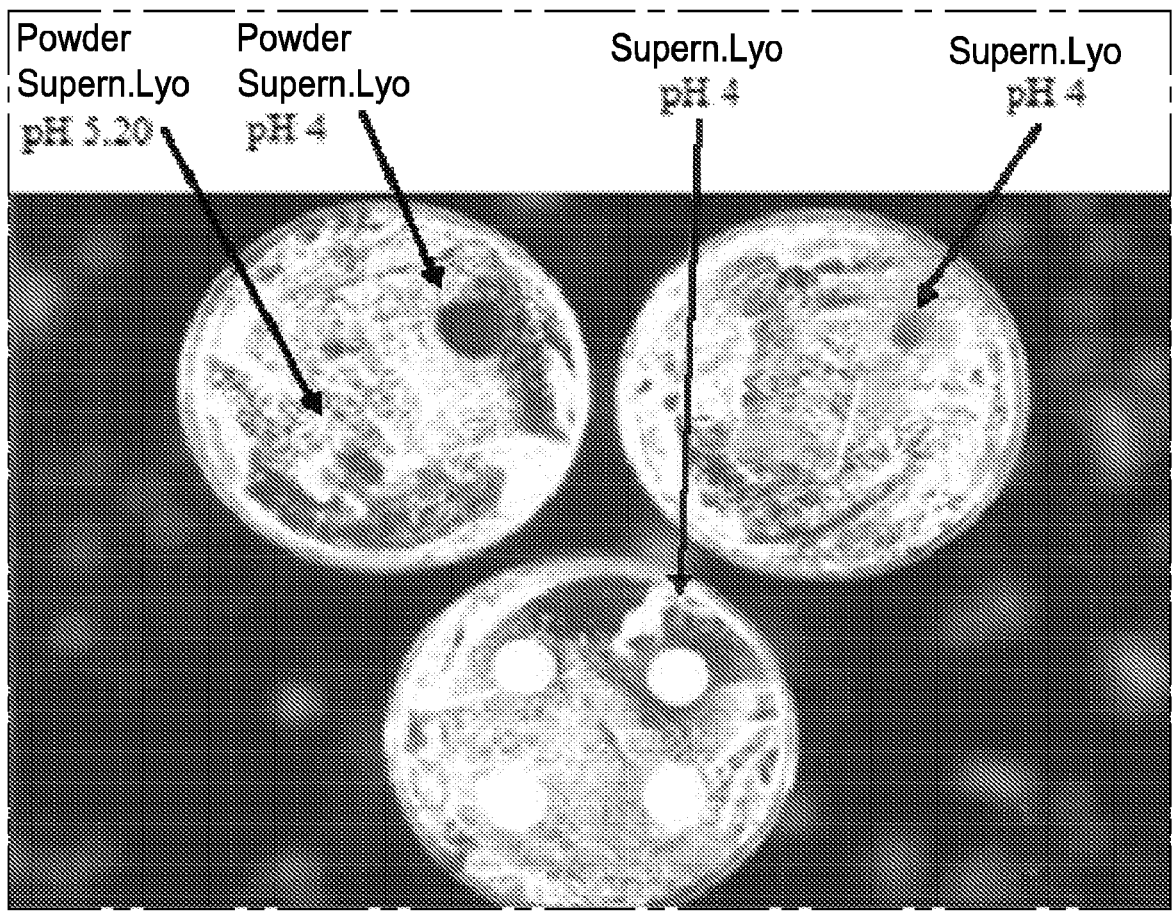
Figure 4:
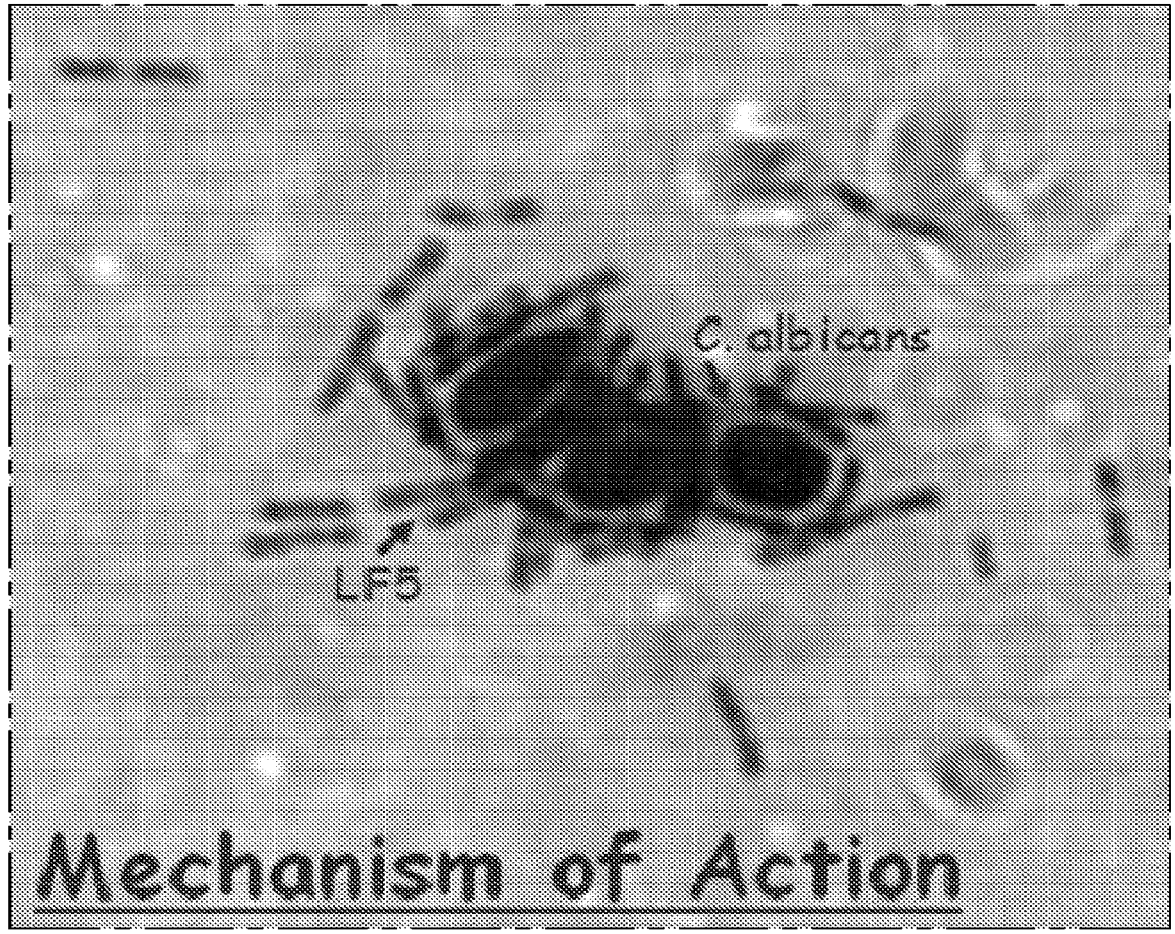
Figure 5:
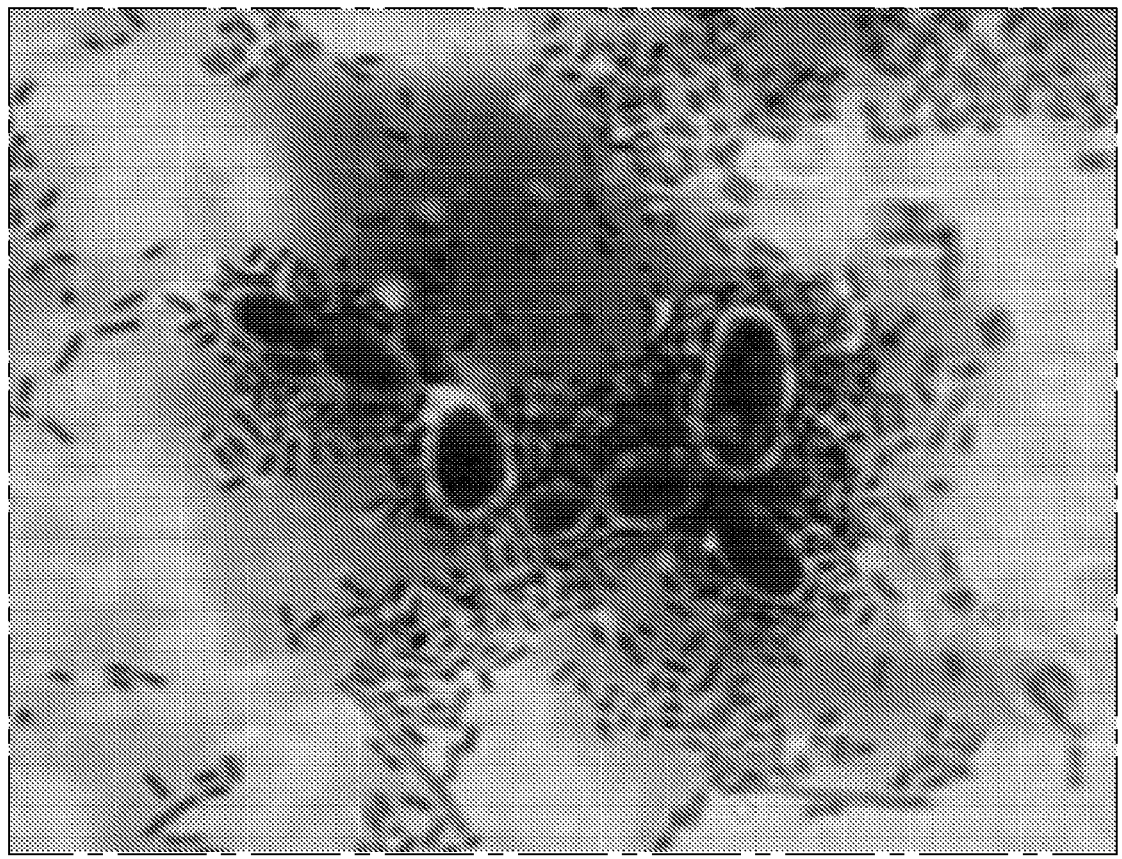
Figure 6:
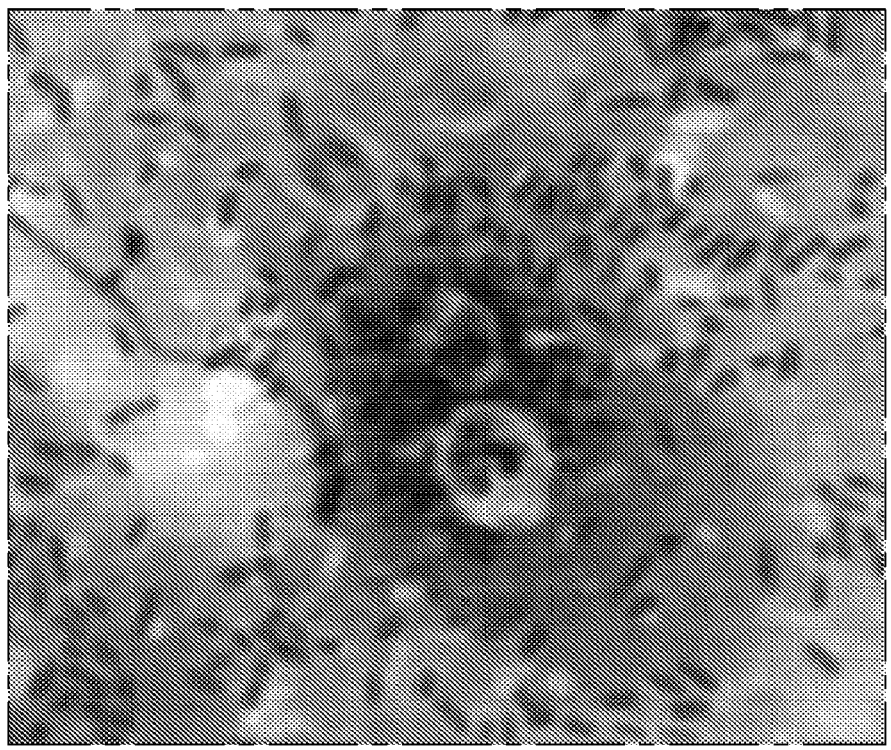

The growth of *C. albicans* ATCC 90028 in agar medium, seeded by spread plating (10$^4$ cells), contacted with the broth culture and LF5 supernatant, deposited on agar by the spot or impregnated disc technique was assessed.

a) In the plates with the disc (FIG. 2) in correspondence of that impregnated with broth culture of LF5 TQ, an inhibition of the *Candida* growth around the disc occurs, with the appearance of a well-detectable halo of about 5 mm from the disc edge.

b) The technique of the impregnated disc, put on agar medium previously spread plated with the yeast, generally leads to a more naked-eye detectable inhibition halo and/or lysis by *L. fermentum*, relative to the spot technique: in the plates with spots, however, within the drop of LF5 TQ, single cells of yeast with not well-defined profiles can be microscopically observed, as if cell debris is present and the area among the cells is dark and inhomogeneous. The condition outside the drop is different, where the yeast cells have well-defined profiles and the agar bottom is clearer and almost homogeneous. What is detectable inside the drop can be ascribed to an inhibition of the yeast growth, with the presence of possible debris due to the lysis, along with *Lactobacillus* cells which grown anyway.

c) The agar tests carried out with discs and/or spots of the supernatant, harvested from a LF5 culture broth, determined no formation of detectable halos probably because of the difficulty for the "factor" with specific activity to spreading into the agar. The freeze-dried and reconstituted supernatant, in order to concentrate, even up to 20 times, such a factor, leads to the occurrence of clear inhibition halos (FIG. 3) with both the disc and spot techniques as well as by directly using the not reconstituted powder (FIG. 4-5-6).

4. Clinical Study for the Efficacy and Tolerability of LF5 Vaginal Capsules Compared With Placebo in Patients with *Candida albicans*

100 patients with vaginitis or vulvovaginitis due to *Candida albicans*, average age of 32.7 years (range 18-64 years) randomly assigned to two groups, which resulted homogeneous, each of 50 patients, treated with placebo o LF5 dosed at 10$^9$ in a vaginal capsule formulation at a dosage of 1 vaginal capsule at night for three consecutive days, according to the experimental double-blind design were treated.

No discontinuations during the treatment nor during the two weeks of post-treatment observation occurred, thus two groups of 50 observations for efficacy and tolerability are provided.

The treatment with LF5 produced microbiological eradication at the end of the three-day treatment in a proportion of patients significantly greater than placebo, along with a very low risk of relapses during the next two weeks. Furthermore, even the symptom remission was significantly greater with LF5 compared with placebo.

Figure 7:
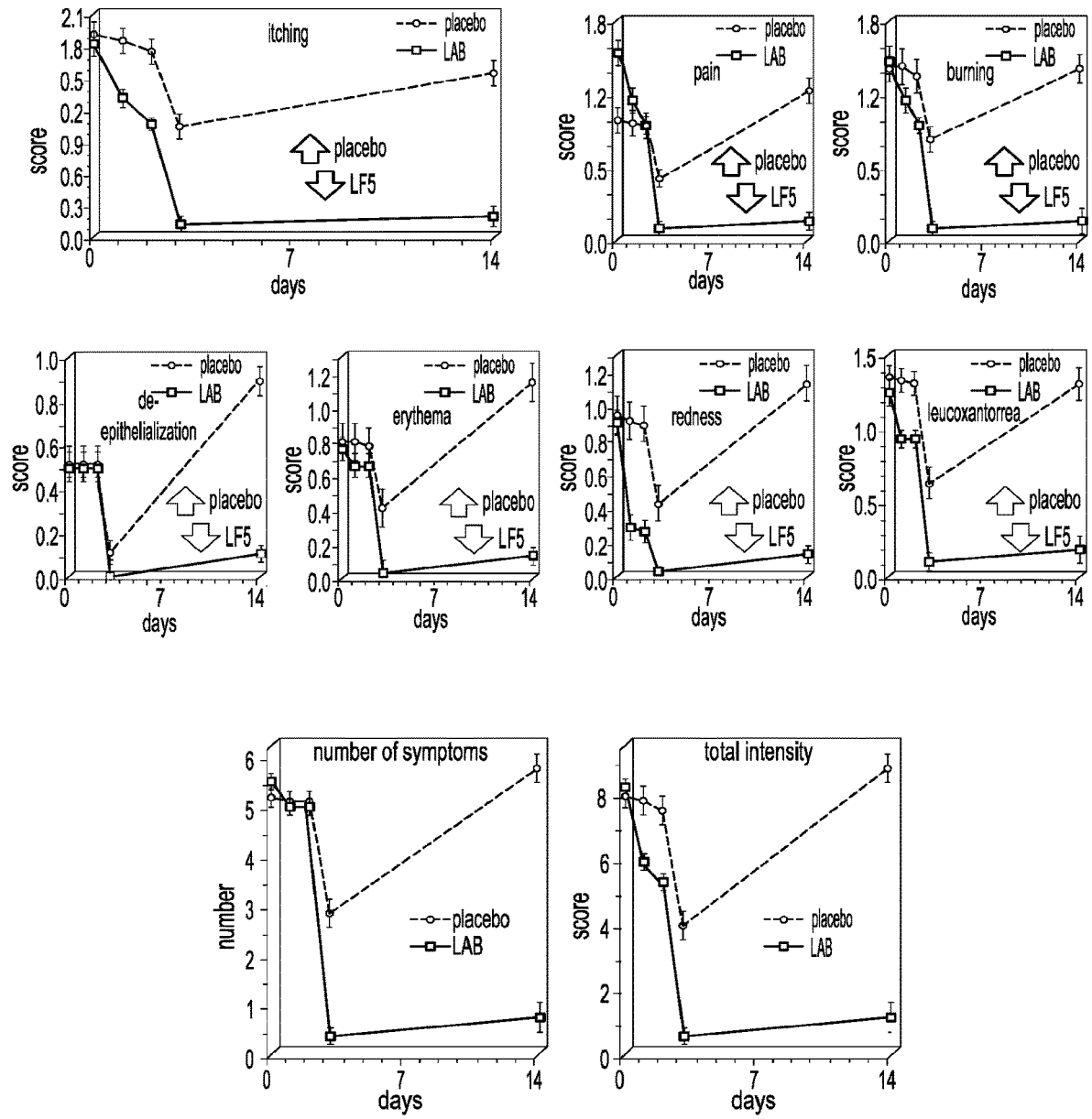

The efficacy data relative to the comparison LF5 vs placebo are reported below in Table 7a and FIG. 7.

TABLE 7a

Results of the study for LF5 efficacy compared with placebo

| Parameter | | Placebo | LAB (LF5) | Statistics |
|---|---|---|---|---|
| Positive/ negative | Baseline | 50/0 | 50/0 | — |
| | 3 Days | 14/36 | 2/48 | 0.002**[1] |
| | Final | 40/10 | 5/45 | <0.001***[1] |
| | Chi square | 164.967 | 122.750*** | |
| Eradication | Failure | 14 | 2 | 44.673***[2] |
| | Relapse | 26 | 3 | |
| | Success | 10 | 45 | |

**P < 0.01;
***0.001
[1]Fisher
[2]Mann-Whitney

TABLE 7b

Patient's opinion about efficacy

| Opinion | Placebo | LAB (LF5) | Mann-Whitney[1] |
|---|---|---|---|
| Excellent | 4 | 42 | 53.322*** |
| Good | 6 | 3 | |
| Acceptable | 26 | 3 | |
| None | 14 | 2 | |

***0.001
[1]Chi-square approximation 4.1 Tolerability Study

The clinical tolerability was good with both the preparations, with 3 cases of poor local reactions with LF5 (6%) and 1 with placebo (2%), with a not statistically relevant difference between the two groups. No clinically relevant changes for peripheral hemodynamics or routine hematology were observed.

The tolerability data relative to the comparison LF5 vs placebo are reported below in Table 7b and FIG. 7.

TABLE 7c

Results of the study for LF5 tolerability compared with placebo

| Opinion | Placebo | LAB (LF5) | Mann-Whitney[1] |
|---|---|---|---|
| Tolerability | | | — |
| Excellent | 49 | 47 | 0.002**[1] |
| Good | 3 | 1 | 1.031 |
| Acceptable | 0 | 0 | |
| None | 0 | 0 | |
| Adverse effects | | | 0.617[2] |
| Present | 1 | 3 | |
| Adverse | 49 | 47 | |

[1]Chi-square approximation
[2]Fisher's exact test

The strain LF5 has an efficacy and tolerability profile in the treatment of vaginal colonization by *Candida albicans* which is definitely favorable and, in any case, significantly more favorable relative to placebo, because of a statistically higher microbiological and clinical efficacy, with the same risk of poor, not clinically relevant local reactions. LF5 in vaginal capsules is thus suggested as a valid alternative to synthetic antifungal drugs for the treatment of vaginal candidiasis.

Examples of Tested Compositions

Composition of LF5 Proprietary Medicinal Products
Each vaginal capsule contains:
Active ingredient:

| Freeze-dried *Lactobacillus Fermentum* No. 1 and 2 (Table 4) Excipients: | NLT $10^9$ CFU |
|---|---|
| Medium-chain triglycerides | 1.964 mg |
| Silica (Aerosil 300) | 36 mg |

Shell composition:

| Gelatin F.U. | 400 mg |
|---|---|
| Glycerol F.U. | 200 mg |
| Dimethylpolysiloxane 1000 | 90 mg |
| Titanium dioxide E 171 | 9 mg |

Each capsule of dermatological oily suspension contains:
Active ingredient:

| Freeze-dried *Lactobacillus Fermentum* No. 1 and 2 (Table 4) | NLT $10^9$ CFU |
|---|---|

Excipients

| Medium-chain triglycerides | 1.964 mg |
|---|---|
| Silica (Aerosil 300) | 36 mg |
| Shell composition: | |
| Gelatin F. U. | 400 mg |
| Glycerol F.U. | 200 mg |
| Titanium dioxide E 171 | 9 mg |
| Dimethylpolysiloxane 1000 | 90 mg |

5 Clinical Study for the Efficacy and Tolerability of LF5 Vaginal Capsules Compared With Miconazole in Patients with *Candida albicans*

100 patients with vaginal candidiasis, average age of 38.0 years (range 19-61 years) randomly assigned to two groups, which resulted homogeneous, each of 50 patients treated with miconazole or LF5 dosed at ≤$10^9$ in vaginal capsule formulation at a dosage of 1 vaginal capsule at night for three consecutive days, according to the single-blind experimental design were treated.

No discontinuations during the treatment nor during the two weeks of post-treatment observation occurred; thus two groups of 50 observations for efficacy and tolerability are provided.

Both the treatments produced, at the end of the three-day treatment, microbiological eradication of *Candida* in almost all the patients (96% vs. 94%). The risk of relapse during the two weeks following to the treatment also resulted very low with both the treatments. However, the relapse risk with miconazole (8/47 patients; 17%) was appreciably higher relative to LF5 (5/48 cases; 10%). The symptom remission was very favorable with both the treatments as well.

The clinical tolerability was good with both the preparations. The frequency of local adverse events, however, was three-fold greater with miconazole (6 cases; 12%) relative to LF5 (2 cases; 4%). No clinically relevant changes for peripheral hemodynamics or routine hematology were observed.

Figure 8A:
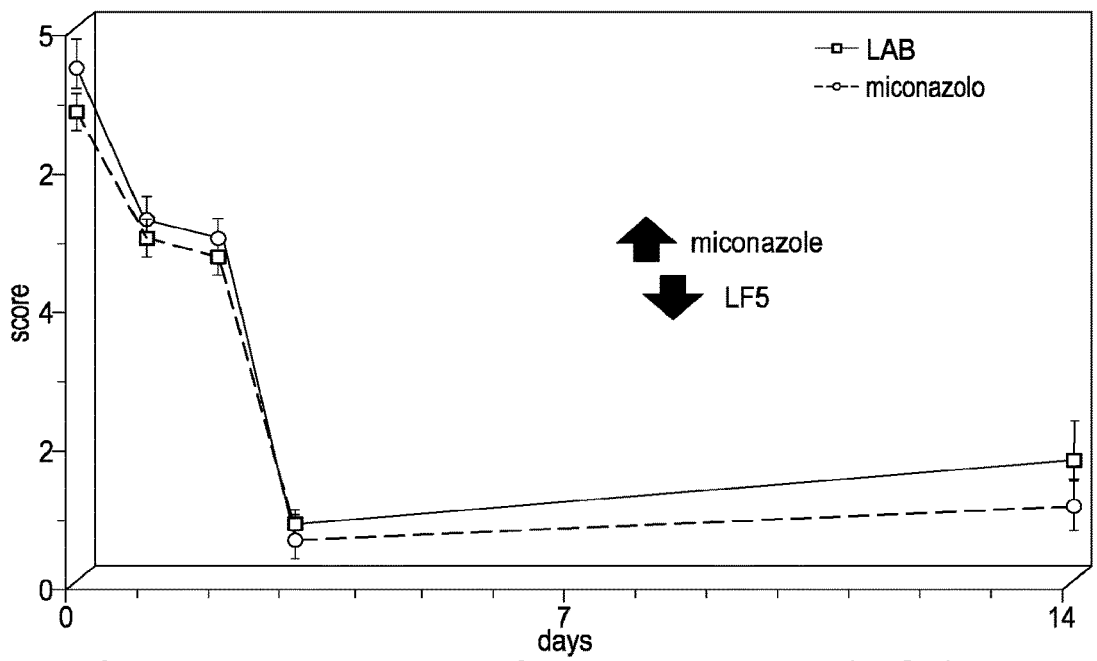
Figure 8B:
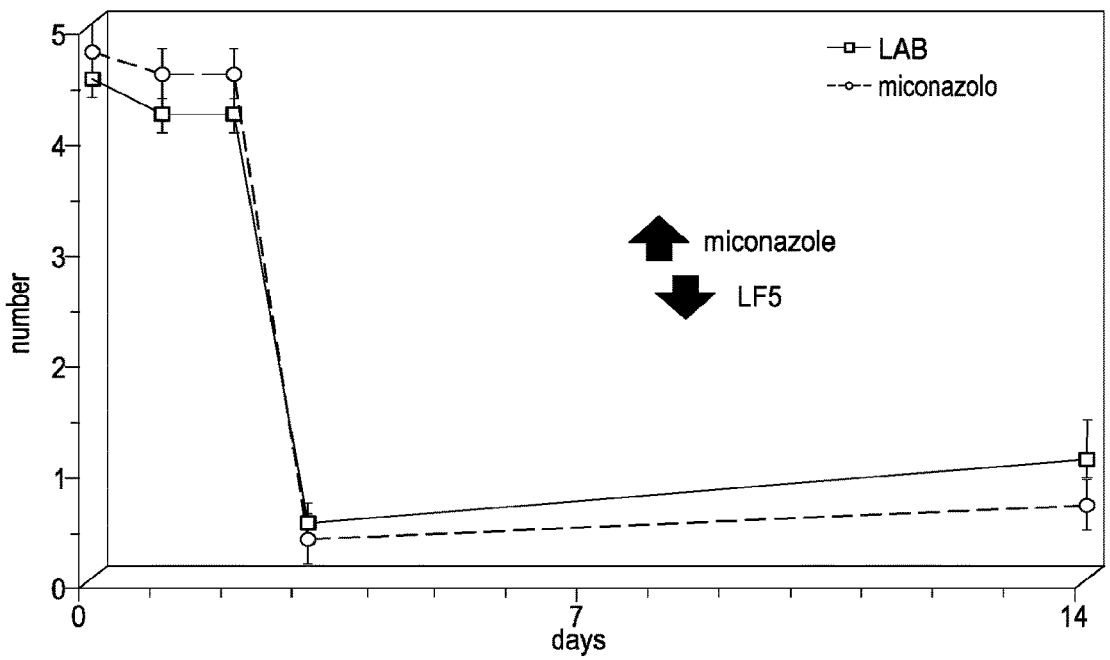

The efficacy data relative to the comparison LF5 vs miconazole are reported below in Table 8a and FIGS. 8*a* and 8*b*.

TABLE 8a

Results of the study for the LF5 efficacy compared with placebo

| Parameter | | LAB (LF5) | Miconazole | Statistics |
|---|---|---|---|---|
| Positive/ | Baseline | 50/0 | 50/0 | — |
| negative | 3 days | 2/48 | 3/47 | 1.000[1] |

TABLE 8a-continued

Results of the study for the LF5 efficacy compared with placebo

| Parameter | | LAB (LF5) | Miconazole | Statistics |
|---|---|---|---|---|
| Eradication | Final | 5/45 | 8/42 | 0.554[1] |
| | Chi square | 122.750 | 110.462*** | |
| | Failure | 2 | 3 | 0.774***[2] |
| | Relapse | 3 | 5 | |
| | Success | 45 | 42 | |

***0.001
[1]Fisher
[2]Mann-Whitney

TABLE 8b

Patient's opinion about efficacy

| Opinion | LAB (LF5) | Miconazole | Mann-Whitney[1] |
|---|---|---|---|
| Excellent | 40 | 38 | 53.322*** |
| Good | 5 | 4 | |
| Acceptable | 3 | 5 | |
| None | 1 | 3 | |

***0.001
[1]Chi-square approximation

The tolerability data relative to the comparison LF5 vs miconazole are reported below in Table 8c.

TABLE 8c

Results of the study for LF5 tolerability compared with miconazole

| Opinion | LAB (LF5) | Miconazole | Mann-Whitney[1] |
|---|---|---|---|
| Tolerability | | | — |
| Excellent | 48 | 44 | 2.148 |
| Good | 1 | 3 | |
| Acceptable | 1 | 3 | |
| None | 0 | 0 | |
| Adverse events | | | |
| Present | 1 | 3 | 0.269[2] |
| Adverse | 49 | 47 | |

[1]Chi-square approximation
[2]Fisher's exact test

In conclusion, LF5 presents an efficacy and tolerability profile in the treatment of vaginal candidiasis, which is definitely favorable and substantially equal, as regards the profile of microbiological and clinical efficacy, to a well-established drug such as miconazole. However, the LF5 tolerability, even without reaching a statistical significance, was highly greater relative to that of the reference drug. Accordingly, LF5 vaginal capsules result a valid alternative to synthetic antifungal drugs for the treatment of vaginal candidiasis.

6 LF5: Study for Local Tolerability and Activity in Patients with *Candida albicans*

100 patients with vaginitis, vulvovaginitis o more extensive *Candida albicans* colonization, average age of 34.0 years (range 17-65 years) with LAB dosed at $\leq 10^9$ in vaginal capsule formulation at a dosage of 1 vaginal capsule at night for 14 consecutive days, according to the open experimental design were treated. No treatment discontinuations occurred, therefore 100 observations for efficacy and tolerability are provided.

The treatment with LF5 produced a microbiological eradication at the end of the first three days of treatment in 92% of patients, and in an additional 5% during the following period of treatment. Overall, only 3% of patients failed the therapy.

During the same observation period, a remarkable remission of the symptoms, in particular during the first three days of treatment was detected as well as, being statistically significant, during the remaining period of observation.

The clinical tolerability was good, with 5 total reports of poor local reactions. No clinically relevant changes in routine hematology were observed.

In conclusion, LF5 has an efficacy and tolerability profile in the treatment of vaginal colonization by *Candida albicans* which is definitely favorable, in that it already has a statistically significant microbiological and clinical efficacy during the first three days of application, with a further improvement when the therapy is continued, without relevant risks of local, always slight, clinically irrelevant and spontaneously reversible adverse reactions, nor detectable risks of alterations of the lab parameters.

Therefore, LF5 vaginal capsules are suggested as a valid alternative to synthetic antifungal drugs for the treatment of vaginal candidiasis, even when it spreads to the proximal structures and in patients with particular conditions such as pregnancy.

Methods

The aim of the method is to verify if a given bacterium is able to inhibit the broth growing of *Gardnerella vaginalis* by the production of substances with bacteriostatic/bactericidal action.

Materials and Reagents

MRS Broth (Difco)
Cysteine chlorohydrate sol. 5% aqueous solution, in sterile pure water. Sterilize through syringe filters 0.22 μm of diameter
THB (Todd Hewitt Broth Sigma-Aldrich)
Peptone saline solution (MET_INT 119-version in force)
NaOH 30%
*Gardnerella vaginalis* ATCC 14018 (Biogenetics)

Sampling and Preparation of the Sample

Preparation of the Inhibitory Strain

Two sequential inoculations of the probiotic bacterium into 15 ml MRS broth (5.1) 0.1% and incubated at 37±1° C. overnight are performed. When the bacterium belongs to the genus *Bifidobacterium* the culture broth is supplemented with 1% cysteine HCl (5.2).

A third inoculation with the same modes, except for a broth amount of 100 ml is carried out.

The incubation is continued up to 30±3 hours.

The broth culture is thus centrifuged and the supernatant separated from cells is brought to pH 6.6±0.2 by adding NaOH conc.

The supernatant is then filtered through 0.2 μm filters and stored at a temperature of 4-5° C.

Preparation of *G. vaginalis*

A pellet of *G. vaginalis* ATCC 14018 is inoculated into 10 ml THB medium supplemented with 1% Cysteine HCl (5.2) and incubated at 37±1° C. overnight.

A sequential inoculation at 1% 37±1° C. overnight is performed.

The fresh broth culture thus prepared is used for the inhibition experiment

Procedure

The sterile tubes being prepared contain:

| THB | 10 ml | 9.5 ml | 9 ml | 8 ml | 6 ml |
|---|---|---|---|---|---|
| MRS | 0 ml | 0.5 ml | 1 ml | 2 ml | 4 ml |
| Bacterial supernatant (7.5) | 0 ml | 0.5 ml | 1 ml | 2 ml | 4 ml |

All the tubes thus prepared are added with 1% Cysteine HCl (5.2).

They are then inoculated at 1% with the fresh broth culture of *G. vaginalis* and incubated at 37±1° C. for 24+24 hours.

At 24 and 48 hours spectrophotometric readings (wavelength A600) by using for each set a blank with the same percentage composition as the two culture broths are conducted.

7. Comparative Study for the Efficacy Relative to Azole Therapies

In view of the above, a combination of *Lactobacillus fermentum* strains was selected in vitro based on the ability thereof to fight different species of *Candida* and then compared with miconazole and fluconazole as regards the inhibition efficacy. Specifically, the possible use of *Lactobacillus* strains as microorganisms for the prophylaxis and/or adjuvant therapy of acute vulvovaginal candidiasis (VVC) and other vaginal infections due to *Candida* yeasts was studied.

Materials and Methods

Strains and Conditions of Bacterial Growth

The strains of *Candida* being used in the present study were purchased from the American Type Culture Collection (ATCC). Specifically, the following biotypes were used: *C. albicans* ATCC 10231, *C. parapsilosis* ATCC 22019, *C. krusei* ATCC 6258, *C. glabrata* ATCC 2001 and *C. tropicalis* ATCC 750 (14). The strains of lactobacilli of this study, all isolated from vaginal swabs of healthy female subjects or directly brushing the intestinal mucosa of healthy humans, were classified based on their phenotypic and genotypic characteristics: *L. fermentum* LF5 (DSM 32277), *L. fermentum* LF09 (DSM 18298), *L. fermentum* LF10 (DSM 19187) and *L. fermentum* LF11 (DSM 19188).

The probiotic strains were cultured overnight in De Man, Rogosa and Sharpe (MRS) medium (Difco, B D, Maryland). In all the experiments, fresh culture media for all the strains of *Candida* were used. Before the experiment, the single strains of *Candida* were cultured in Sabouraud Dextrose Broth (Difco, B D, Maryland), an optimal medium for yeasts, for 48 hours under aerobic conditions.

Every probiotic was then co-cultured in the same broth (MRS) with any one of said *Candida* microorganisms. The ratio between the inoculum of probiotic and yeast was 1:100 in favor of the latter. Incubation was carried out under aerobiosis at 37° C. for 24 hours. Each culture (1 mL) was sampled after 24 hours of incubation for the selective enumeration of the yeasts, conducted on yeast extract glucose chloramphenicol (YGC) agar (Sigma-Aldrich, Milan, Italy). The YGC agar plates were incubated under aerobic conditions at 37° C. for 4 days in order to allow the growth of any present yeast. The colonies were then counted and the results expressed as the number of colony forming units (CFU)/mL.

Evaluation of the fungicidal activity. The minimum inhibitory concentration (MIC) for fluconazole was determined by E-test (bioMerieux Italy, Florence) with MHE agar. The plates were incubated under aerobic conditions at 30° C. and read after 24 hours. Furthermore, since there is no specific E-test for miconazole, the MIC was determined by using the broth macrodilution method. We assessed the activity of serially diluted fluconazole and miconazole (Sigma-Aldrich, Missouri, USA) (from 1 mg/ml to 1 mg/ml) against the *Candida* strains. Serial dilutions of azoles were prepared in Sabouraud Dextrose Broth in the presence of strains of *Candida* and broths were incubated under aerobic conditions at 30° C. and then read at an optical density (DO) of 560 nm. The MIC was defined as the lowest concentration of antibiotic, which completely inhibited the visible growth.

Results

Inhibitory activity of azoles against *Candida* strains. As it can be inferred from tables 8-9, a marked resistance for all the species of *Candida* was detected, except for *C. parapsilosis* ATCC 22019. As regards this biotype, a MIC of 1 mg/ml was obtained, thus confirming the slight sensitivity to fluconazole and miconazole.

TABLE 9

Assessment of the inhibitory activity of miconazole by using a macrodilution test of the culture medium (optical density, OD)

| Miconazole (µg/ml) | C. parapsilosis ATCC 22019 | C. albicans ATCC 10231 | C. tropicalis ATCC 750 | C. krusei ATCC 6258 | C. glabrata ATCC 2001 |
|---|---|---|---|---|---|
| 0 | 1.610 | 1.912 | 1.972 | 1.987 | 2.246 |
| 1 | 1.515 | 1.906 | 1.950 | 1.990 | 2.260 |
| 2.50 | 1.115 | 1.910 | 1.927 | 1.900 | 2.260 |
| 5.00 | 0.975 | 1.901 | 1.908 | 1.893 | 2.246 |
| 50 | 0.894 | 1.905 | 1.846 | 1.994 | 2.239 |
| 250 | 0.701 | 1.916 | 1.942 | 2.004 | 2.212 |
| 300 | 0.415 | 1.889 | 1.937 | 1.999 | 2.215 |
| 500 | 0.314 | 1.863 | 1.903 | 1.988 | 2.213 |
| 1.000 | 0.295 | 1.464 | 1.931 | 1.972 | 2.198 |

TABLE 10

MIC (minimum inhibitory concentration) of fluconazole
from E_test (range 0.016-256 µg/ml).

| Candida species | MIC (µg/ml) |
| --- | --- |
| Candida parapsilosis ATCC 22019 | 1* |
| Candida albicans ATCC 10231 | >256 |
| Candida tropicalis ATCC 750 | >256 |
| Candida krusei ATCC 6258 | >256 |
| Candida glabrata ATCC 2001 | >256 |

*p ≤ 0.05

Antagonistic Effects of L. fermentum Against Candida

Figure 9:
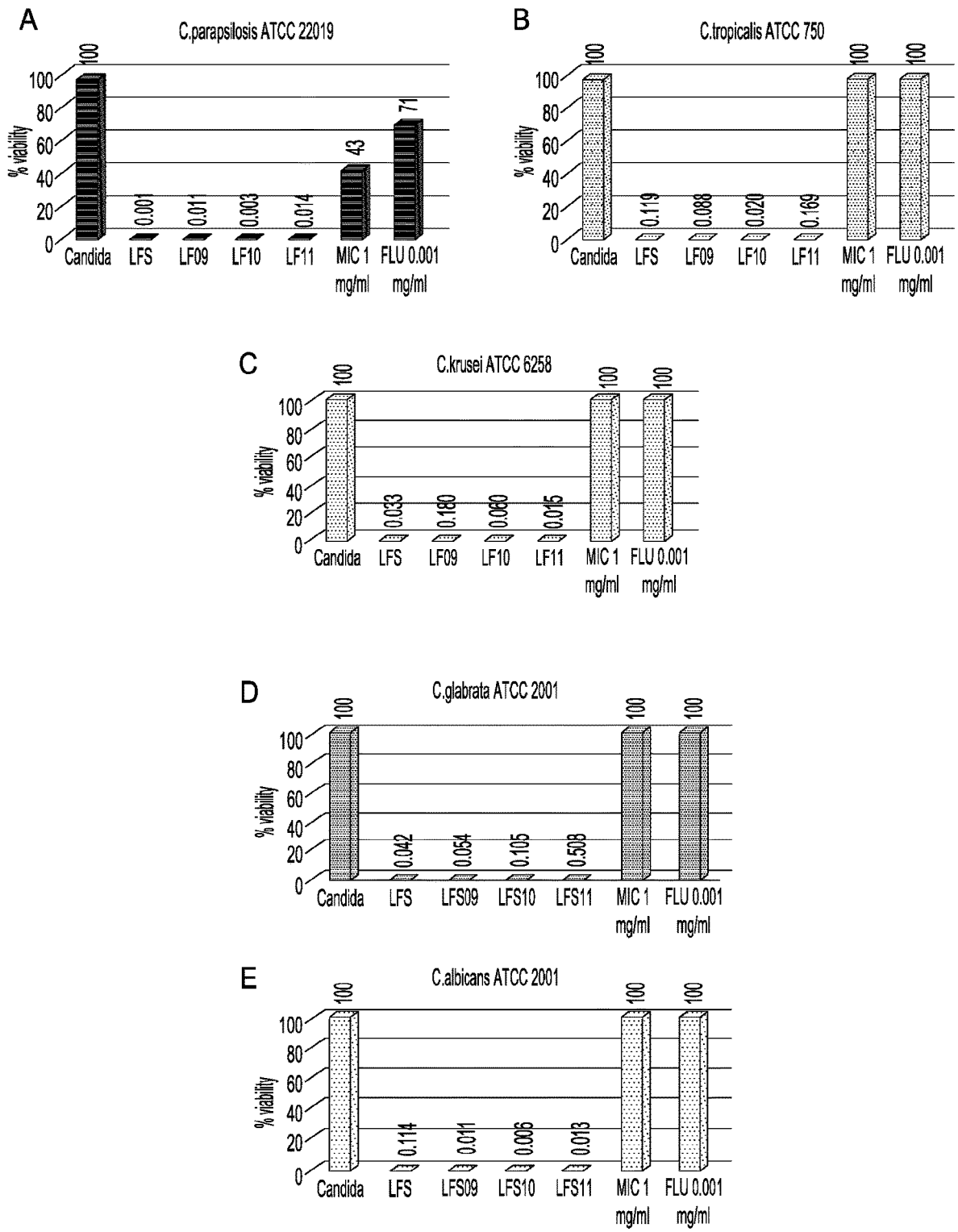
FIG. 9 shows the activity of different strains of *Lactobacillus fermentum* against several species of *Candida*.
Figure 10:
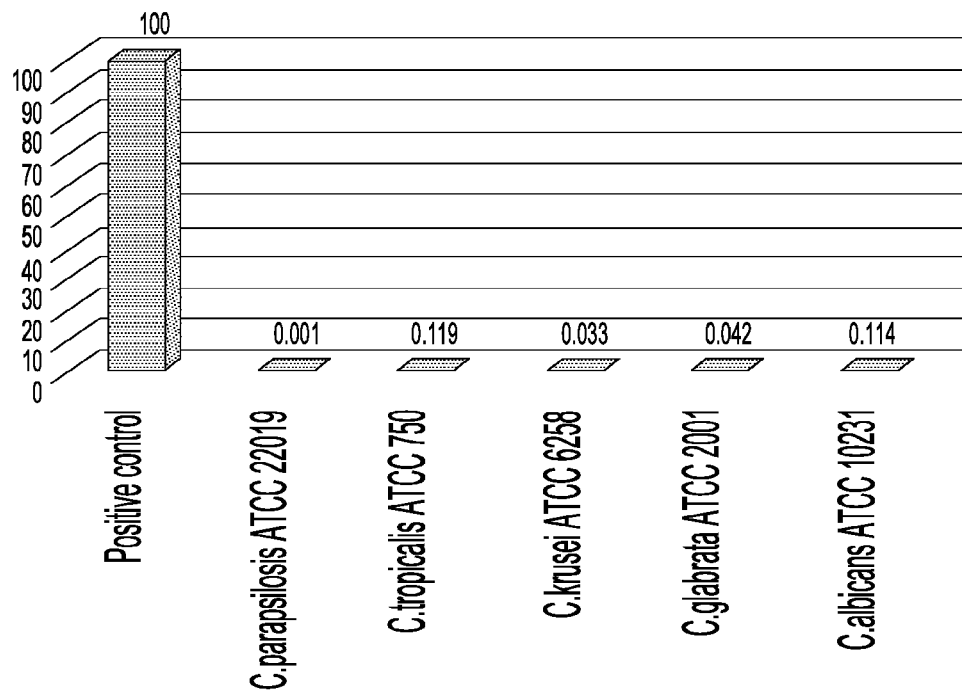
FIG. 10 shows the activity of *Lactobacillus fermentum* LF5 against several species of *Candida*.

Once the resistance of most of the Candida species to the two reference drugs is detected, the ability of Lactobacillus fermentum to inhibit the yeast growth was assessed. As shown in FIG. 9, all the tested strains of Lactobacillus, namely LF5, LF09, LF10 and LF11, shown the capability to significantly inhibit the growth of the five species of Candida by at least four logarithms. Furthermore, the best result obtained with miconazole against C. parapsilosis is even two logarithms lower. The results for LF5 are reported in FIG. 10.

Interestingly, the dose of antibiotic in humans generally provides the management of a maximum of 400 mg/die: such a per os concentration peaks an average plasma concentration of 30-40 pg/ml, a value which is much lower than the efficacy cut-off in the case of resistant strains.

Discussion

The possible role of L. fermentum compared with miconazole and fluconazole against different species of Candida was tested in vitro.

Specifically, the growth capability of Candida species in the presence of increasing concentrations of miconazole and fluconazole by two distinct tests, the broth macrodilution test for miconazole and E-test for fluconazole, was quantified.

The present results are highly surprising and represent the first proof for an in vitro relatively poor efficacy of azoles, which are widely used in counteracting the growth of Candida species and for a high effectiveness of lactic acid bacteria belonging to the species Lactobacillus fermentum. The only inhibition test was detected with C. parapsilosis ATCC 22019, even though the overall results are little relevant. The poor efficacy of azoles could account for the frequent relapses of Candida infections.

Actually, a complete eradication of the yeast from the vaginal environment could be difficult to obtain, thus maintaining the conditions for a subsequent new development and clinical manifestation of unfavorable symptoms.

On the other side, the selected strains of L. fermentum according to the invention confirmed the possibility to not only effectively and directly counteract the growth, but also the viability of several strains of Candida. One of these strains of L. fermentum, namely the strain LF5 (identified with deposit number CNCM 1-789) was used in women with acute VVC, but without any correlation with a specific species of Candida and not in the simultaneous presence of bacterial infection due to Gardnerella vaginalis, thus confirming the capability thereof in resolving the symptoms and rapidly eradicating the infection (Vicariotto F. et al. "Effectiveness of the association of 2 probiotic strains formulated in a slow release vaginal product, in women affected by vulvovaginal candidiasis: a pilot study". J Clin Gastroenterol. 2012;46 Suppl:S73-80).

8. Inhibition of Gardnerella vaginalis by L. fermentum LF5

This study was conducted in order to assess the ability of L. fermentum LF5 to directly inhibit Gardnerella vaginalis in vitro, so that to evaluate the potential efficacy thereof even in the event of mixed vaginal infections or BV.

Materials and Methods

Bacterial Strains and Growth Conditions

The strain Gardnerella vaginalis being used was purchased from the American Type Culture Collection (ATCC). Before the experiment, G. vaginalis ATCC 14018 was cultured in a heart-brain infusion (BHI) broth (Oxoid, Milan, Italy) consisting of 2% gelatin (weight/weight), 0.5% yeast extract, 0.1% starch, and 0.1% glucose (7).

The strain Lactobacillus fermentum LF5 of this study was isolated from the vaginal swab of a healthy female subject and classified according to the phenotypic and genotypic characteristics thereof.

It was cultured overnight in De Man, Rogosa and Sharpe (MRS) broth (Difco, B D, Maryland).

Assessment of the Antagonistic Activity of LF5 Against G. vaginalis

LF5 supernatants were prepared as follows: an overnight culture in MRS broth was centrifuged at 5,000× g. The resulting supernatant was neutralized at pH 6.5 with NaOH 1 N, sterilized by filtration through syringe filters (Ministart pore size 0.22 mm), and analyzed for the presence of any inhibitory molecule in the broth. Neutralized LF5 supernatants were then added with different percentages of fresh BHI broth, prepared as described above, inoculated with G. vaginalis. The growth of Gardnerella alone (positive control) and in the presence of different concentrations of neutralized supernatants ranging from 5% to 20%, after 24 and 48 hours of incubation at 37° C. under microaerophilic conditions, was quantified by optical density at 600 nm (OD600). The growth of the positive control (Gardnerella alone) was assessed in BHI broth added to an amount of fresh MRS broth ranging from 5% to 20%. Thus, the positive controls were as similar as possible to the tubes inoculated with LF5. This test was repeated three times in order to ensure reliability and reproducibility.

Results

The in vitro inhibition results of LF5 against G. vaginalis ATCC 10231 are reported in Table 11. L. fermentum LF5 shown a significant activity after both 24 and 48 hours (46% and 82% with 20% neutralized supernatant, respectively). A significant inhibition of the dose-dependent growth was detected with the neutralized supernatants in particular after 48 hours of incubation, up to a growth inhibition of G. vaginalis of even 80% (Tab. 9).

TABLE 11

L. fermentum LF5 - biological activity against G. vaginalis.

| | 24 h incubation | | | 48 h incubation | | |
|---|---|---|---|---|---|---|
| | OD = 600 nm | | | | | |
| Sample | +5% | +10% | +20% | +5% | +10% | +20% |
| G. vaginalis + MRS (%) | 1.379 ± 0.01 | 1.542 ± 0.02 | 1.557 ± 0.015 | 1.384 ± 0.014 | 1.554 ± 0.01 | 1.562 ± 0.016 |
| G. vaginalis + LF5 (%) | 0.764 ± 0.008 | 0.645 ± 0.006 | 0.843 ± 0.007 | 0.562 ± 0.006 | 0.336 ± 0.004 | 0.275 ± 0.003 |

LF5 supernatant (0.5, 1 and 2 mL) is able to inhibit the growth of *G. vaginalis* even after 24 hours, but the best inhibition is after 48 hours. Positive control = *G. vaginalis* – growth in an optimal medium plus an equal volume of MRS (5%, 10% and 20%) (n = 3).

The study shows that *L. fermentum* LF5 is able to exert a fundamental inhibitory activity against *G. vaginalis*, thus revealing a multipurpose application. The above-cited data show that the strain LF5 is also useful for the treatment of vulvovaginal candidiasis (VVC), due to different strains, among which, inter alia, *Candida albicans*; accordingly it can be used even in the clinical management of mixed vaginitis.

The invention claimed is:

1. A method of treating a vaginal infection, the method comprising
administering to a subject a formulation, comprising at least one pharmaceutical or food-grade excipient and bacteria comprising at least a first strain of bacteria belonging to the species *Lactobacillus fermentum*; said formulation being a vaginal formulation in liquid form and/or an oral formulation,
wherein said vaginal infection comprises vaginal infection by the pathogenic bacterium *Gardnerella vaginalis*, and
wherein the first strain comprises strain LF05 with deposit number DSM 32277 or CNCM I-789.

2. The method according to claim 1, wherein said bacteria further comprises a second strain of bacteria selected from the group consisting of strains of bacteria from Nos. 3 to 14 below:

| List of tested strain | Abbreviation | ID | Deposit | Depositor |
|---|---|---|---|---|
| No. 3 *L. fermentum* | LF 06 | 1456 | DSM 18295 | Anidral Srl |
| No. 4 *L. fermentum* | LF 07 | 1459 | DSM 18296 | Anidral Srl |
| No. 5 *L. fermentum* | LF 08 | 1460 | DSM 18297 | Anidral Srl |
| No. 6 *L. fermentum* | LF 09 | 1462 | DSM 18298 | Anidral Srl |
| No. 7 *L. fermentum* | LF 10 | 1637 | DSM 19187 | Anidral Srl |
| No. 8 *L. fermentum* | LF 11 | 1639 | DSM 19188 | Anidral Srl |
| No. 9 *L. fermentum* | DPPMA 114 | 1757 | DSMZ 23757 | Probiotical SpA |
| No. 10 *L. fermentum* | Lb2 | 1753 | DSM 16143 | Probiotical SpA |
| No. 11 *L. fermentum* | LF 15 | 1852 | DSM 26955 | Probiotical SpA |
| No. 12 *L. fermentum* | LF16 | 1853 | DSM 26956 | Probiotical SpA |
| No. 13 *L. fermentum* | LF18 | 1897 | DSM 29197 | Probiotical SpA |
| No. 14 *L. fermentum* | LF 25 | 1956 | DSM 32275 | Probiotical SpA. |

3. The method according to claim 2, wherein said second strain is selected from the group consisting of: the No. 7 *L. fermentum*, the No. 8 *L. fermentum*, the No. 11 *L. fermentum*, the No. 12 *L. fermentum*, the No. 13 *L. fermentum* and the No. 14 *L. fermentum*.

4. The method according to claim 3, wherein said second strain is selected from the group consisting of the No. 8 *L. fermentum*, the No. 11 *L. fermentum*, the No. 13 *L. fermentum* and the No. 14 *L. fermentum*.

5. The method according to claim 2, wherein said first strain and said second strain are present in said composition at a weight ratio from 1:2 to 1:10.

6. The method according to claim 1, wherein said vaginal infection comprises vaginitis, vulvovaginitis or bacterial vaginosis due to *Gardnerella vaginalis* alone or in combination with at least one pathogen selected from the group consisting of: *Candida albicans, Candida glabrata, Candida parapsilosis, Candida krusei, Candida tropicalis, Trichomonas vaginalis, Neisseria gonorrhoeae, Escherichia coli, Herpes simplex* and Hemophilus *Ducreyi*.

7. The method according to claim 1, wherein said vaginal infection is caused by *Candida albicans* and *Gardnerella vaginalis*.

8. The method according to claim 1, wherein said oral formulation is in a solid form or in a liquid form.

9. The method according to claim 8, wherein said oral formulation is in the form of powder, granules, tablet, or lozenge.

10. The method of claim 8, wherein said vaginal formulation is in the form of solution, vaginal douche, dispersion or gel.

11. The method according to claim 10, wherein said bacteria contain said first strain of bacteria at a concentration from $1\times10^8$ to $1\times10^{12}$ CFU/g.

12. The method according to claim 10, wherein said bacteria contain said first strain of bacteria at a concentration from $1\times10^6$ to $1\times10^{10}$ CFU/g.

* * * * *